United States Patent
VanderWoude et al.

(10) Patent No.: US 9,943,291 B2
(45) Date of Patent: Apr. 17, 2018

(54) SPECIMEN CASSETTE WITH A REMOVABLE CATCH TRAY FOR RETRIEVING TISSUE SAMPLES FROM A FLUID STREAM GENERATED DURING A MEDICAL/SURGICAL PROCEDURE

(71) Applicant: Stryker Corporation, Kalamazoo, MI (US)

(72) Inventors: Brian VanderWoude, Portage, MI (US); Brian MacLachlan, Spring Lake, MI (US); Stephen Isham, Mattawan, MI (US); Stephen Reasoner, Kalamazoo, MI (US); David Hershberger, Kalamazoo, MI (US); Chad Drake, Kalamazoo, MI (US); Benjamin Edinger, Grand Haven, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 319 days.

(21) Appl. No.: 14/302,508

(22) Filed: Jun. 12, 2014

(65) Prior Publication Data
US 2014/0323914 A1 Oct. 30, 2014

Related U.S. Application Data

(63) Continuation of application No. PCT/US2012/069516, filed on Dec. 13, 2012.
(Continued)

(51) Int. Cl.
*A61B 10/00* (2006.01)
*A61M 1/00* (2006.01)
*A61B 10/02* (2006.01)

(52) U.S. Cl.
CPC ...... *A61B 10/0045* (2013.01); *A61B 10/0096* (2013.01); *A61B 10/02* (2013.01);
(Continued)

(58) Field of Classification Search
CPC .................. A61B 10/0045; A61B 10/0096
See application file for complete search history.

(56) References Cited

U.S. PATENT DOCUMENTS 3,844,407 A 10/1974 Buie
4,376,053 A * 3/1983 Bullock ............... A01J 5/0134
119/14.16
(Continued)

FOREIGN PATENT DOCUMENTS

EP 2100550 A1 9/2009
JP S5539296 A 3/1980
(Continued)

OTHER PUBLICATIONS

"ISA Search Report & Written Opinion" for PCT/US2012/069516, dated Apr. 5, 2013.
(Continued)

*Primary Examiner* — Michael C Stout
*Assistant Examiner* — Nicholas E Kolderman
(74) *Attorney, Agent, or Firm* — Howard & Howard Attorneys PLLC

(57) ABSTRACT

A cassette (2600) for use with a medical waste collection system (30). The cassette includes a housing (2602, 2612) shaped to be removably attached to a receptacle (1699) integral with the housing. A sleeve (2640) is attached to the cassette so as to be located forward of the housing. The sleeve is formed with a void space. A fitting (2664) for collection to a suction line is attached to the sleeve. A screen (2714) is removably fitted in the sleeve void space. The screen is fitted in the sleeve void space when it is desirable
(Continued)

to catch tissue that may be entrained in the fluid stream from the suction line.

39 Claims, 81 Drawing Sheets

Related U.S. Application Data

(60) Provisional application No. 61/576,410, filed on Dec. 16, 2011, provisional application No. 61/593,675, filed on Feb. 1, 2012.

(52) U.S. Cl.
CPC ... *A61M 1/0058* (2013.01); *A61B 2010/0061* (2013.01); *A61M 1/0056* (2013.01); *A61M 2205/12* (2013.01)

(56) References Cited

U.S. PATENT DOCUMENTS

| | | | |
|---|---|---|---|
| 5,223,151 A | 6/1993 | Rojas | |
| 5,383,234 A | 1/1995 | Russell | |
| 5,624,418 A | 4/1997 | Shepard | |
| 5,681,742 A | 10/1997 | MersKelly et al. | |
| 5,928,935 A | 7/1999 | Reuss, Jr. et al. | |
| 6,562,233 B1 | 5/2003 | Schilling et al. | |
| 6,749,319 B1 | 6/2004 | Muse | |
| 7,294,256 B2 | 11/2007 | Happel et al. | |
| 7,615,037 B2 | 11/2009 | Murray et al. | |
| 7,621,898 B2 | 11/2009 | Lalomia et al. | |
| 7,981,049 B2 | 7/2011 | Ritchie et al. | |
| 8,088,079 B2 | 1/2012 | Kaye et al. | |
| 9,782,524 B2 | 10/2017 | Reasoner et al. | |
| 2003/0073928 A1 | 4/2003 | Kortenbach et al. | |
| 2003/0125639 A1 | 7/2003 | Fisher et al. | |
| 2006/0231508 A1 | 10/2006 | Marzett et al. | |
| 2007/0135778 A1 | 6/2007 | Murray et al. | |
| 2007/0191731 A1* | 8/2007 | Kaye | A61B 10/0096 600/562 |
| 2011/0106029 A1 | 5/2011 | Garren et al. | |
| 2014/0336599 A1 | 11/2014 | Patel et al. | |

FOREIGN PATENT DOCUMENTS

| | | |
|---|---|---|
| JP | 2007209764 A | 8/2007 |
| JP | 2009519776 A | 5/2009 |
| WO | 2004075740 A1 | 9/2004 |

OTHER PUBLICATIONS

Machine-assisted English translation for JPS 55-39296 extracted from espacenet.com database on Nov. 13, 2017, 7 pages.

English language abstract for JP 2007-209764 extracted from espacenet.com database on Nov. 13,2017, 2 pages.

English language abstract not found for JP 2009-519776; however, see English language equivalent U.S. Pat. No. 9,782,524. Original document extracted from espacenet.com database on Nov. 13, 2017, 5 pages.

English language abstract for WO 2004/075740 extracted from espacenet.com database on Nov. 13, 2017, 2 pages.

* cited by examiner

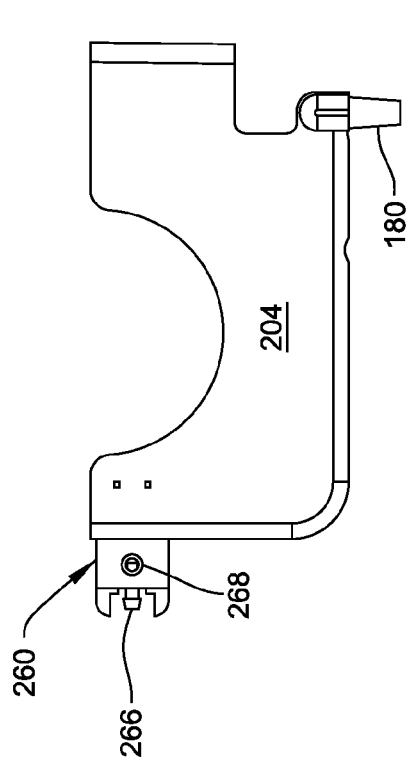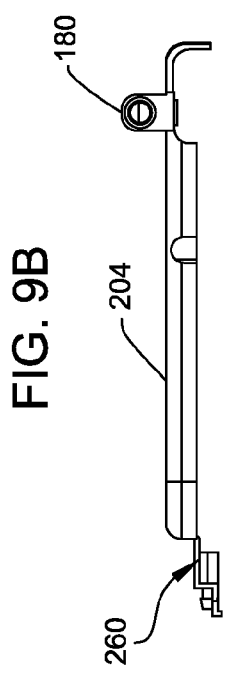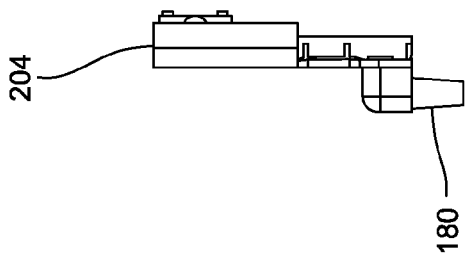
FIG. 9A  FIG. 9B  FIG. 9C  FIG. 9D

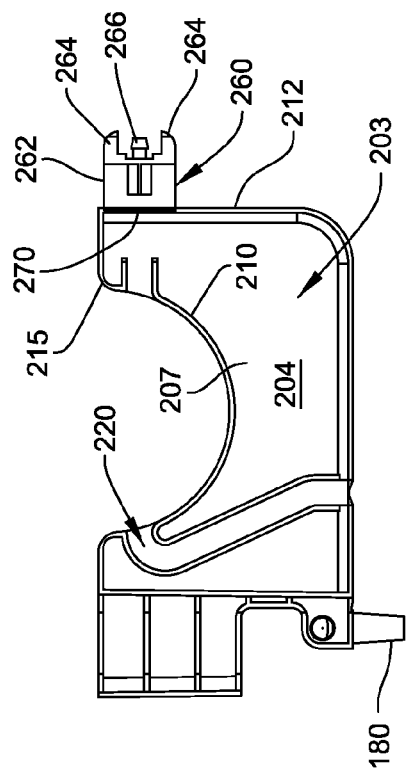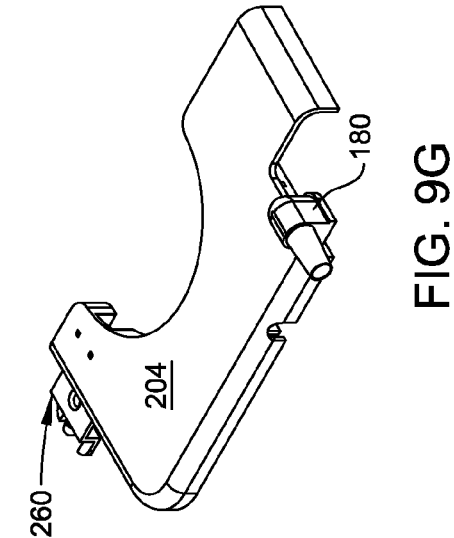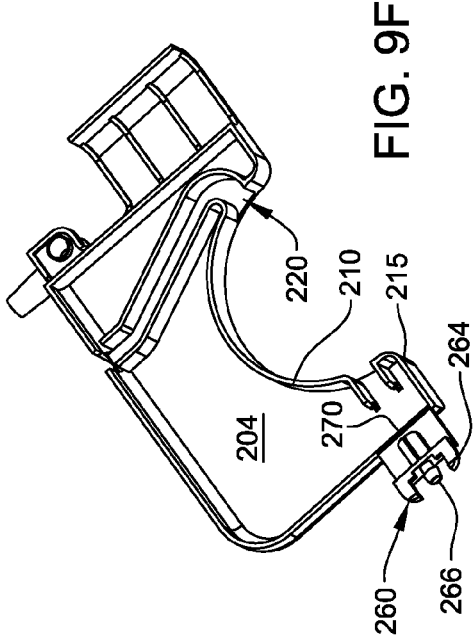

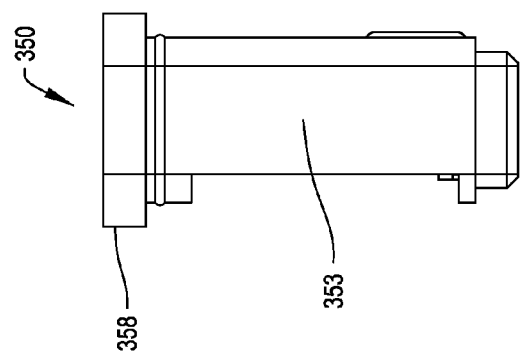
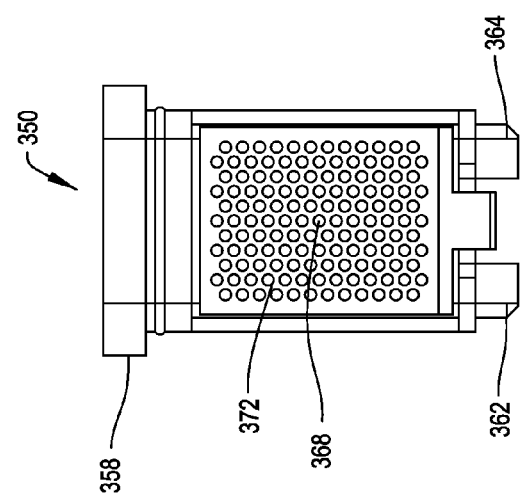
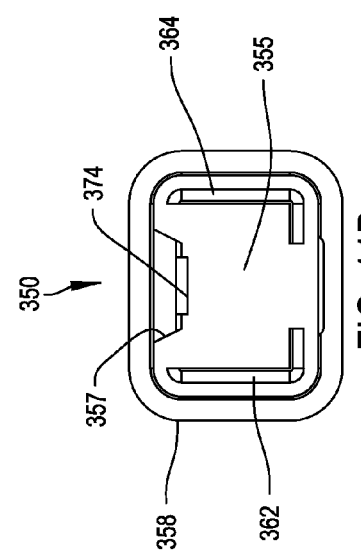

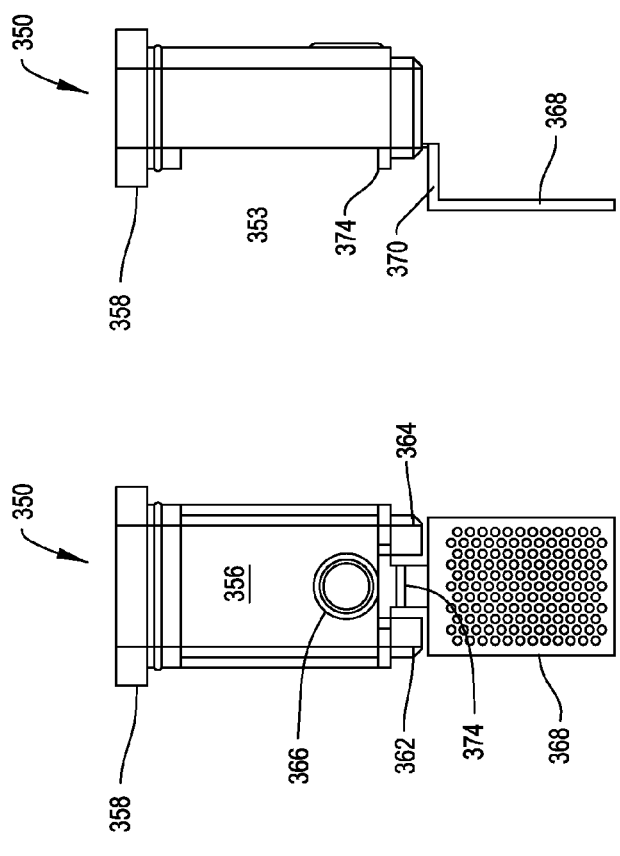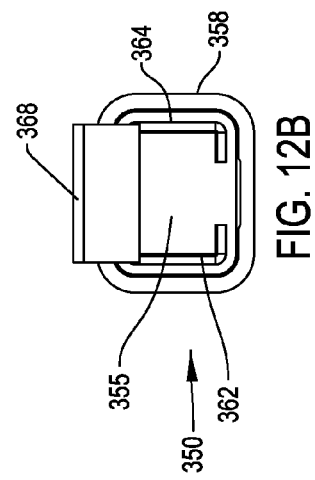

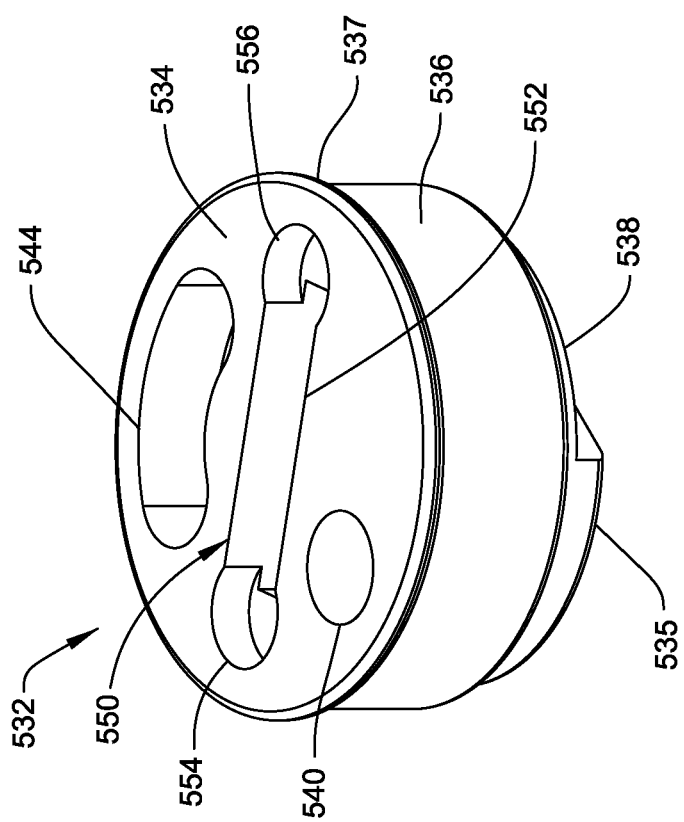

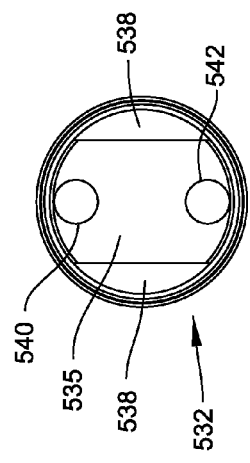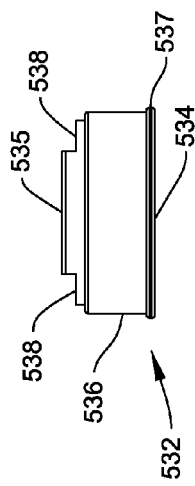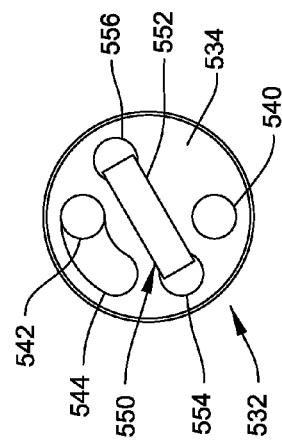

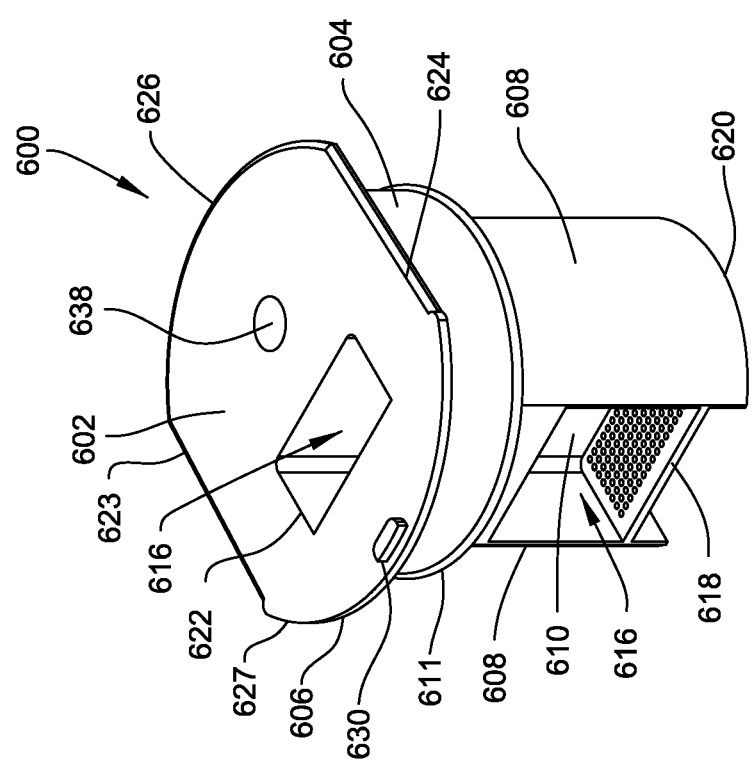

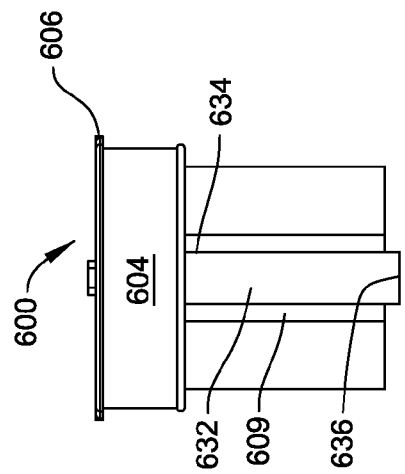
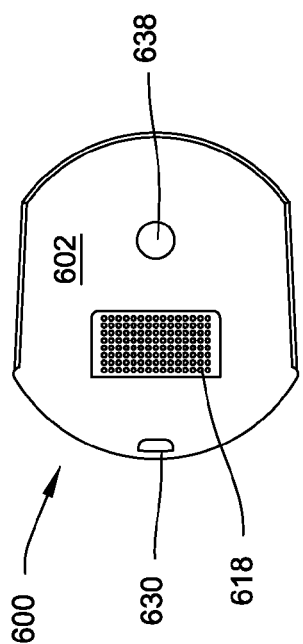
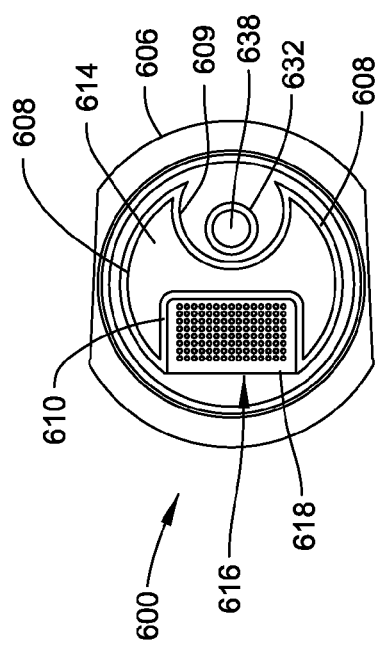

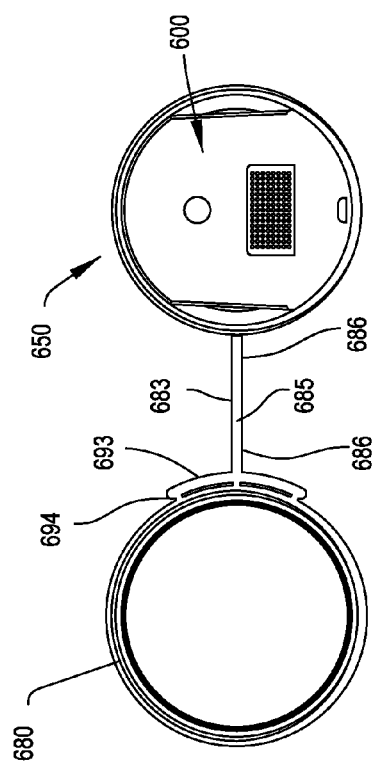
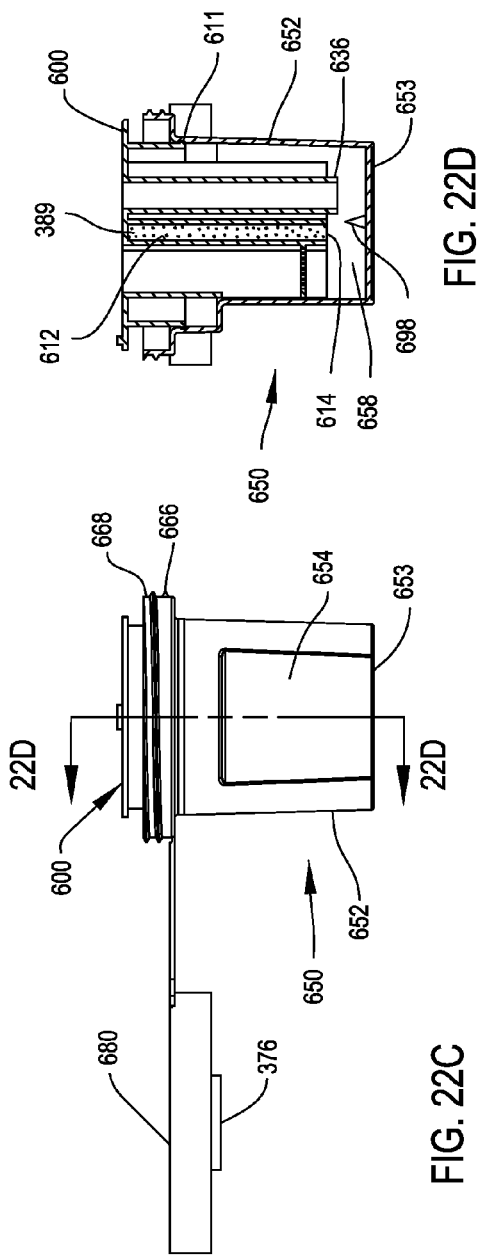
FIG. 22B
FIG. 22C
FIG. 22D

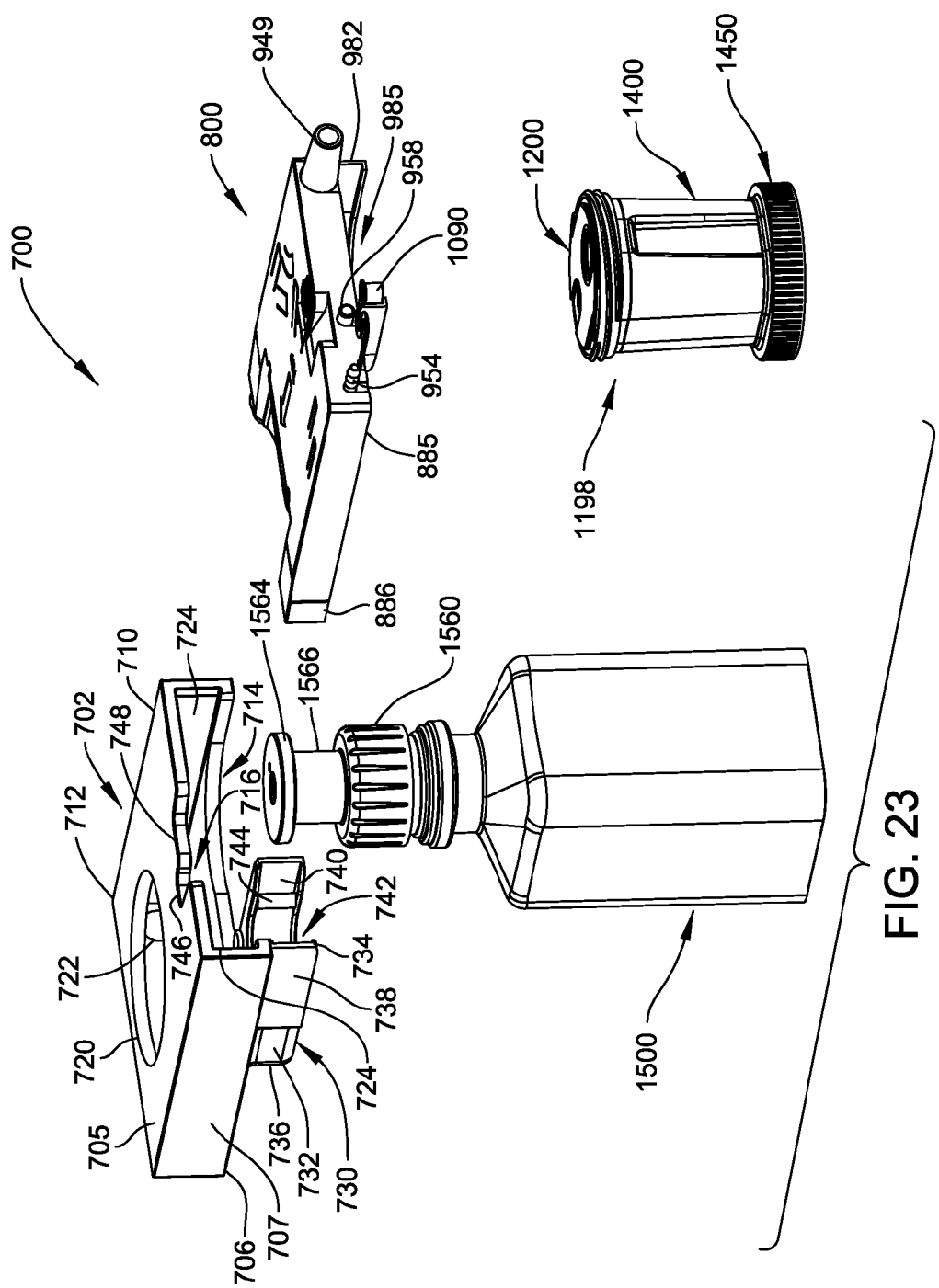

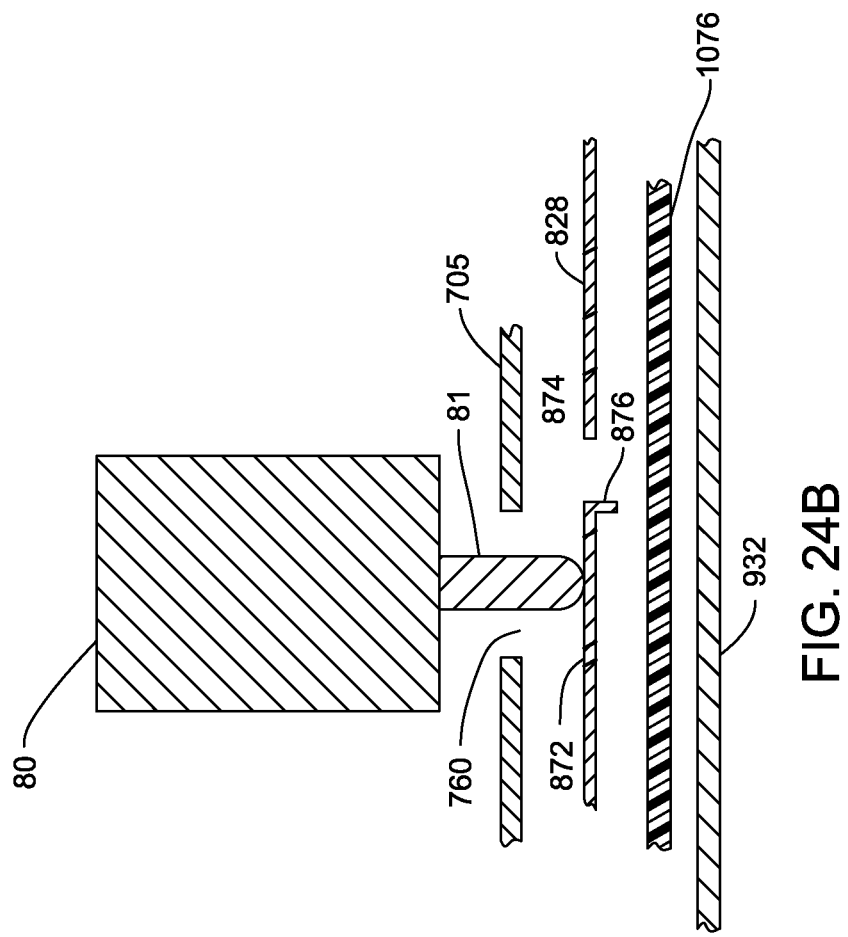

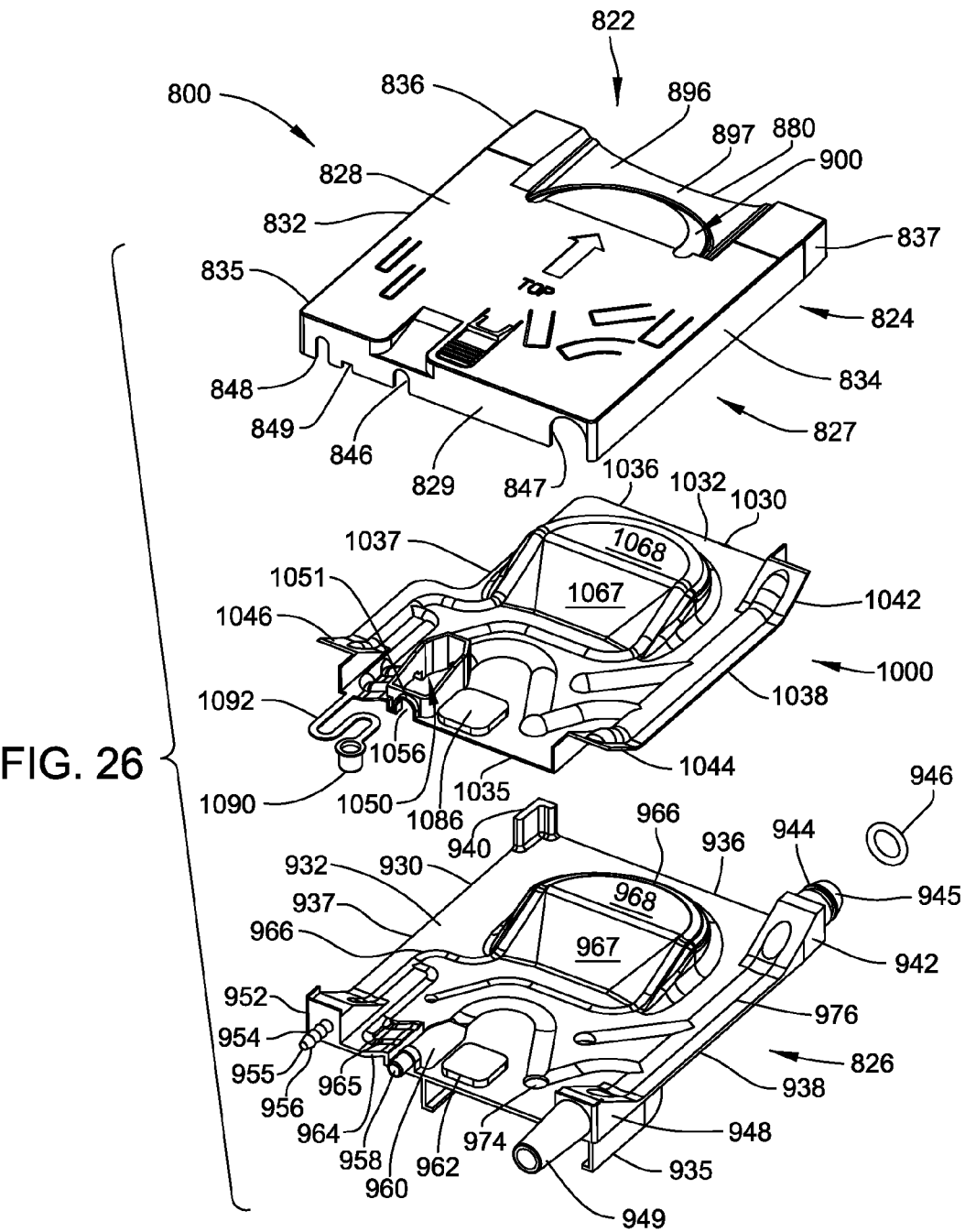

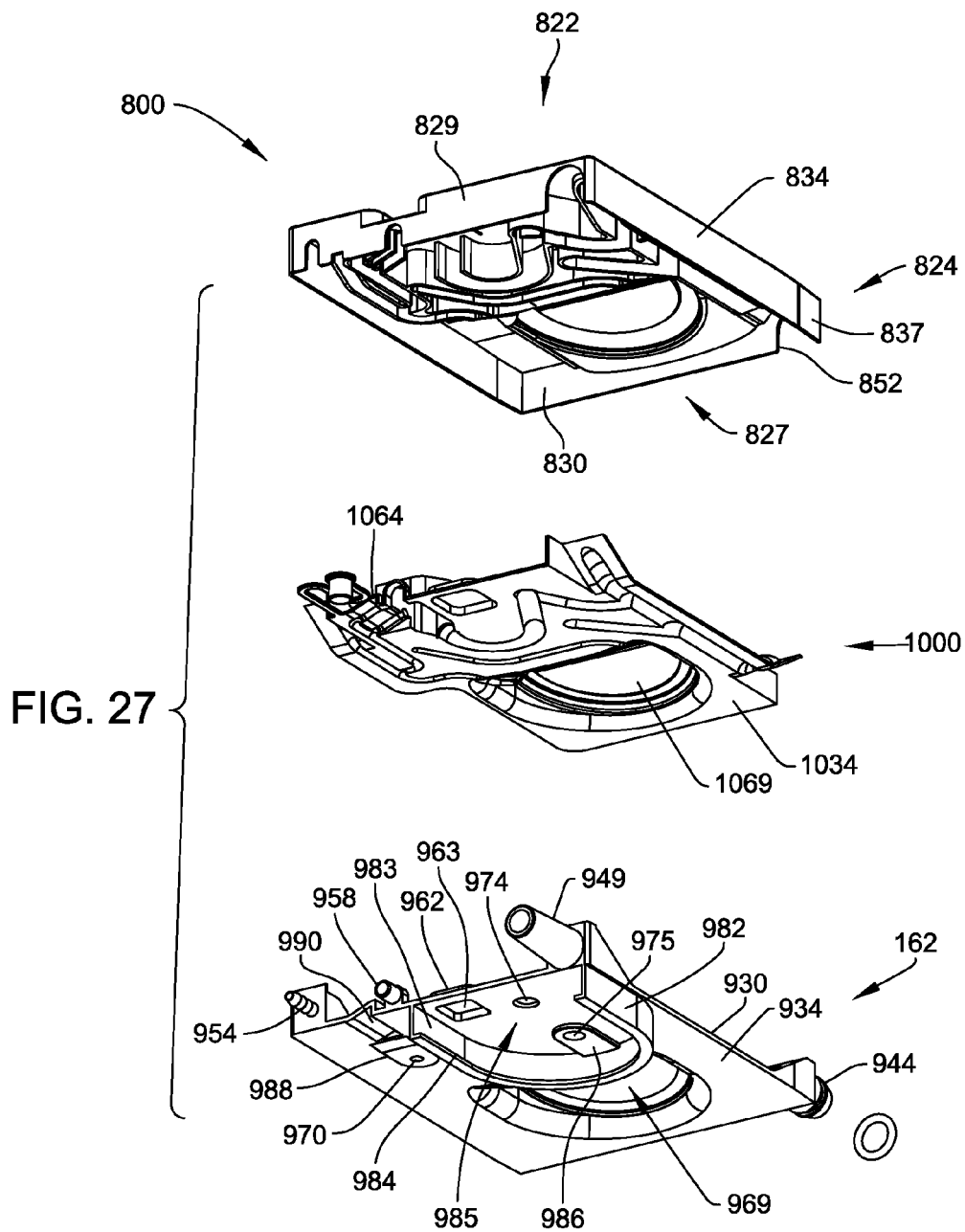

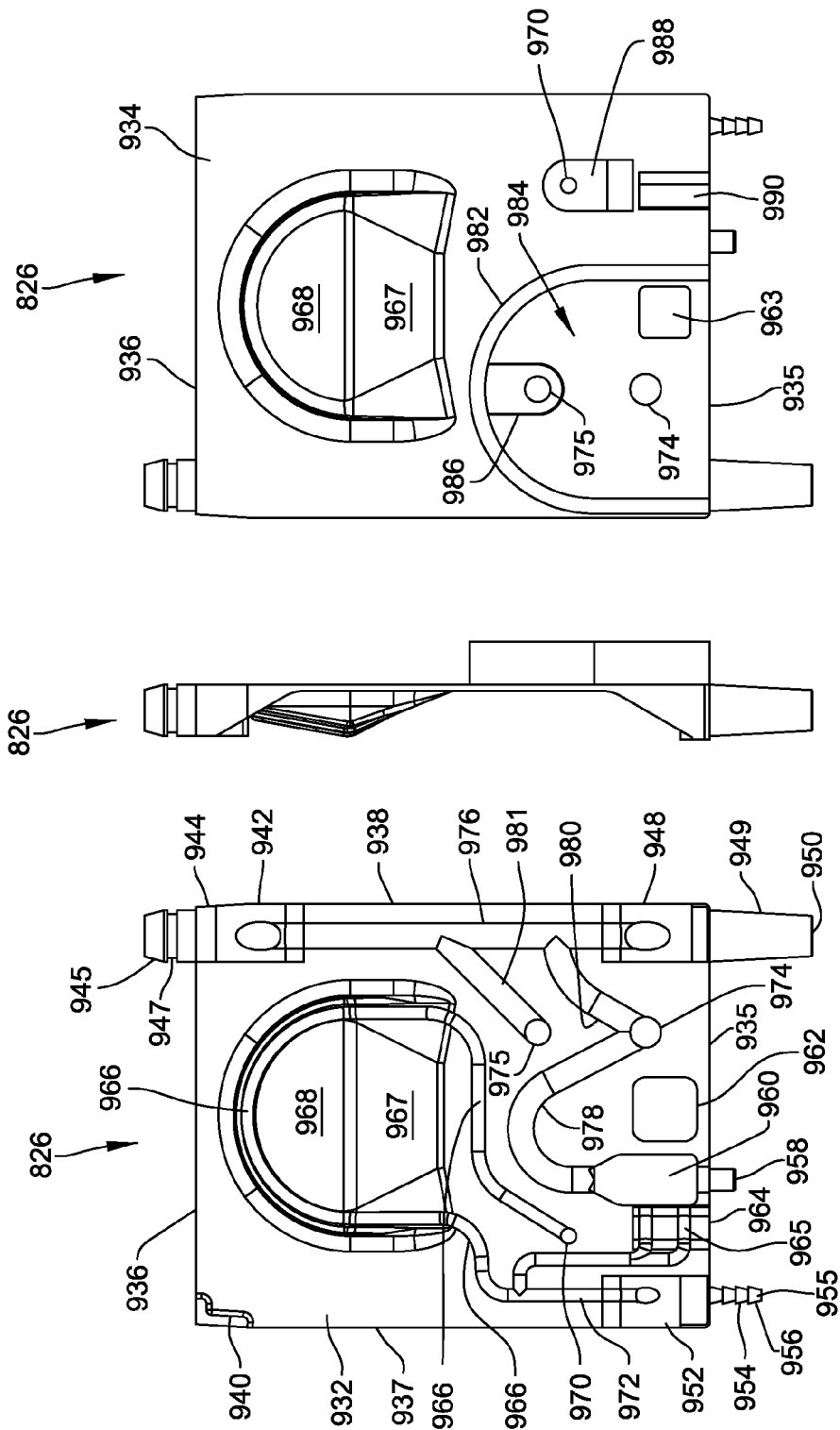

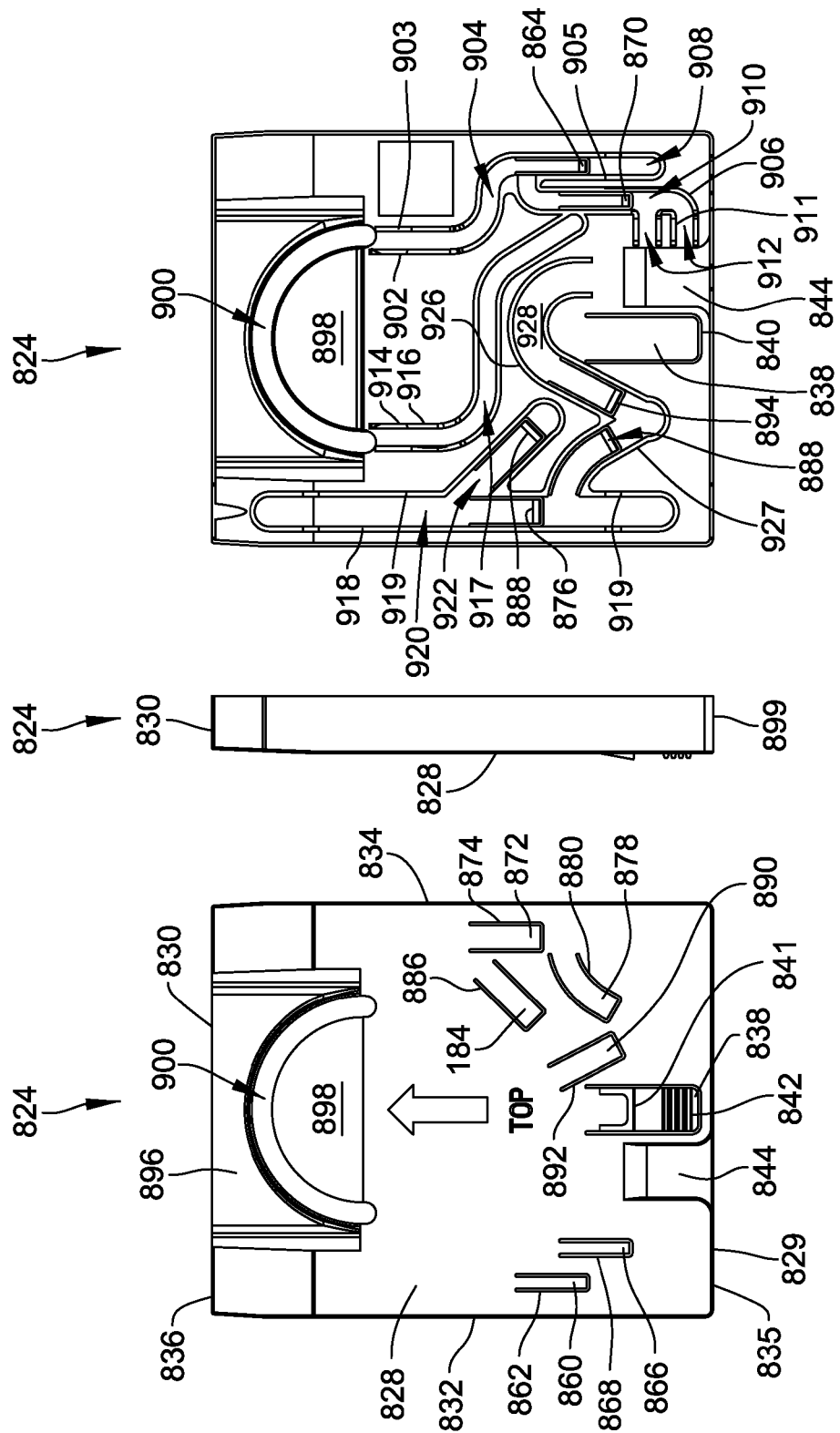

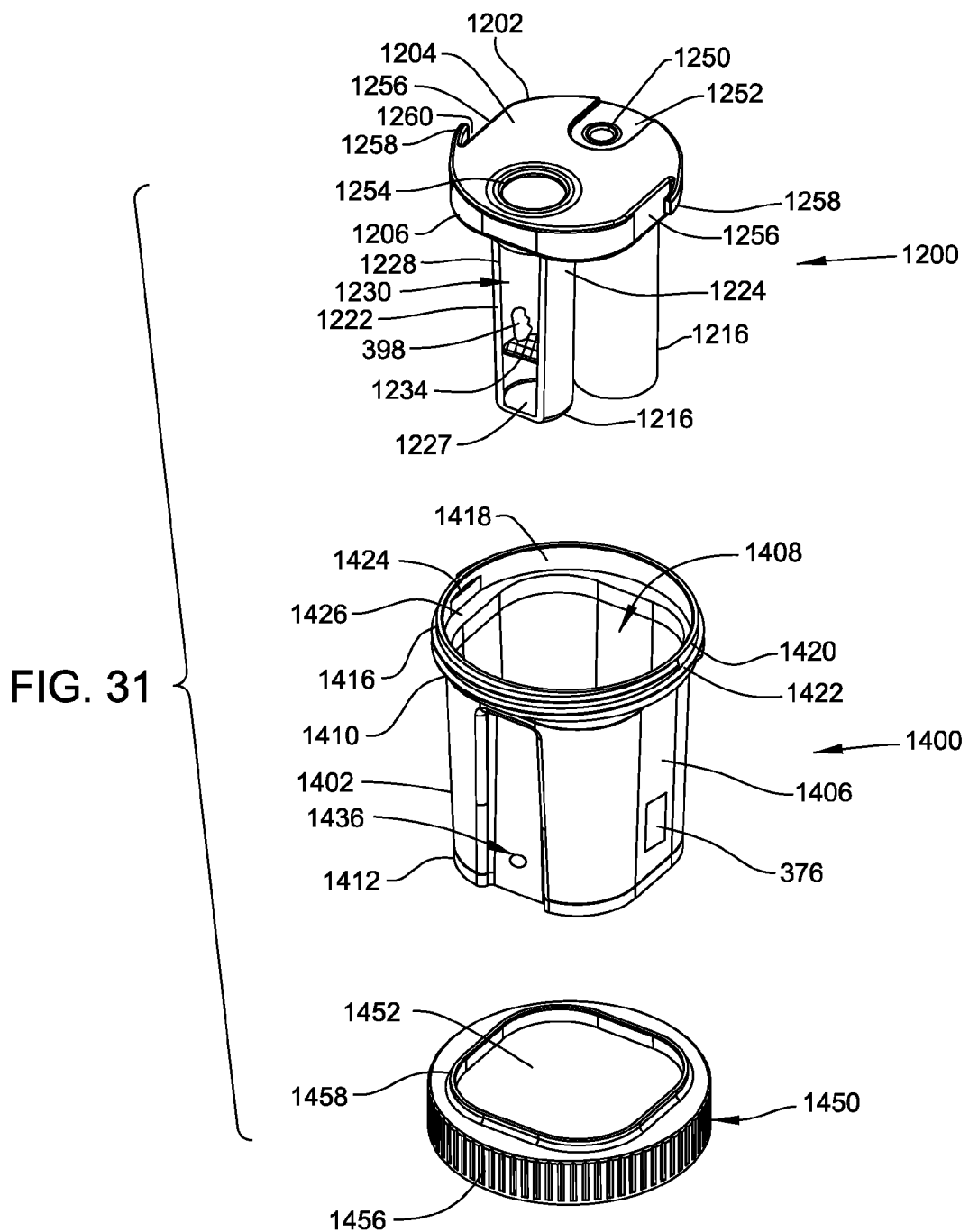

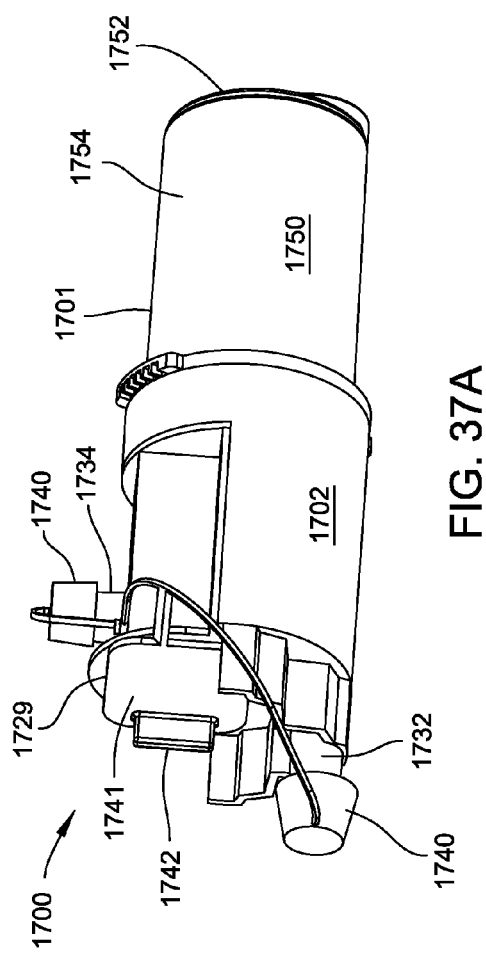
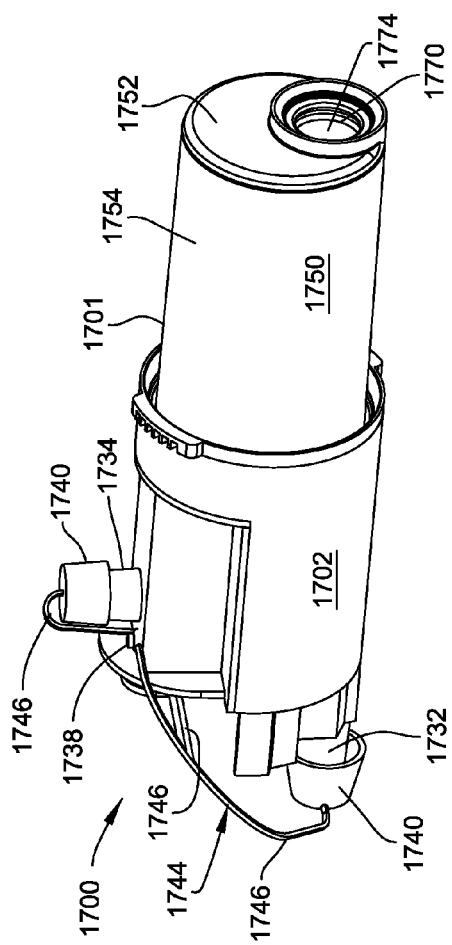
FIG. 37A
FIG. 37B

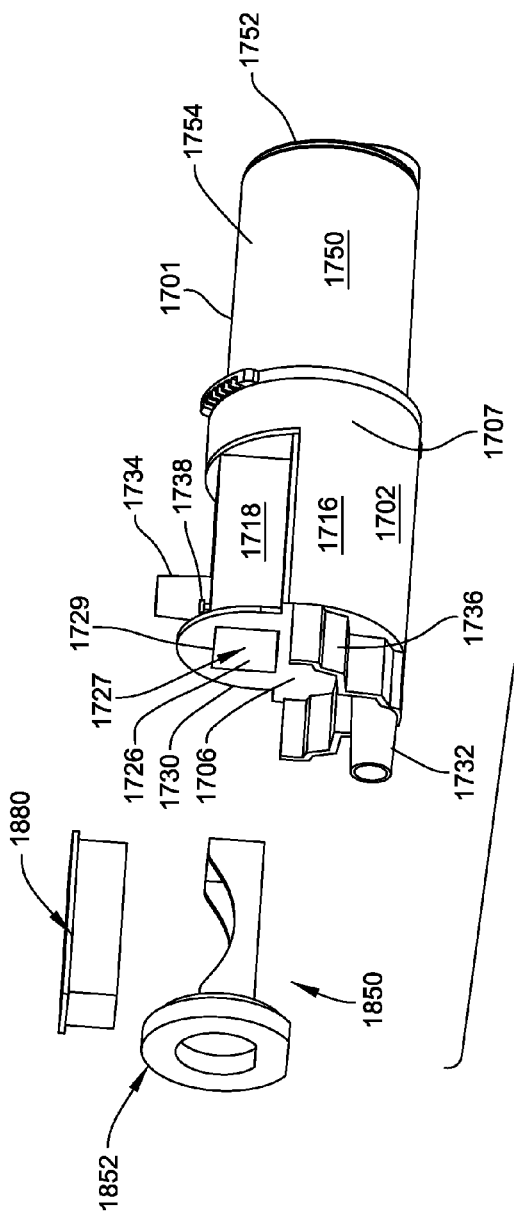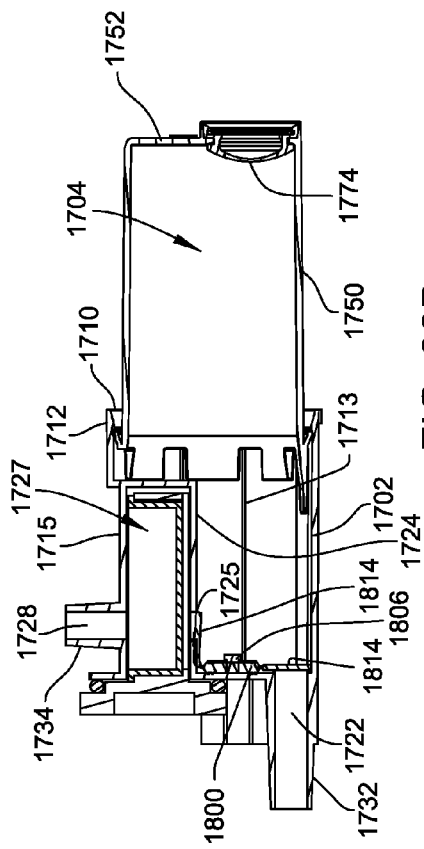
FIG. 38A
FIG. 38B

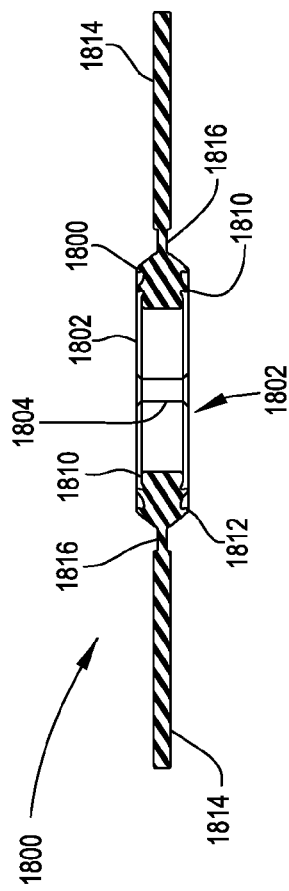
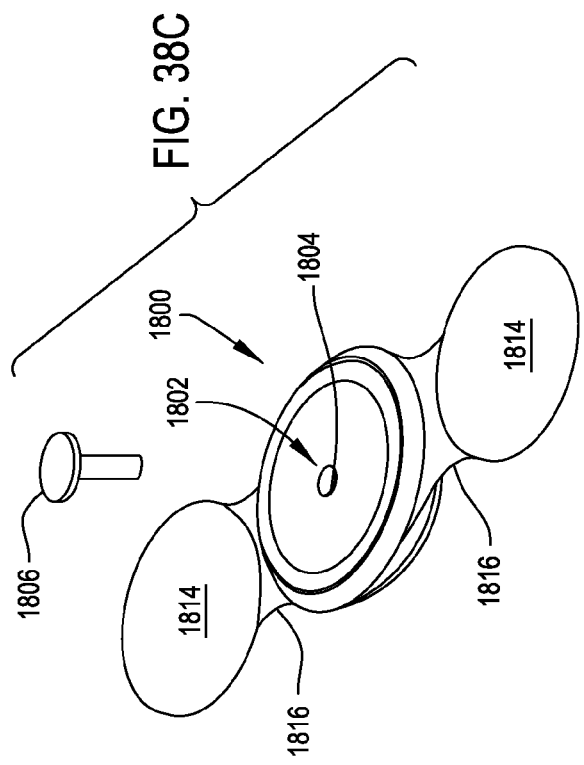
FIG. 38D
FIG. 38C

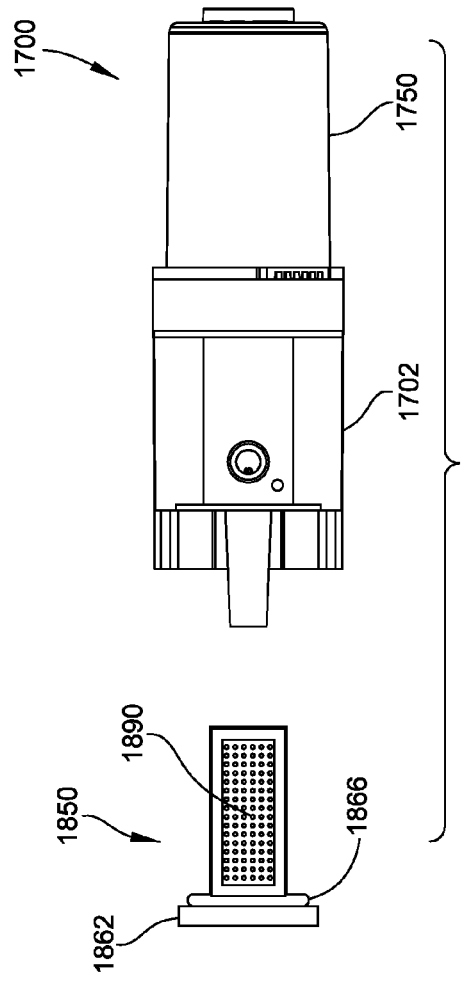
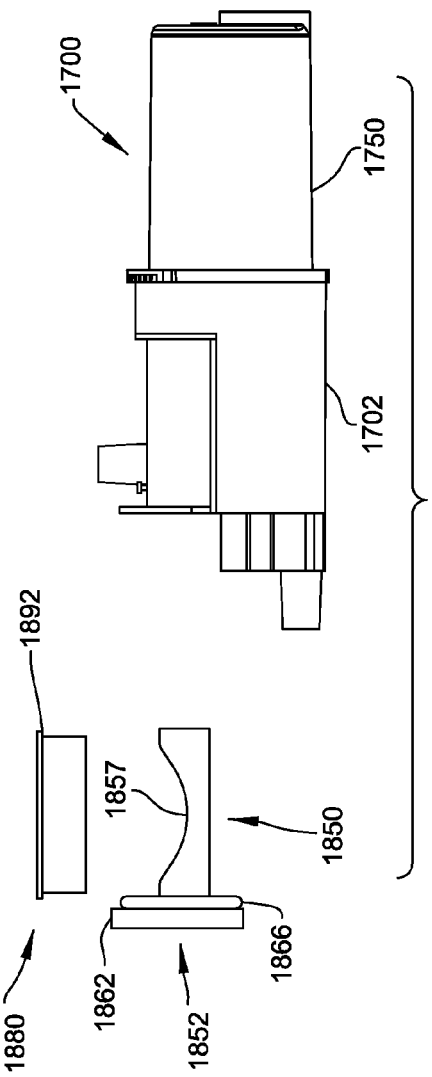
FIG. 39A
FIG. 39B

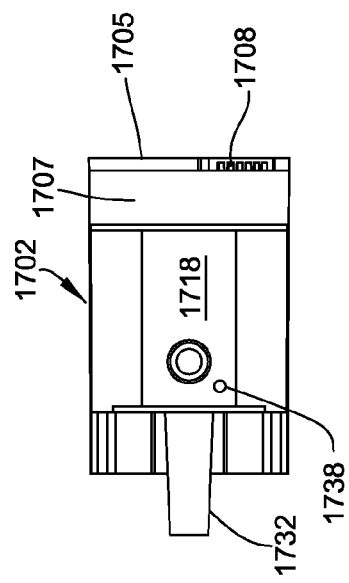
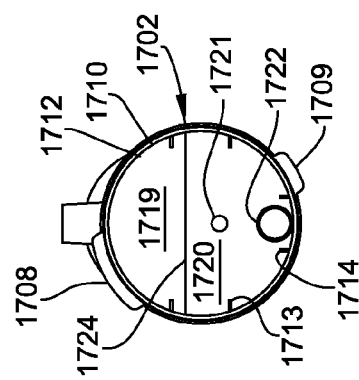

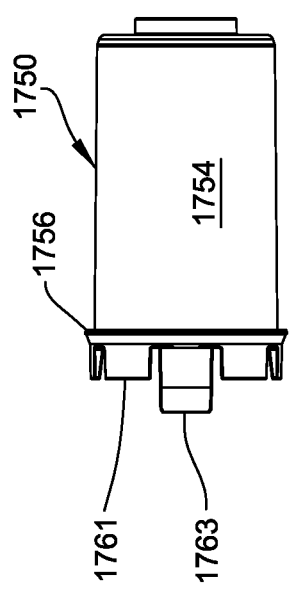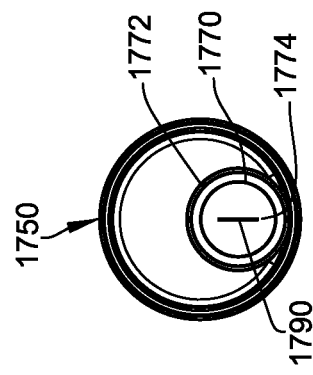

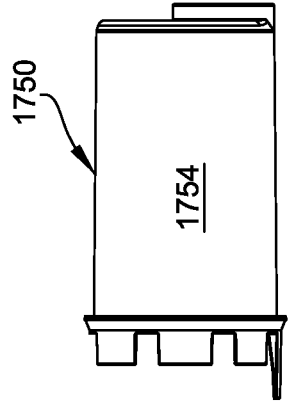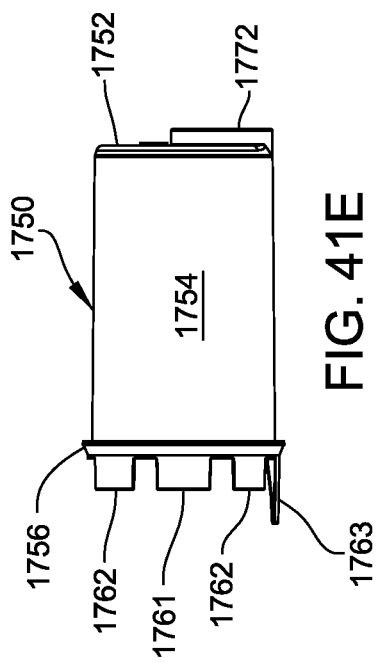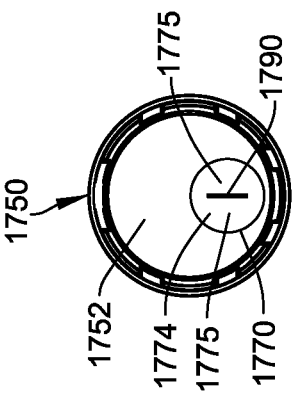

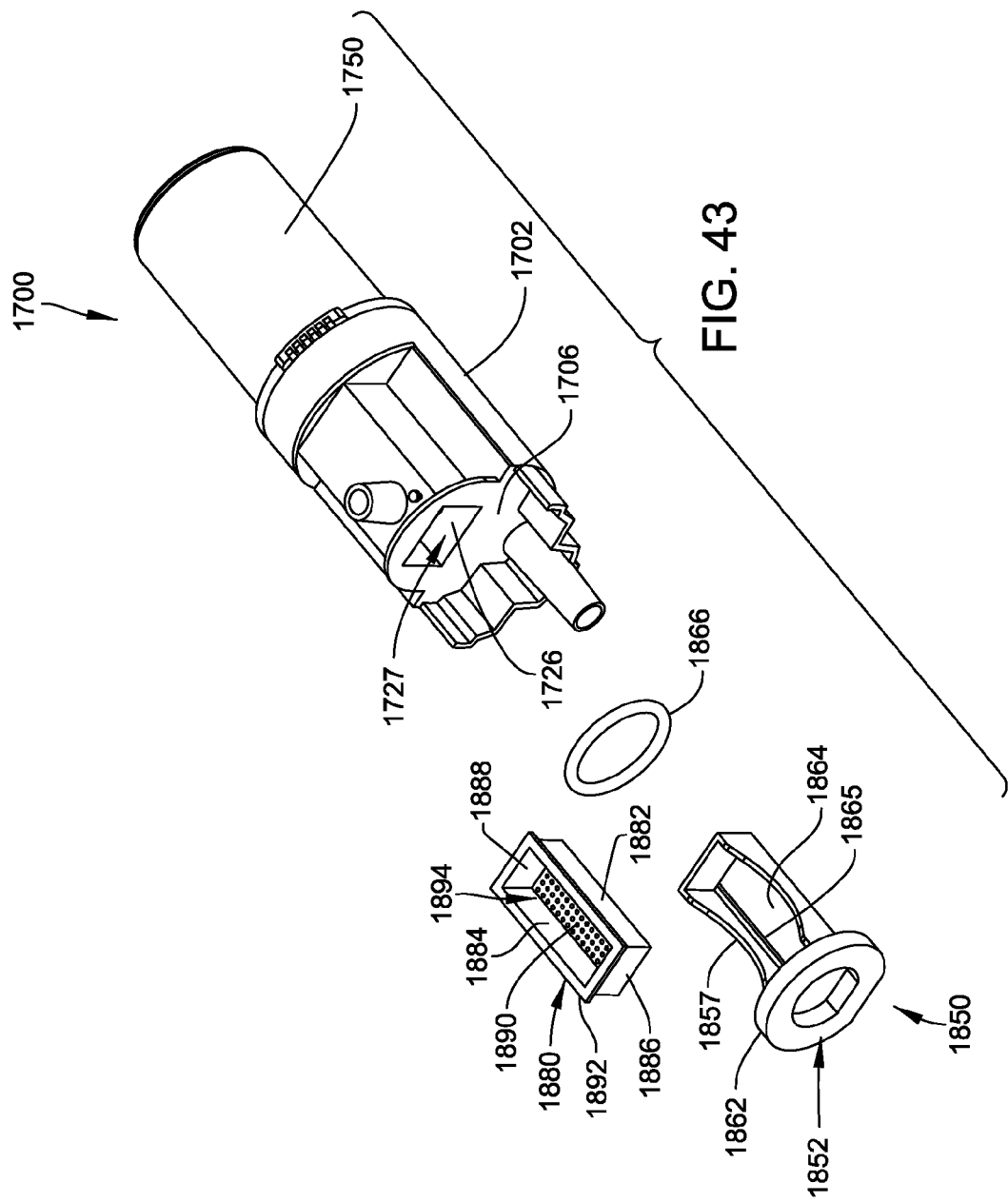

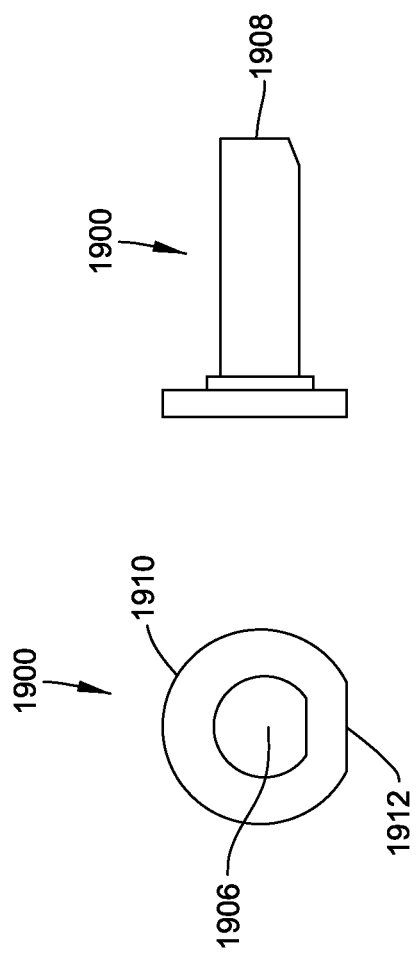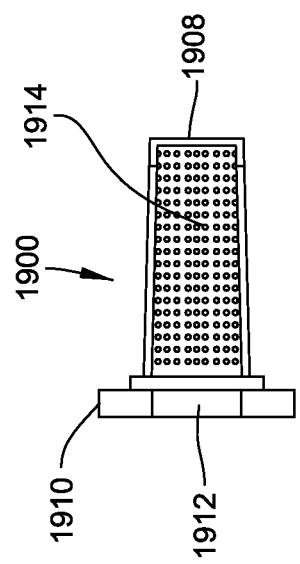
FIG. 4C
FIG. 45E
FIG. 45B

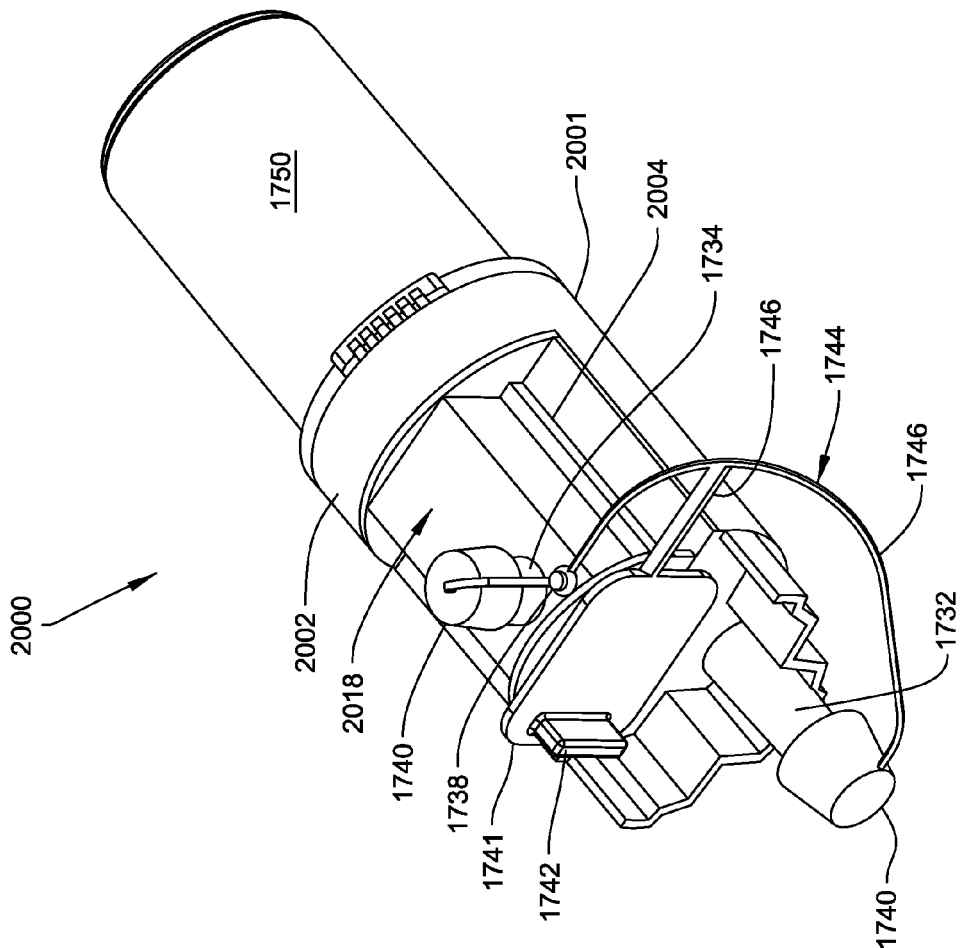

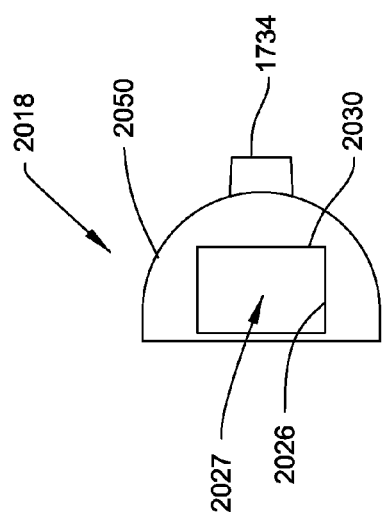
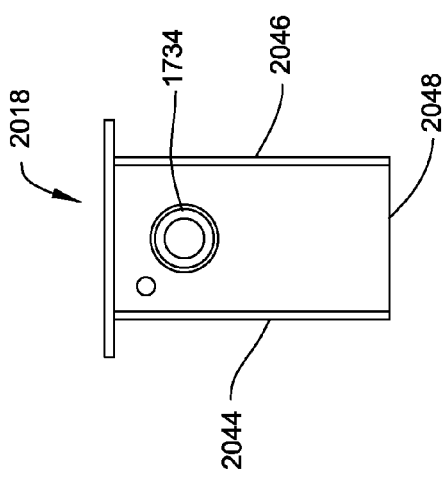

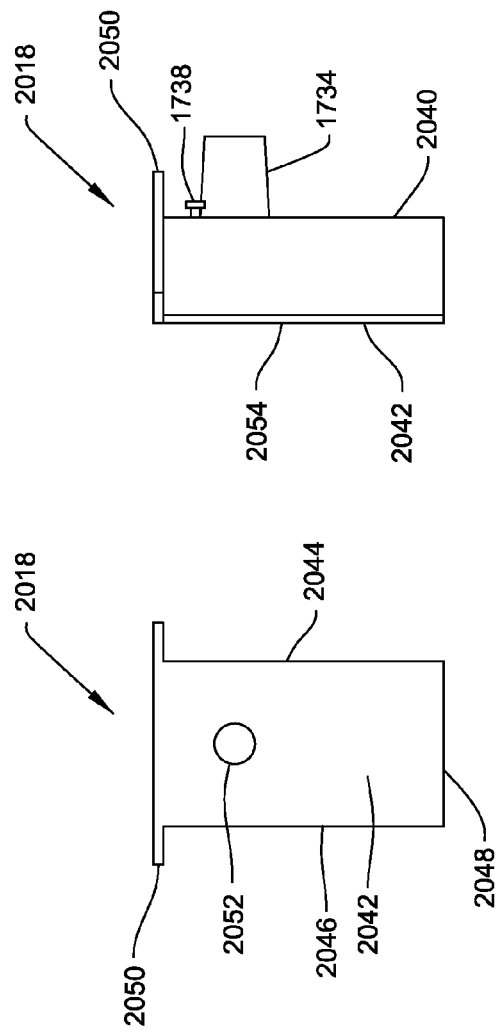
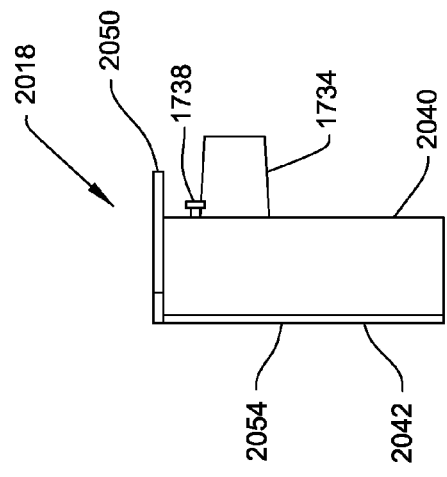
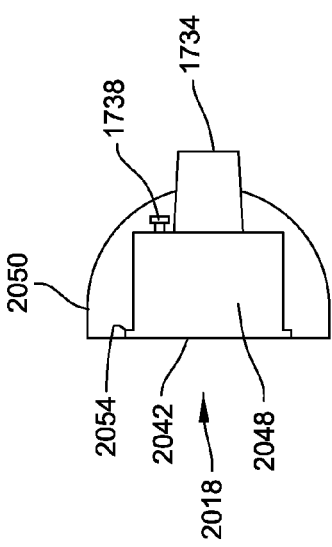
FIG. 49C
FIG. 49E
FIG. 49B

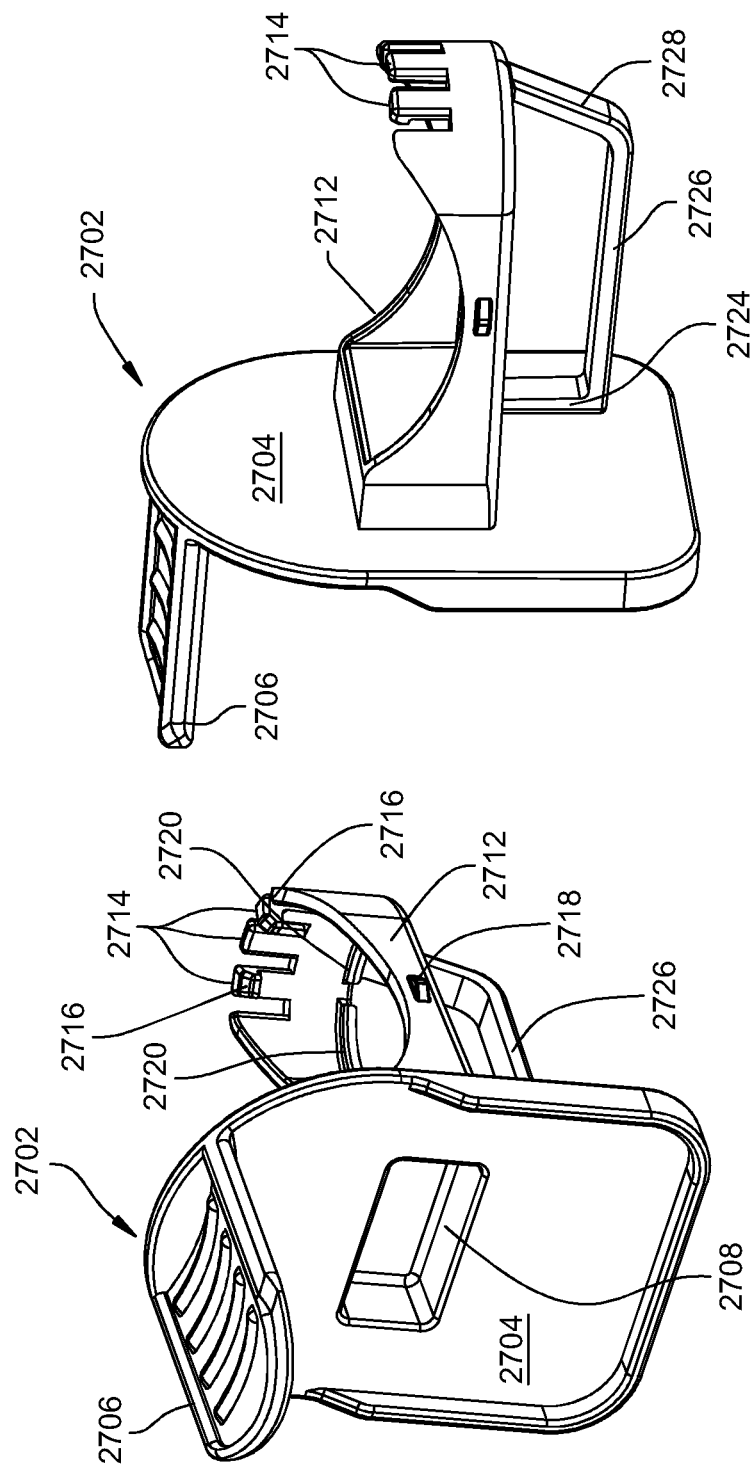

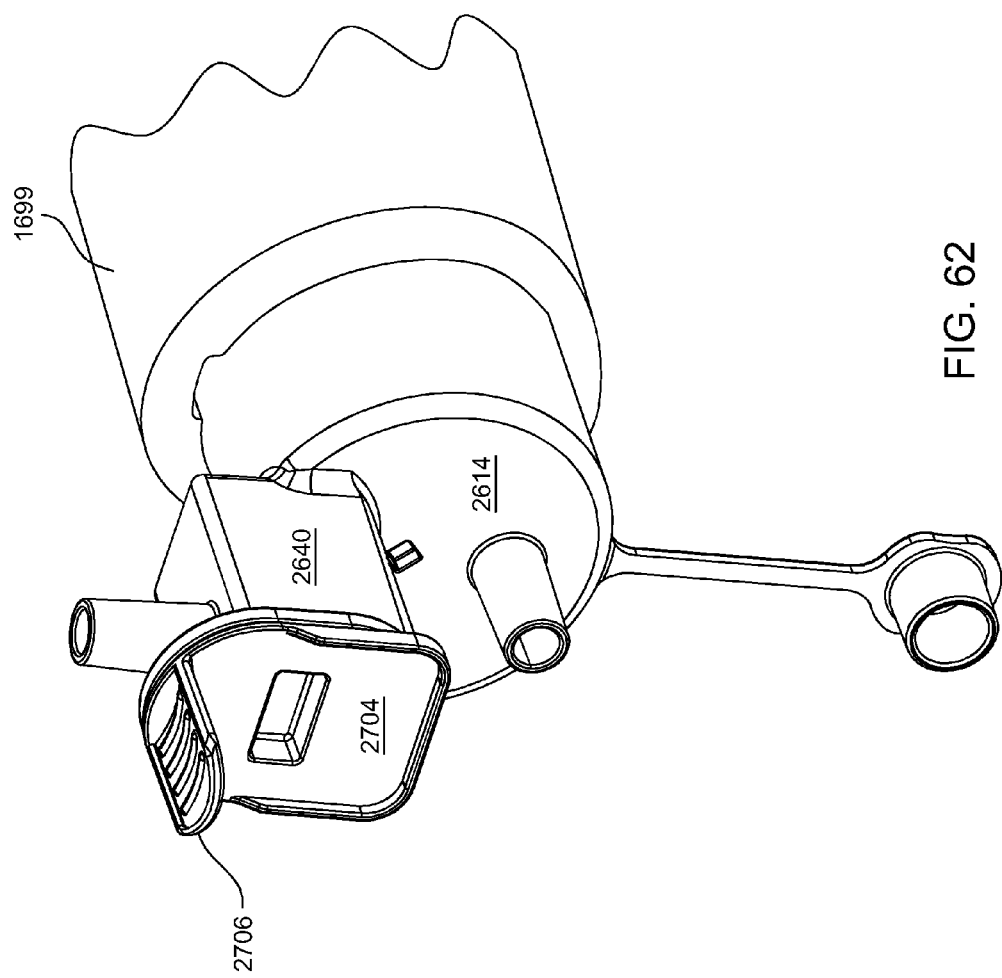

SPECIMEN CASSETTE WITH A REMOVABLE CATCH TRAY FOR RETRIEVING TISSUE SAMPLES FROM A FLUID STREAM GENERATED DURING A MEDICAL/SURGICAL PROCEDURE

RELATIONSHIP TO EARLIER FILED APPLICATIONS

This application is a continuation of PCT Pat. App. No. PCT/US2012/069516 filed 13 Dec. 2012. PCT Pat. App. No. PCT/US2012/069516 is a non-provisional of and claims priority from U.S. Provisional Pat. App. No. 61/576,410 filed 16 Dec. 2011 and U.S. Provisional Pat. App. No. 61/593,675 filed 1 Feb. 2012. The contents of the priority applications are incorporated herein by reference.

FIELD OF THE INVENTION

This invention relates generally to a system and method for collecting waste and retrieving tissue samples generated during a surgical procedure. More particularly, this invention relates to a system and method for retrieving tissue samples from the gastrointestinal tract during surgical procedures such as colonoscopies.

BACKGROUND OF THE INVENTION

A byproduct of the performance of some medical and surgical procedures is the generation of liquid, semi-solid and solid waste. This waste includes body fluids, such as blood, and irrigating solution that are introduced to the body site at which the procedure is performed. Solid and semi-solid waste generated during a procedure includes bits of tissue and small pieces of the surgical material that may be left at the site. Ideally, the waste is collected upon generation so the waste neither visually obstructs nor fouls the surgical site nor becomes a biohazard in the operating room or other location at which the procedure is being performed.

A number of systems are available for use by surgical personnel for collecting this waste as it is generated. Generally, these units include a suction source, tubing that extends from the suction source and a containment unit between the tubing and the suction source. When the system is actuated, waste is drawn through the distal end of the tubing. The suction draws the waste through the tubing so that it flows into and is stored in the containment unit. One such system is Applicants' Assignee's NEPTUNE surgical waste collection system. This particular system includes a mobile unit that includes a suction pump and two canisters. Tubing is connected to each canister through a removable manifold. Since this unit is mobile, it can be positioned in relatively close proximity to the patient on which the procedure is being performed. This reduces the extent to which the suction tubing, which invariably also functions as operating room clutter, is present around the surgical personnel. This system also has features that reduce the extent to which the surgical and support personnel are potentially exposed to the materials collected by the system. U.S. Pat. No. 7,621, 898, issued Nov. 24, 2009, the contents of which are incorporated herein by reference, describes a number of features of this system.

A feature of this system is the intake manifold. This manifold includes a filter element that traps large bits of solid matter. This is desirable because these solids can potentially clog the proximally-located components of the system. Moreover, the manifold is formed from material that makes it possible to provide the manifold as a single use item. After use of the system, effort does not have to be spent sterilizing the manifold, with its narrow conduits, or its internal filter. Instead, personnel handling the used manifold only need to contact the outer surface of this component. This process further minimizes the extent to which these individuals potentially come into contact with the waste material. The Applicants' Assignee's U.S. Pat. No. 7,615, 037 issued Nov. 10, 2009, the contents of which are incorporated herein by reference, provided a more detailed description of this type of manifold.

In some surgical procedures such as a colonoscopy, it is desirable to collect one or more tissue samples from the patient during the surgical procedure. The tissue sample typically is sent to a laboratory for automated analysis or is manually analyzed by a specialist such as a pathologist. To collect a tissue sample, the tubing connecting the medical instrument used to apply suction to the patient to the containment unit is disconnected manually. A separate device is then placed in series with this tubing so as to be located upstream from the containment unit. The tissue sample is captured in the device. The device is then removed and the tubing from the suction applicator is reconnected directly to the containment unit. Repetitive connecting and disconnecting of the tubing during the collection of multiple samples adds additional time to the completion of the surgical procedure. Upon disconnection of the tubing, small amounts of adhered uncontained liquid and semisolid waste in the tubing can be released into the surrounding environment potentially contaminating the floors and other surfaces in the surgical facility.

SUMMARY OF THE INVENTION

This invention is directed to a new and useful system and method for system and method for retrieving tissue samples during medical and surgical procedures such as colonoscopies. The system of this invention includes a mobile unit that to which both a source of irrigating fluid and container for collecting waste is connected. A removable cassette is attached to the mobile unit. In many versions of the invention, the cassette is seated in a receptacle, a structural component of the waste collection unit. The cassette has a fitting for receiving the suction line that extends from the suction applicator. The cassette also has an outlet into the waste collection unit container. A tissue trap is removably mounted to the cassette. The tissue trap is selectively placed in series with the fluid flow that the suction draws through the cassette. The trap includes a filter for trapping tissue that is entrained in the fluid stream drawn into the mobile unit.

In some versions of the invention, the tissue trap is selectively attached to the cassette. In these versions of the invention, when the tissue trap is not mounted to cassette, the fluid stream flows through a first set of conduits internal to the cassette into the container. When it is desirable to remove a tissue specimen from the fluid stream, the tissue trap is temporarily fitted to the cassette. This results in the fluid stream flowing through the trap. The tissue is therefore retained in the trap as the rest of the material entrained in the waste stream flows to the cassette.

In other versions of the invention, the tissue trap, while removably attached to the cassette may be attached to the cassette even when there is no need to collect tissue. In these versions of the invention, one or more valves regulate the path through the cassette through which the waste stream flows. If there is no need to collect tissue, the valve/valves is/are placed in a bypass mode. When the valves are in the bypass mode, the fluid stream is not flowed through the trap. When tissue collection is desired, the valve/valves are set into a tissue collection mode. When the valve/valves are in this mode, the fluid stream is flowed through the tissue trap prior to being discharged into the waste collection canister. The tissue is blocked from downstream flow into the waste collection canister by the filter integral with the trap.

In each version of the invention, once tissue is captured in one trap, another trap can be fitted to the cassette. This makes it possible to, in single procedure, trap plural specimens while only a single cassette is attached to the waste collection unit. Since only a single cassette is employed there is no need to, during the procedure, constantly disconnected the suction tube from and reconnect the suction tube to different cassettes.

BRIEF DESCRIPTION OF THE DRAWINGS

The invention is pointed out with particularity in the claims. The above and further features and advantages of the invention are understood by the following Detailed Description taken in conjunction with the accompanying drawings in which:

FIG. 9A is a rear view of the upper cassette housing with the irrigation coupler in the open position;

FIG. 9B is a top view of the upper cassette housing with the irrigation coupler in the open position;

FIG. 9C is a front view of the upper cassette housing with the irrigation coupler in the open position;

FIG. 9D is a right side view of the upper cassette housing with the irrigation coupler in the open position;

FIG. 9E is a bottom view of the upper cassette housing with the irrigation coupler in the open position;

FIG. 9F is a bottom perspective view of the upper cassette housing with the irrigation coupler in the open position;

FIG. 9G is a top perspective view of the upper cassette housing with the irrigation coupler in the open position;

FIG. 11A is a top view of a tissue trap with the screen in a closed position;

FIG. 11B is a rear view of the tissue trap with the screen in a closed position;

FIG. 11C is a left side view of the tissue trap with the screen in a closed position;

FIG. 12A is a top view of the tissue trap with the screen in an open position;

FIG. 12B is a rear view of the tissue trap with the screen in an open position;

FIG. 12C is a left side view of the tissue trap with the screen in an open position;

FIG. 20A is a perspective view of a valve member;

FIG. 20B is a bottom view of the valve member;

FIG. 20C is a side view of the valve member;

FIG. 20D is a top view of the valve member;

FIG. 21A is a perspective view of a tissue trap;

FIG. 21B is a top view of the tissue trap;

FIG. 21E is a rear view of the tissue trap;

FIG. 21F is a bottom view of the tissue trap;

FIG. 22B is a top view of the tissue trap contained within a specimen container;

FIG. 22C is front view of the tissue trap contained within a specimen container;

FIG. 22D is a cross sectional view of the tissue trap contained within a specimen container as taken along section line 22D-22D in FIG. 22C;

FIG. 23 is a left front exploded view of another embodiment of a manifold assembly;

FIG. 24B is cross sectional view of an actuator and pinch valve;

FIG. 26 is a top exploded perspective view of a cassette;

FIG. 27 is a bottom exploded perspective view of a cassette;

FIG. 28A is a top view of a lower cassette housing;

FIG. 28B is a right side view of the lower cassette housing;

FIG. 28C is a bottom view of the lower cassette housing;

FIG. 30A is a top view of an upper cassette housing;

FIG. 30B is a right side view of the upper cassette housing;

FIG. 30C is a bottom view of the upper cassette housing;

FIG. 31 is an exploded top view of a tissue trap and specimen container;

FIG. 37A is a right front perspective view of the manifold assembly according to one embodiment;

FIG. 37B is a left rear perspective view of the manifold assembly;

FIG. 38A is a front exploded view of the manifold assembly;

FIG. 38B is a cross-sectional view of the manifold assembly;

FIG. 38C is a perspective view of a flapper valve unit;

FIG. 38D is a cross-sectional view of the flapper valve unit;

FIG. 39A is a top view of the manifold assembly with the tissue trap removed;

FIG. 39B is a side view of the manifold assembly with the tissue trap removed;

FIG. 40A is a top view of the cassette cap;

FIG. 40D is a rear view of the cassette cap;

FIG. 41A is a top view of a cassette shell;

FIG. 41B is a front view of the cassette shell;

FIG. 41C is a right side view of the cassette shell;

FIG. 41D is a rear view of the cassette shell;

FIG. 41E is a left side view of the cassette shell;

FIG. 43 is a perspective exploded view of an additional embodiment of a manifold assembly;

FIG. 45B is a front view of the tissue trap of FIG. 44;

FIG. 45C is a right side view of the tissue trap of FIG. 44;

FIG. 45E is a left side view of the tissue trap of FIG. 44;

FIG. 46 is a perspective view of another embodiment of a manifold assembly;

FIG. 49A is a front view of the tissue trap receiver of FIG. 48B;

FIG. 49B is a bottom view of the tissue trap receiver;

FIG. 49C is a side view of the tissue trap receiver;

FIG. 49D is a top view of the tissue trap receiver;

FIG. 49E is a rear side view of the tissue trap receiver;

FIG. 50 is a perspective view of an irrigation cassette assembly;

FIG. 51 is a cross-sectional view of the irrigation cassette assembly mounted in an irrigation receptacle;

FIG. 52 is an exploded perspective view of the irrigation cassette assembly of FIG. 50;

FIG. 53 is another exploded perspective view of the irrigation cassette assembly of FIG. 50;

FIG. 54 is an exploded side view of the irrigation cassette assembly of FIG. 50;

FIG. 55 is a top perspective view of another embodiment of an irrigation cassette assembly;

FIG. 56 is a bottom perspective view of another embodiment of an irrigation cassette assembly;

FIG. 57 is an exploded view of the components forming an additional alternative cassette of this invention;

FIG. 58 is a cross sectional view of the cassette of FIG. 57;

Figure 57:
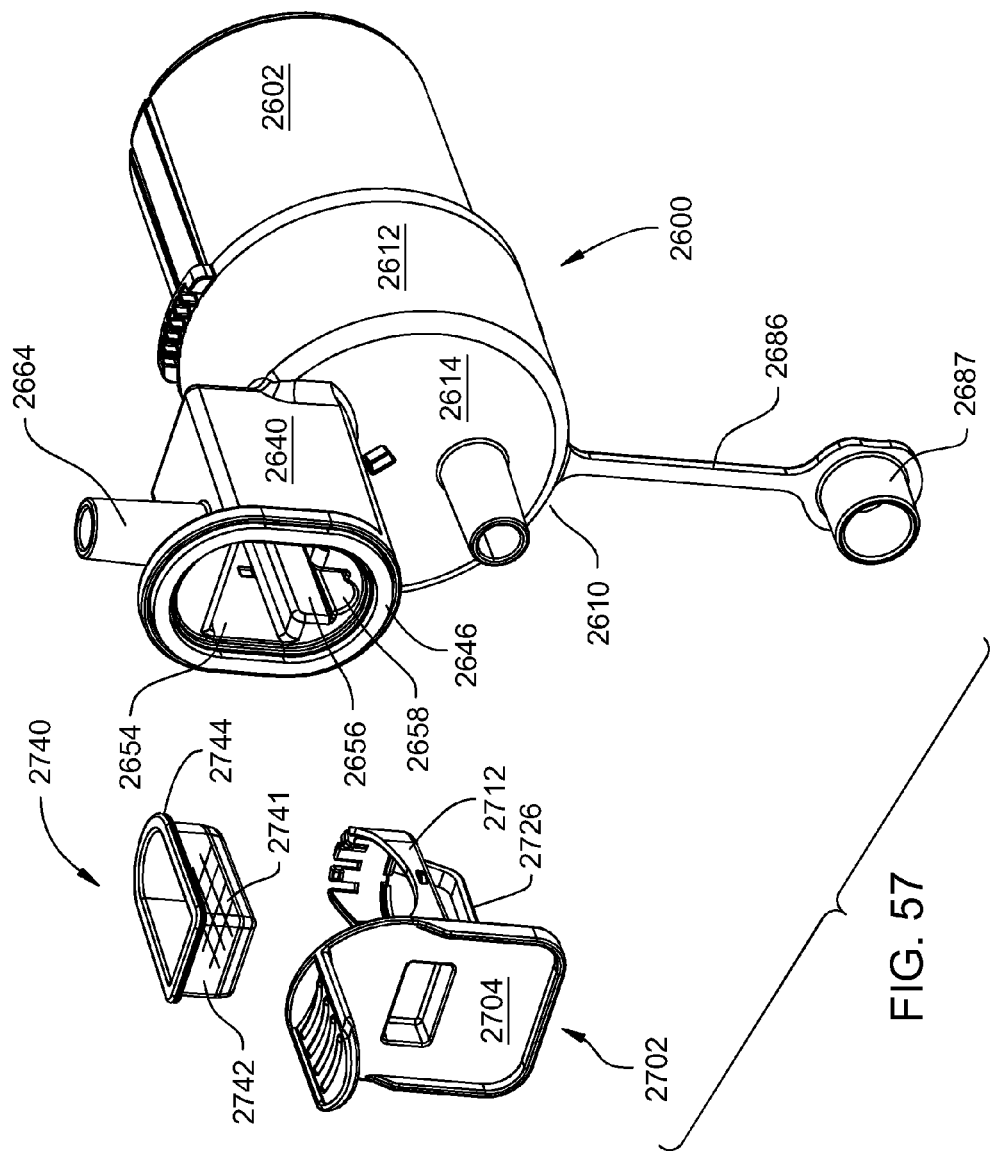
Figure 60:
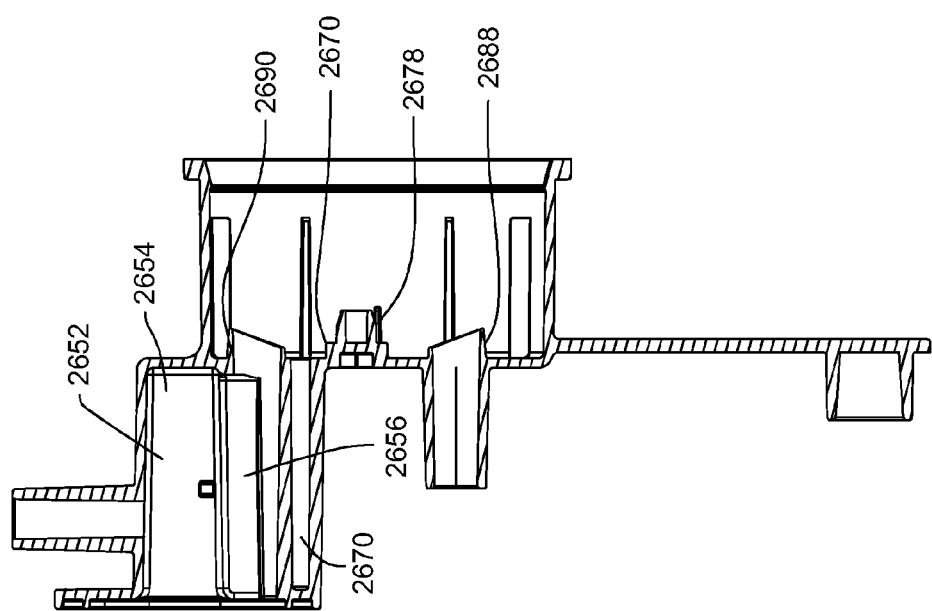
Figure 59:
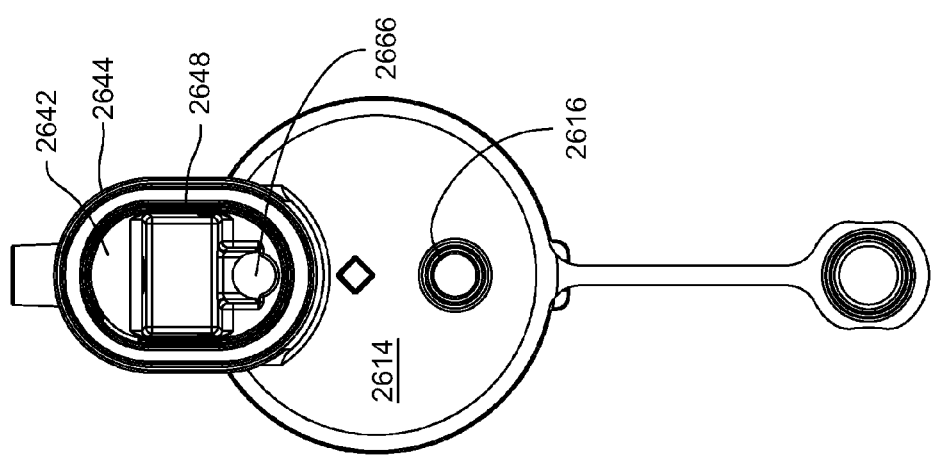

FIG. 59 is a front plane view of the cassette of FIG. 57;

FIG. 60 is a cross sectional view of the cap of the cassette of FIG. 57;

FIGS. 61A and 61B are, respectively front and rear perspective views of the screen holder used with the cassette of FIG. 57; and FIG. 62 is a perspective view of the cassette of FIG. 57 with installed screen holder.

DETAILED DESCRIPTION

I. Overview

Figure 1A:
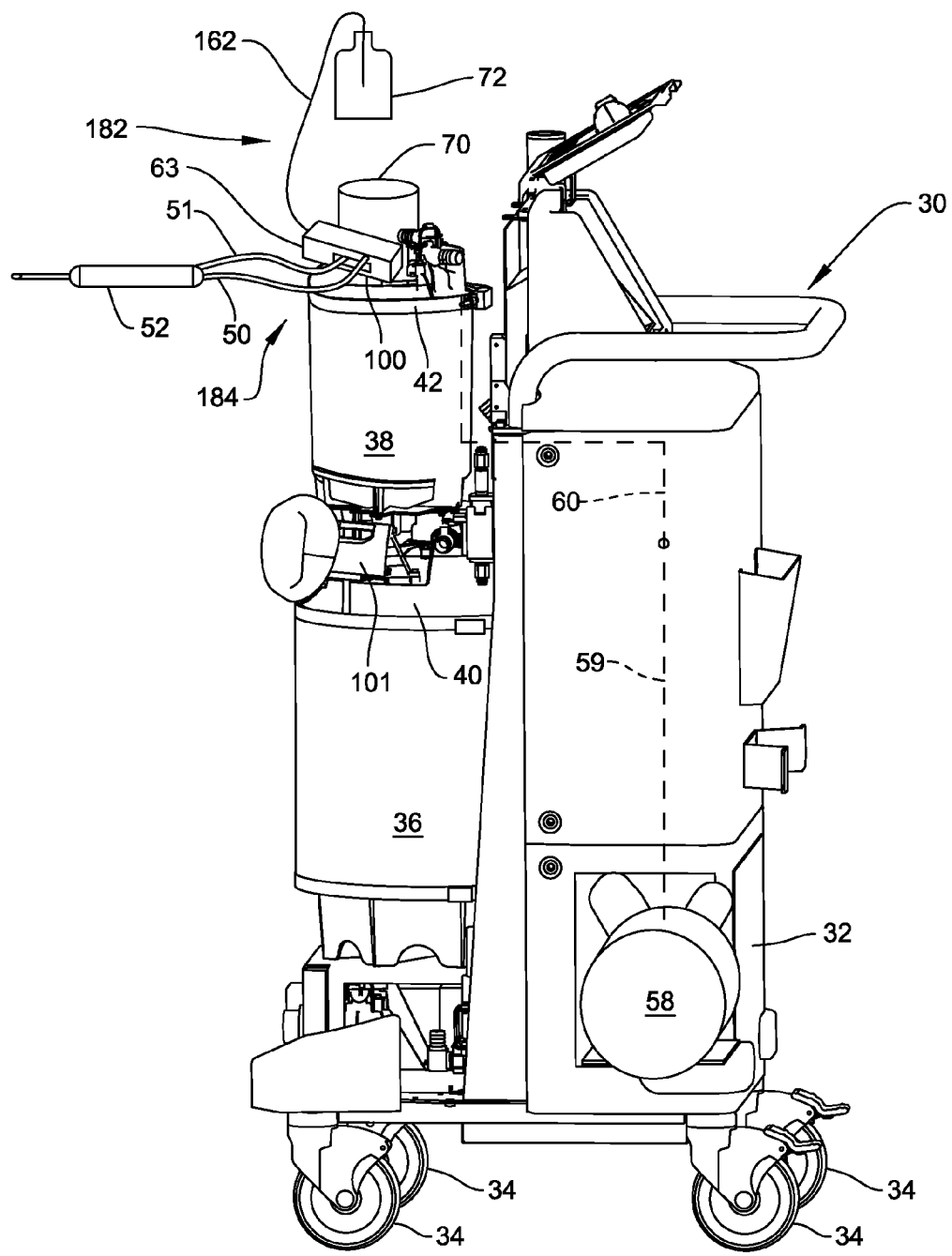
FIG. 1A is a side view of a medical/surgical waste collection system of this invention.

FIG. 1A illustrates a waste and tissue collection system 30 constructed in accordance with this invention. System 30, sometimes referred to as a mobile unit or rover, includes a base 32. The cover and door assemblies that normally conceal the components of mobile unit 30 are not present in FIG. 1A so that these components can be seen. Wheels 34 attached to the bottom of the base 32 provide the system with mobility. Two canisters 36 and 38 are mounted to the base 32. A first one of the canisters, canister 36, has a relatively large interior volume, between approximately 10 and 40 liters. The second canister, canister 38, has a smaller volume, between approximately 1 and 10 liters. Each canister 36 and 38 has a cap 40 and 42, respectively.

Figure 2:
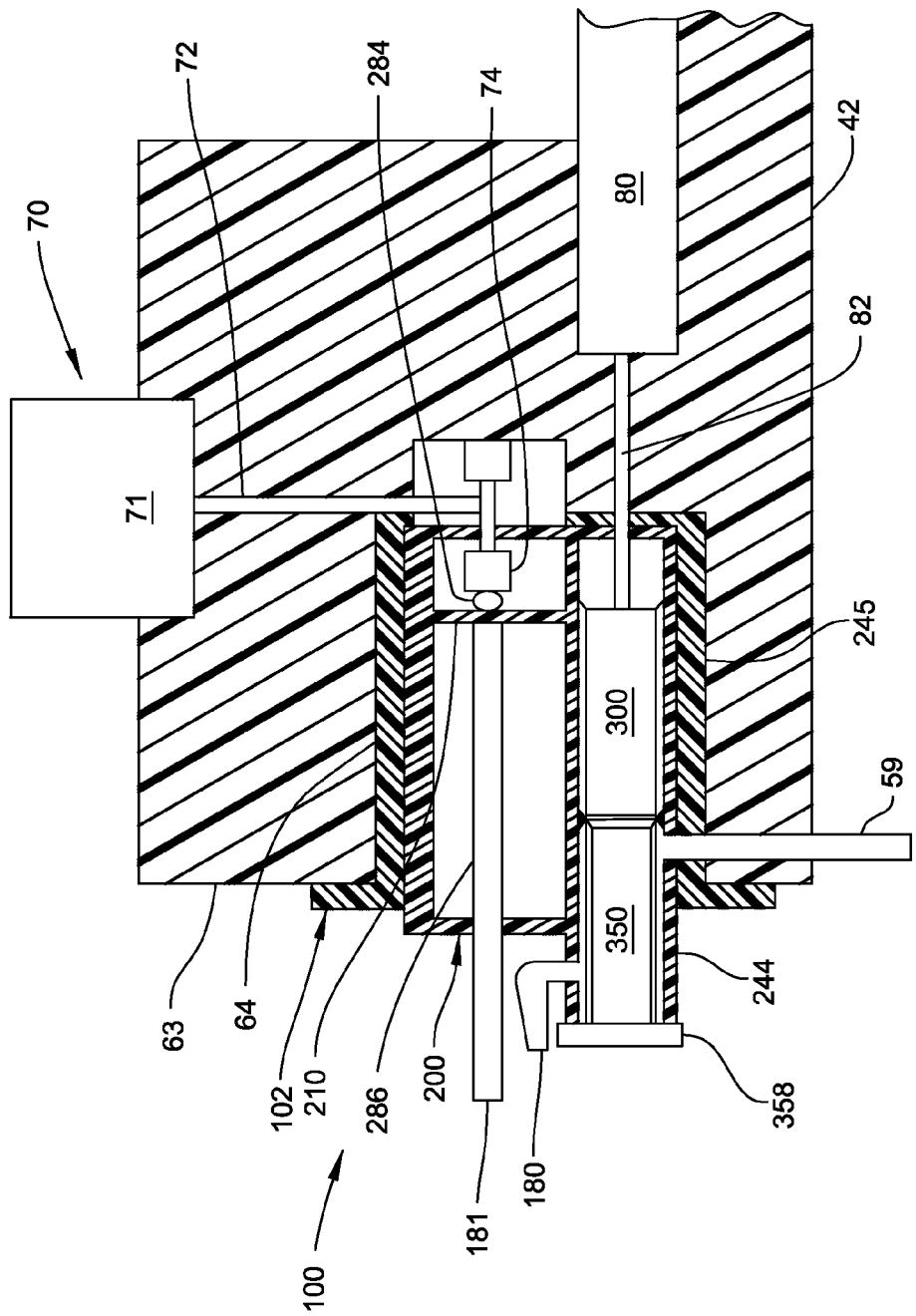
FIG. 2 is a cross sectional view of a manifold assembly mounted in the waste collection system.

With additional reference to FIG. 2, attached to canister cap 42 of canister 38 is a manifold assembly 100. Manifold assembly 100 includes a receptacle 102 and a cassette 200. Cassette 200 is removably seated in receptacle 102. As described below, cassette 200 is formed with a number of fittings 180 and 181. Fitting 180 can receive a suction line 50 and fitting 181 can receive an irrigation line 51. The distal end of each suction line 50 and irrigation line 51 is attached to a suction applicator 52. (Here, "distal", refers to towards the surgical site at which the suction is applied and "proximal" means away from the surgical site.) In FIG. 1A, suction applicator 52 is diagrammatically shown as a hand piece specifically and solely designed to apply suction and irrigation, it should be understood that this is exemplary, not limiting. Sometimes the suction applicator 52 is built into another surgical tool, such as a colonoscope or ablation tool, applied to a surgical site to accomplish a task other than applying suction and irrigation.

Also part of mobile unit 30 is a suction pump 58 and peristaltic pump 70. A duct extends from each cap 40 and 42 to the suction conduit. In FIG. 1A these conduits are depicted as dashed lines 60. These conduits are fluid path through which the suction pump draws a vacuum on the canisters 36 and 38 and, by extension, the suction tubing connected to the canisters. When suction pump 58 is actuated, the resultant suction draws matter into the applicator attached to the suction tube.

A continuous suction fluid communication path 184 is formed from applicator 52 to suction pump 58. The waste stream flows from the receptacle 102 into the associated canister 36. Liquid and small solid bits of matter entrained in this flow stream precipitate out of the stream into the canister 38. This waste is thus stored in the canister 36 until the canister is emptied. Gas and any small bits of matter entrained in this flow stream flow from the canister towards the suction pump 58.

An alternative manifold receptacle 1699 is shown attached to canister 36. Manifold receptacle 1699 is shaped to receive another manifold (not illustrated) not part of the present invention. This particular manifold receptacle and the manifold inserted in it are disclosed in the incorporated by reference U.S. Pat. No. 7,615,037.

As seen in FIG. 2, cap 42 is formed to have a solid cap head 63 that projects upwardly from the top surface of the base of the cap. A cavity 64 is defined in cap head 63. Receptacle 102 is mounted in cavity 64. Receptacle 102 is mounted to cavity 64 with the panels of receptacle 102 in contact with the interior panels of cap head 63. Cassette 200 is removably retained within receptacle 102. Irrigation fitting 180 and suction fitting 181 extend distally away from cassette 200.

Peristaltic pump 70 is coupled with irrigation line 51 such that rotation of peristaltic pump 70 forces irrigation liquid from an irrigation liquid source 72 through irrigation line 162, cassette 200 and irrigation line 51 to applicator 52 where it is supplied to a surgical site. Peristaltic pump 70 comprises a rotary electric motor 71 that is connected by a shaft 72 to eccentric rollers 74. Peristaltic pump 70 supplies irrigation fluid to applicator 52 as will be described later in more detail. A continuous irrigation fluid communication path 182 is formed from irrigation liquid source 72 to applicator 52.

A linear actuator 80 is connected to piston 300 through a connecting rod 82. Linear actuator 80 can cause rod 82 to move in reciprocating motion toward and away from piston 300. Piston 300 is shown located toward a sleeve distal end 245 and tissue trap 350 is shown located toward a sleeve proximal end 244.

Figure 1B:
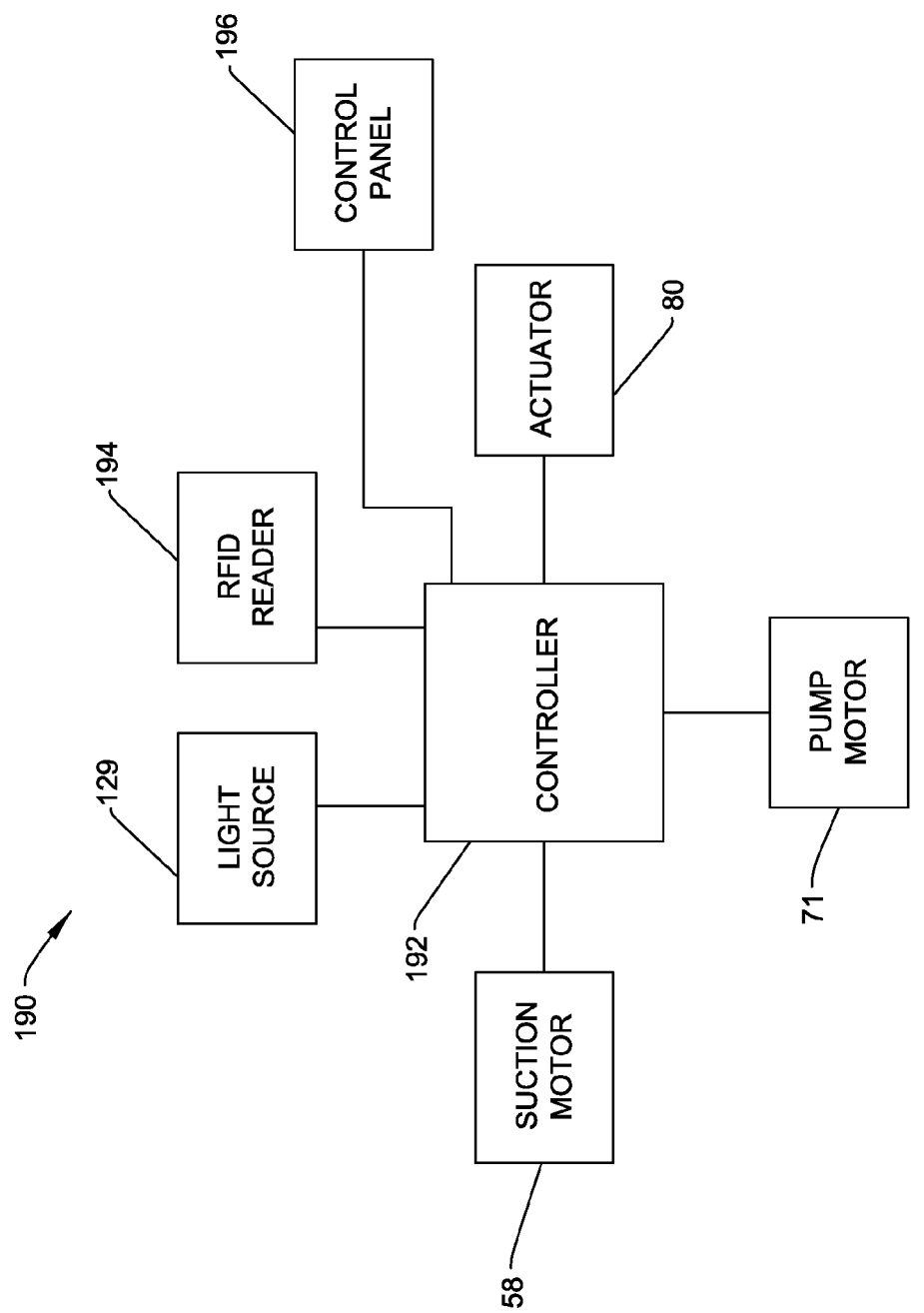
FIG. 1B is a schematic view of a control system for controlling the operation of the medical/surgical waste collection system of FIG. 1A.

FIG. 1B illustrates a control system 190 for controlling the operation of waste collection system 30. Control system 190 is mounted within waste collection system 30. Control system 190 includes a controller 192. Controller 192 can be a general purpose micro-processor or micro-controller or a computer. Controller 192 is in communication with and controls the operation of suction motor 58, pump motor 71, actuator 80, light source 129, radio frequency identification (RFID) reader 194, and control panel 196. Control panel 196 includes buttons, switches and displays to allow a user to select, control and view operational parameters of waste collection system 30.

Figure 1C:
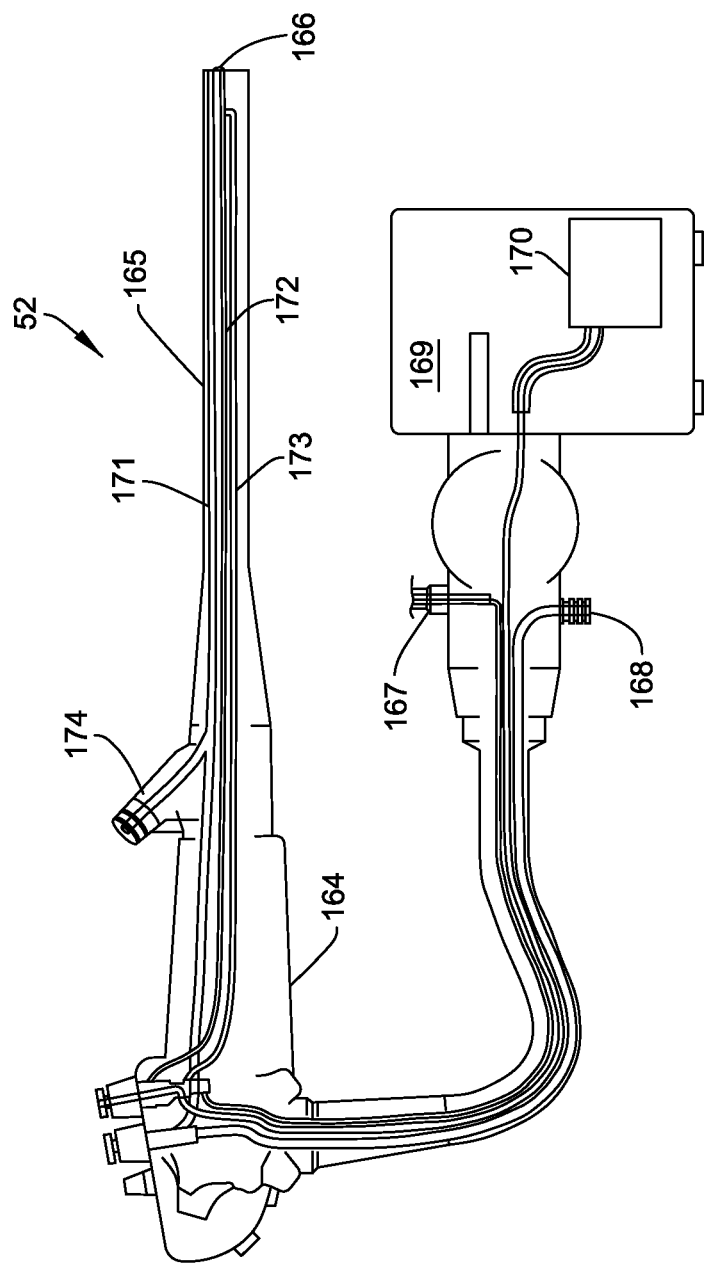
FIG. 1C is a cross sectional view of a colonoscope.

FIG. 1C illustrates details of one suction applicator 52, specifically a colonoscope 52 for performing colonoscopies. Colonoscope 52 has a handgrip 164 that is connected to an elongated flexible tube 165 with an end 166. Handgrip 164 is connected to an irrigation fluid connection 167, a suction connection 168, a light source 169 and an air pump 170. Flexible tube 165 contains a suction channel 171, an air channel 172, a water channel 173 and biopsy valve 174. Irrigation fluid connection 167 is connected with irrigation line 51 (FIG. 1A) and suction connection 168 is connected to suction line 50 (FIG. 1A). End 166 is placed at a surgical site and suction, air or irrigation fluid are applied to the surgical site through end 166. A polyp sample can be collected or retrieved from a gastrointestinal tract using colonoscope 52. A cutting tool (not shown) is inserted through biopsy valve 174 and suction channel 171 to the surgical site. The cutting tool can resect and remove a polyp. The cutting tool is removed from suction channel 171 and the polyp is extracted from the resection site by the suction drawn through suction channel 171.

II. First Embodiment

A. Receptacle

Turning to FIGS. 3-6, manifold assembly 100 of the first embodiment of this invention is illustrated. Manifold assembly 100 comprises a receptacle 102, cassette 200, piston 300 and tissue trap 350.

Receptacle 102 is shown generally rectangular in shape. Other shapes such as round, oval or square can be utilized. Receptacle 102 is defined by six exterior panels including parallel and spaced apart generally horizontally oriented top and bottom panels 105 and 106; parallel and spaced apart generally vertically oriented panels 107 and 108; and parallel and spaced apart generally vertically oriented front panel 109 and partial back or rear panel 110. A flange 112 extends peripherally and perpendicularly outward from panels 105, 107 and 108. Flange 112 has a rear surface 114. Receptacle 102 can be formed from any suitable material such as injection molded plastic.

The front panel 109 defines a horizontally oriented opening 118 including a narrow region 119 and a wide region 120. The opening 118 extends across the width of receptacle 102 and extends through receptacle 102 between front panel 109 and rear panel 110. A panel 117 extends perpendicularly away from bottom panel 106 and adjoins bottom panel 116 to define the wide region opening 120. Bottom panel 116 extends between panels 107 and 117 and is generally parallel with panel 106. Wide region 120 is defined by panels 105, 107, 116 and 117. Wide region 120 is unitary with narrow region 119.

A generally rectangular shaped door opening 124 is defined in the top panel 105 adjacent the edge of the receptacle and adjoining side panel 107. A generally rectangular shaped irrigation opening 126 (FIG. 6) is defined in the bottom panel 106 adjacent the edge of the receptacle 102 and adjoining side panel 108. A light hole 128 (FIG. 6) is defined in side panel 107 adjacent to flange 112. A light source such as a light emitting diode 129 is mounted in light hole 128 in order to illuminate piston 300 and tissue trap 350. Light emitting diode 129 is connected with a source of electrical power (not shown) mounted in cap 42. An aperture or port 130 (FIG. 5) is defined in bottom panel 116 and positioned toward front panel 109.

Figure 3:
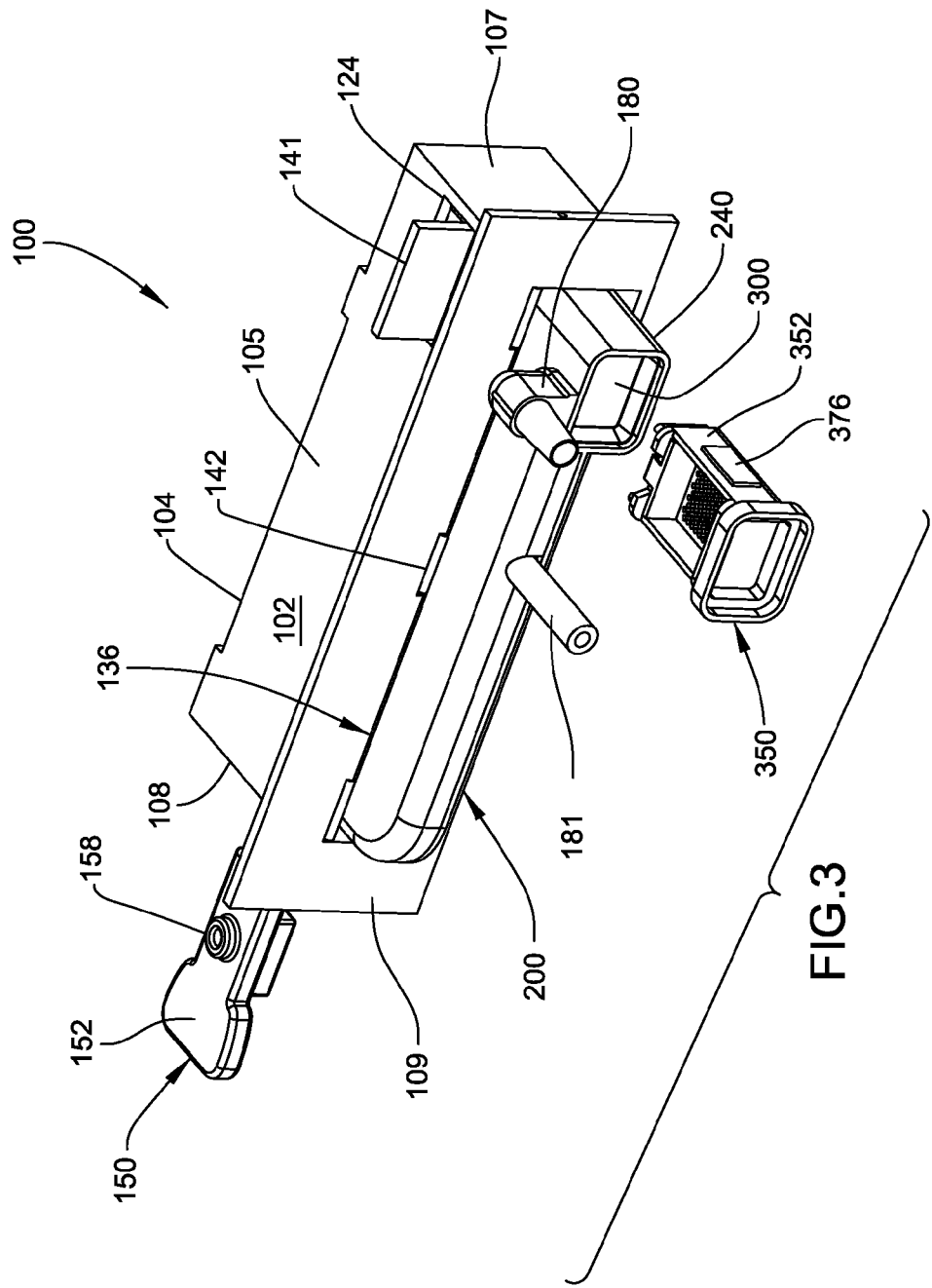
FIG. 3 is a right front perspective view of the manifold assembly according to one embodiment.
Figure 4:
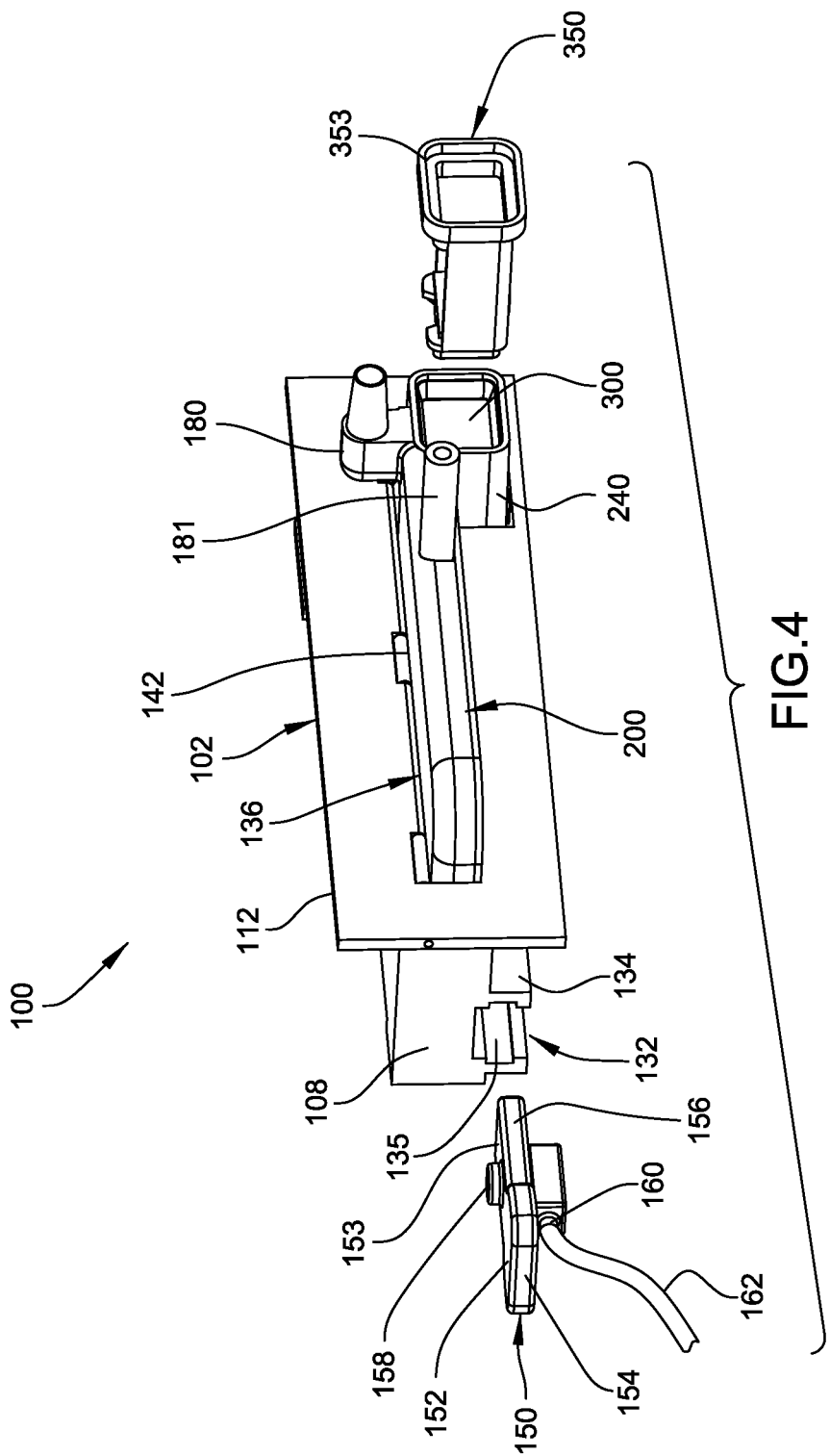
FIG. 4 is a left front perspective view of the manifold assembly.
Figure 5:
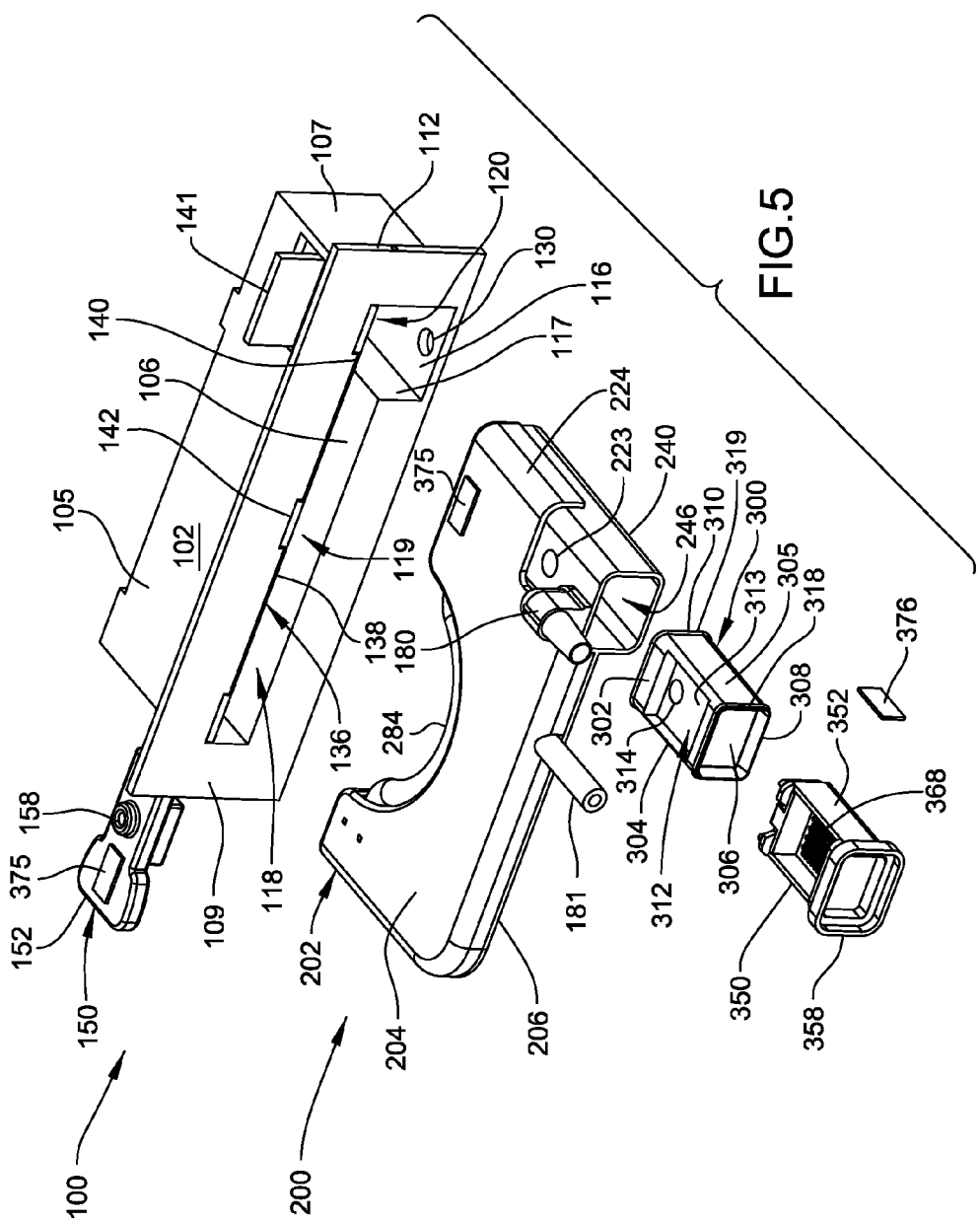
FIG. 5 is a front exploded view of the manifold assembly.
Figure 6:
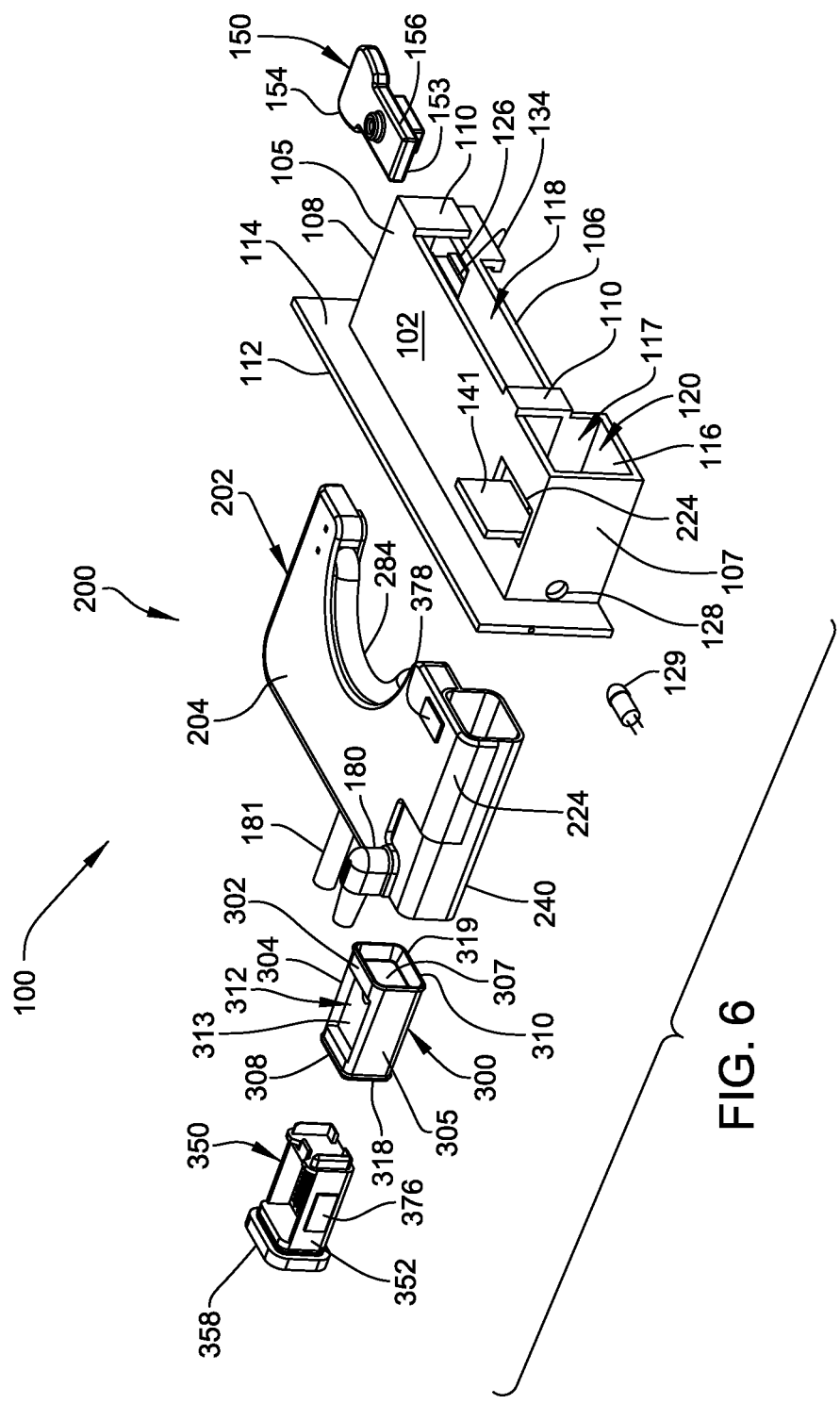
FIG. 6 is a rear exploded view of the manifold assembly.

An elongated door 136 is rotatably mounted to top panel 105 via one or more hinges 142. In FIGS. 4 and 5, only the top edge of door 136 is illustrated. Door 136 includes a top edge 138 and a wide section 140 that has an attached foot 141. Foot 141 extends perpendicularly away from the bottom of door 136 into wide region 120 of opening 118. Door 136 rotates about hinges 142 between an open position, shown in FIGS. 3-5, and a closed position, shown in FIG. 16, in which door 136 covers opening 118 including both narrow region 119 and wide region 120. In the closed position, foot 141 is positioned over suction aperture 130 thereby sealing or closing the path to canister 38. When door 136 is in the open position, foot 141 extends through door opening 124. Hinge 142 biases door 136 into a normally closed position when cassette 200 is removed from or not mounted in passage 118.

A pair of parallel diametrically opposed elongated L-shaped rails 134 (best seen in FIG. 4) extend away from bottom panel 106 below irrigation opening 126. Rails 134 define a slot 132 there between that extends from panel 108 inwardly along and below irrigation opening 126. Parallel and diametrically opposed elongated grooves 135 are defined along the length of each rail 134.

With reference to FIG. 4, irrigation coupler 150 provides an irrigation fluid connection between irrigation line 162 (FIG. 1A) and cassette 200. Irrigation coupler 150 has a generally rectangular shaped body 152 with a distal end 153, a wider integral proximal handle 154 and a pair of parallel opposed beveled elongated sides 156 located on opposite sides of body 152. An outlet fitting 158 formed from compressible material extends upwardly from body 152 and an inlet port 160 extends below body 152 towards proximal handle 154. Inlet port 160 has a barbed end (not shown) for retention of irrigation line 162. A fluid communication path extends through body 152 between outlet fitting 158 and inlet port 160. Irrigation line 162 is connected between inlet port 160 and the source of irrigation fluid 72. Irrigation coupler 150 can be formed from any suitable material such as injection molded plastic.

Irrigation coupler 150 is inserted into and removed from slot 132. A user can insert the irrigation coupler 150 by grasping handle 154 and guiding distal end 153 towards slot 132 such that beveled sides 156 engage grooves 135. Continued pushing of handle 154 towards receptacle 102 with manual force causes beveled sides 156 to slide along grooves 135 until the irrigation coupler 150 is fully seated within slot 132 when handle 154 contacts rails 134. Irrigation coupler 150 can be removed by a user grasping handle 154 and pulling the irrigation coupler 150 away from slot 132.

An identification device 376 (FIG. 5) is attached to irrigation coupler 150. Identification device 376 can be any suitable identification device such as a radio frequency identification (RFID) tag or device, a bar code, a magnetic strip or other memory device. The identification device can contain information such as set-up information, expiration information and controls for re-use or reprocessing.

B. Cassette

Figure 7:
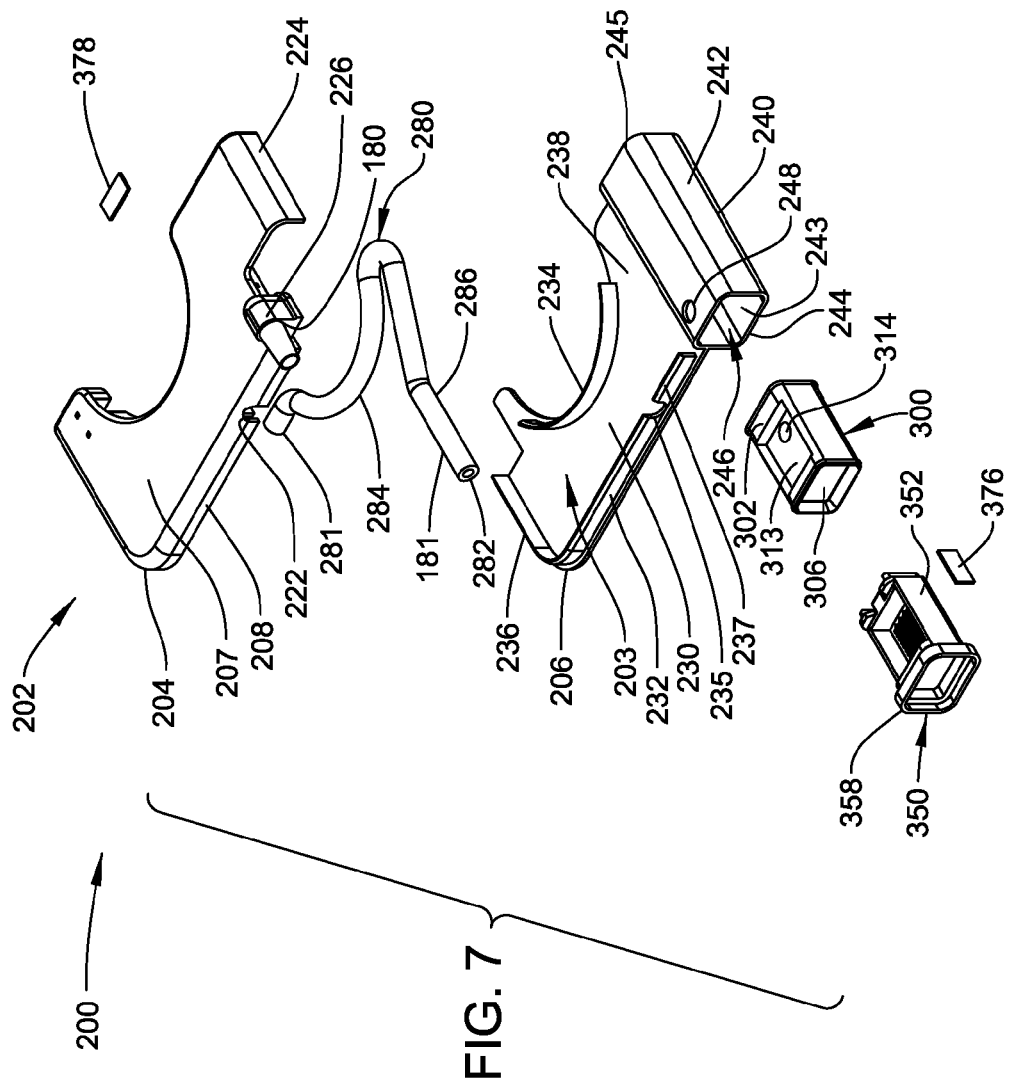
FIG. 7 is a top exploded view of a cassette.
Figure 8:
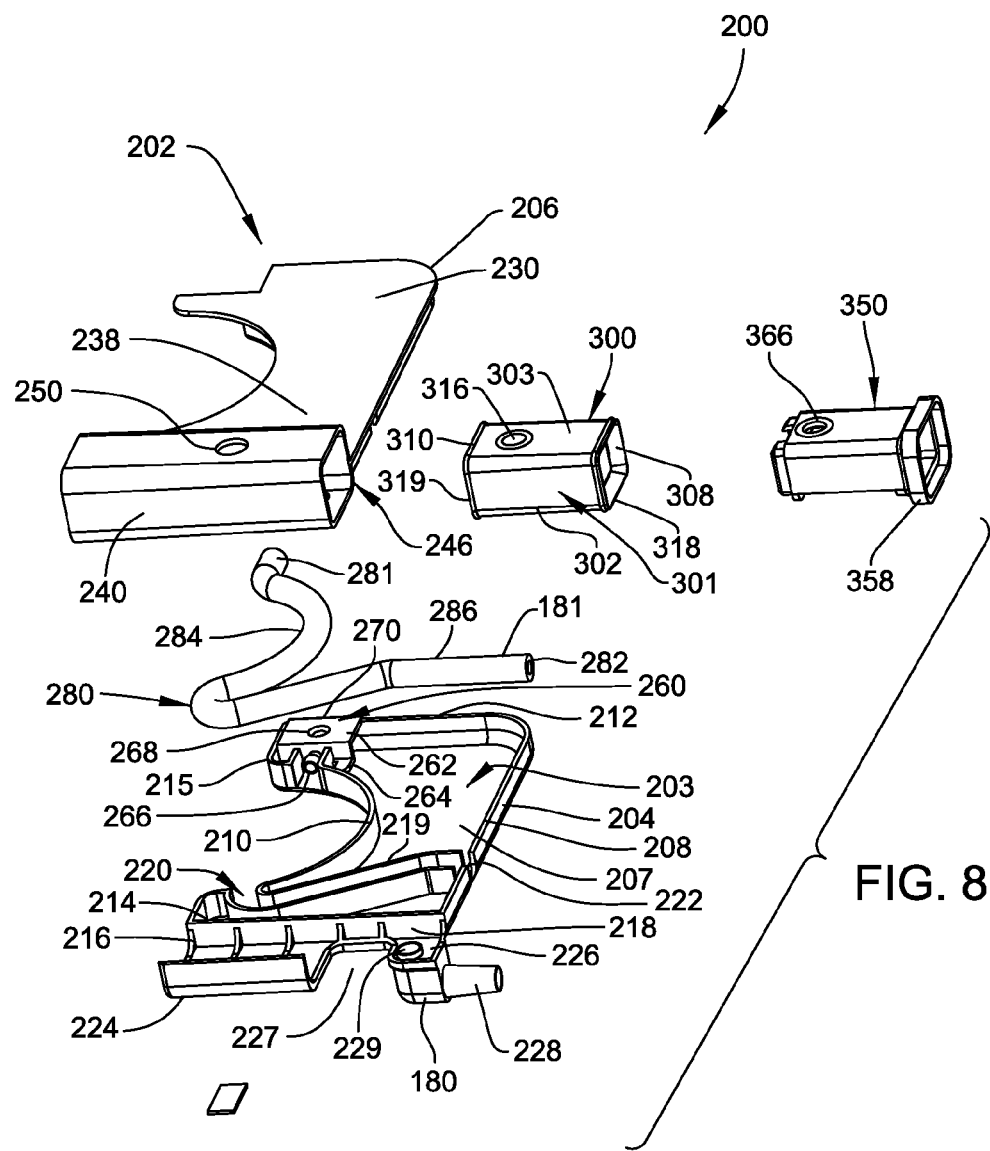
FIG. 8 is a bottom exploded view of the cassette.

FIGS. 7-8, 9A-9G and 10A-10G illustrate details of cassette 200. Cassette 200 can be formed from any suitable material such as injection molded plastic. With specific reference to FIGS. 7-8, cassette 200 is generally rectangular in shape and comprises a housing 202 that has two pieces, an upper housing 204 and an opposed lower housing 206. While the housing is illustrated using two pieces, it is contemplated that housing 202 can be formed as a single unitary part. Upper housing 204 and lower housing 206 are mated together to form housing 202. A cavity 203 is defined within housing 202 between upper housing 204 and lower housing 206. Upper housing 204 includes a planar top panel 207, front panel 208, curved back panel 210, and side panels 212, 214 and 215. Panels 208, 210, 212, 214 and 215 extend perpendicularly away from top panel 207.

A pair of interior support panels, 218 and 219 extend between front panel 208 and back panel 210. Interior support panels 218 and 219 are generally parallel to each other and extend perpendicularly away from top panel 207. Interior support panels 218 and 219 define an irrigation tubing channel 220. An opening 222 in front panel 210 opens into tubing channel 220. A cover 224 extends away from side panel 214 and is co-planar with top panel 207. Cover 224 is mechanically supported by several ribs 216 that extend between side panel 214 and cover 224. An arm 226 extends away from side panel 214 adjacent rear panel 208 and is co-planar with top panel 207. Slot 227 is defined between cover 224 and arm 226.

Suction fitting 180 is a ninety degree elbow fitting that provides a fluid communication path and is mounted to arm 226. Suction fitting 180 has a tapered end 228 to which a suction line 50 (FIG. 1A) is attached and removed and another end 229. End 229 extends slightly away from arm 226. Tapered end 228 is oriented facing away from the front of cassette 200 and end 229 is oriented facing toward lower housing 206. Upper housing 204 further includes an irrigation connector 260 (FIG. 8) that is located within a corner of cassette 200 adjacent panels 212 and 215. With additional reference to FIGS. 9A-9G and 10A-10G, irrigation connector 260 has a generally L-shaped body 262 with a pair of spaced apart flexible feet 264 that extend from body 262 and rest on panel 207. Irrigation connector 260 has a tapered outlet end or port 266 and a recessed chamfered inlet end or port 268. Outlet end or port 266 is located between a portion of panels 210 and 215. Irrigation connector 260 makes a ninety degree bend or elbow and defines a fluid communication path for irrigation liquid between inlet port 268 and outlet port 266. Body 262 is attached to panel 212 through a living hinge 270. A living hinge is a thin flexible hinge or flexure bearing that is formed as a unitary piece between two components that are desired to be moved relative to each other. Feet 264 provide a spring force to body 262 that biases body 262 away from panel 207.

Figure 10A:
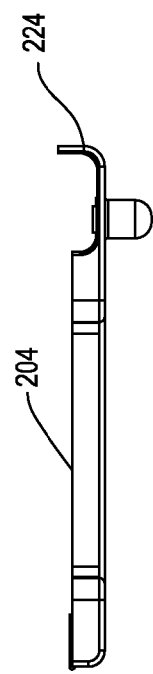
FIG. 10A is a rear view of the upper cassette housing with the irrigation coupler in the closed position.
Figure 10B:
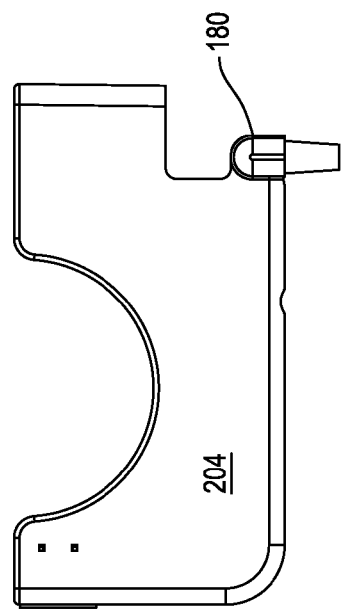
FIG. 10B is a top view of the upper cassette housing with the irrigation coupler in the closed position.
Figure 10C:
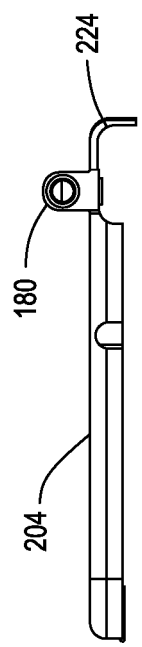
FIG. 10C is a front view of the upper cassette housing with the irrigation coupler in the closed position.
Figure 10D:
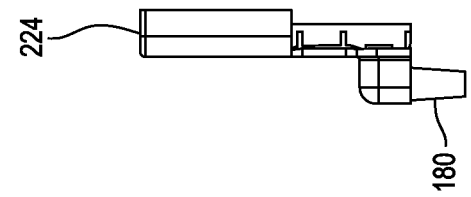
FIG. 10D is a right side view of the upper cassette housing with the irrigation coupler in the closed position.
Figure 10E:
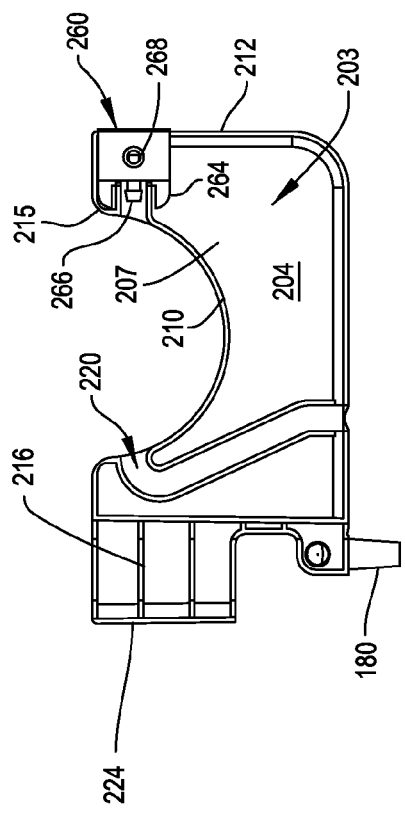
FIG. 10E is a bottom view of the upper cassette housing with the irrigation coupler in the closed position.
Figure 10G:
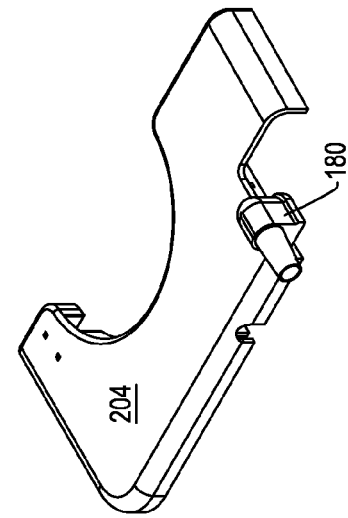
FIG. 10G is a top perspective view of the upper cassette housing with the irrigation coupler in the closed position.
Figure 10F:
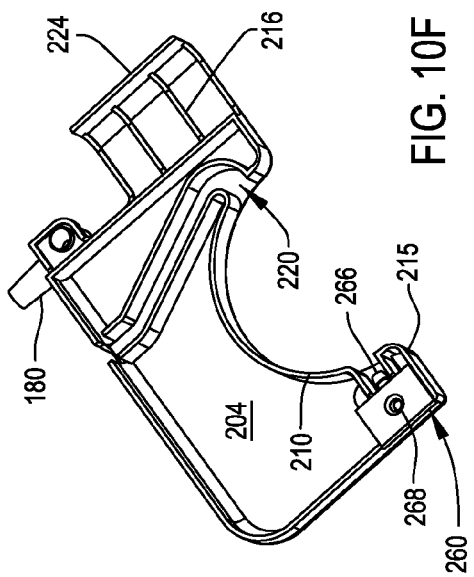
FIG. 10F is a bottom perspective view of the upper cassette housing with the irrigation coupler in the closed position.
Figure 11D:
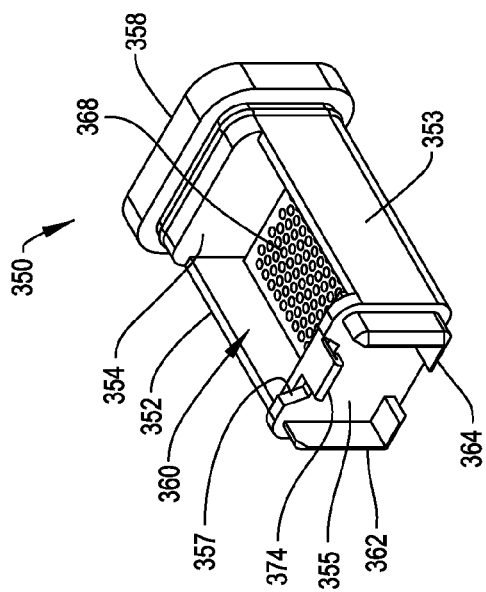
FIG. 11D is a rear perspective view of the tissue trap with the screen in a closed position.
Figure 11E:
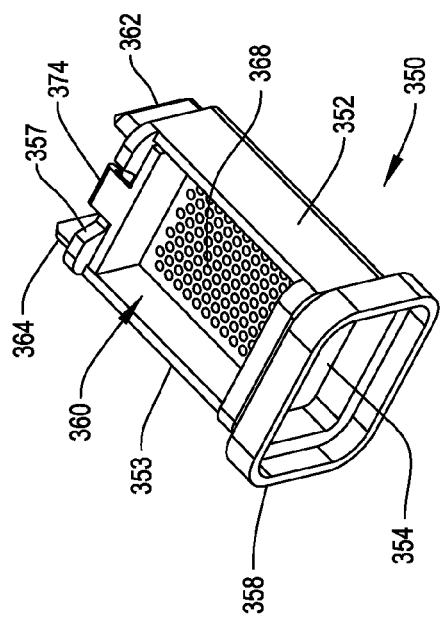
FIG. 11E is a front perspective view of the tissue trap with the screen in a closed position.
Figure 12D:
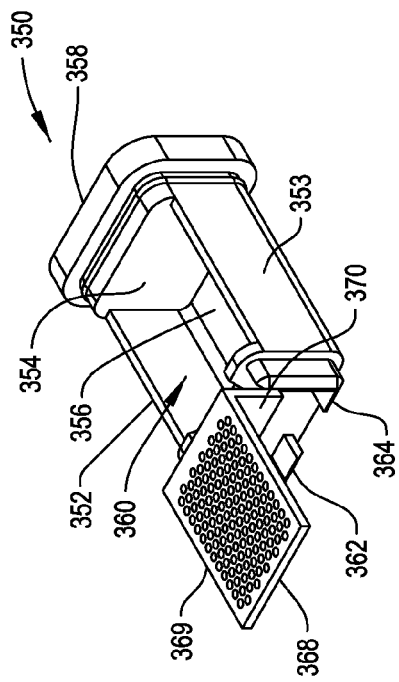
FIG. 12D is a rear perspective view of the tissue trap with the screen in an open position.
Figure 12E:
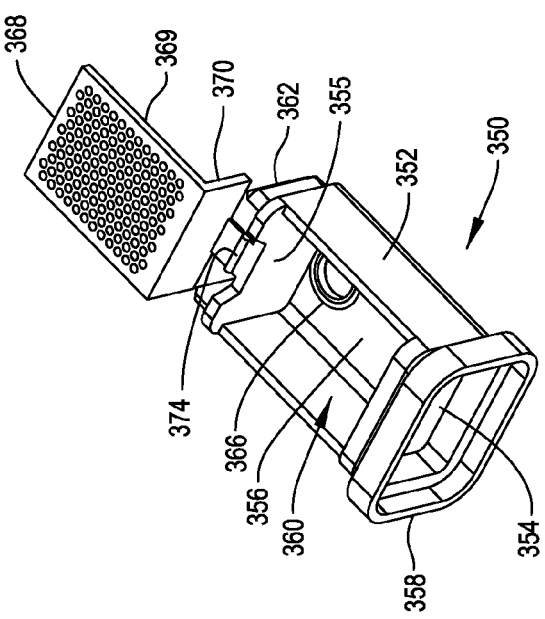
FIG. 12E is a front perspective view of the tissue trap with the screen in an open position.

Upper housing 204 is formed or molded with irrigation connector 260 extending distally away from side 212 (FIG. 9E). In this position, irrigation connector 260 is located outside of upper housing 204. Body 260 can be rotated about living hinge 270 into cavity 203 such that feet 264 rest on top panel 207 with outlet port 266 located between a portion of panels 210 and 215 (FIG. 10E). In this position, irrigation connector 260 is located inside of upper housing 204.

Turning back to FIGS. 7 and 8, lower housing 206 includes a planar bottom panel 230, front panel 232, curved back panel 234, and side panel 236. Panels 232, 234 and 236 extend perpendicularly away from bottom panel 230 and each have a beveled edge 237. A U-shaped opening 235 is located in front panel 232 to allow irrigation tubing end 282 to pass there through. A generally elongated hollow squared shaped cassette sleeve 240 extends outwardly from the bottom panel 230 at end 238.

Sleeve 240 has an outer surface 242, an inner surface 243, proximal end 244, distal end 245 and a bore 246. Bore 246 extends entirely through sleeve 240 between proximal and distal ends 244 and 246. A suction aperture 248 is defined in one side of sleeve 240 toward proximal end 244. A cassette discharge port 250 is defined in an opposing side of sleeve 240 toward the center of sleeve 240.

Lower housing 206 further includes a lens 223 (FIG. 5) that is mounted in the top side of sleeve 240. Lens 223 is a magnifying lens that can magnify the contents of tissue trap 350. A user can view any tissue samples collected in tissue trap 350 through lens 223. Pump tube 280 includes an irrigation tube 181, ends 281 and 282, a curved roller contact section 284 and an angled section 286. After assembling pump tube 280 to lower housing 204, angled section 284 is disposed in cassette 200, in channel 220. Pump tube 280 can be formed from any suitable material such as an elastomer or silicone rubber. End 281 is press fit over tapered outlet end or port 266 of irrigation connector 260. Curved roller contact section 284 is positioned adjacent to and extends along the outer surface of curved panel 210. Angled section 286 is positioned and retained within irrigation tube channel 220 between panels 218 and 219. Pump tube 280 further extends from angled section 286 through openings 222 and 235 to end 282. Pump tube 280 provides a fluid communication path for irrigation liquid to flow from outlet port 266 to irrigation fitting 181.

Upper housing 204 and lower housing 206 are mated together to form cassette 200. Housings 204 and 206 are retained to each other by press-fitting, snap fitting or welding the two housing sections together. Other retention means such as adhesives can also be used. When housings 204 and 206 are pressed together to mate, beveled edges 237 force panels 232, 234 and 236 to be seated inwardly of panels 208, 210 and 212, respectively. In the mated position, cover 224 extends over a portion of sleeve 240 toward distal end 245. Also in the mated position, arm 226 extends over a portion of sleeve 240 toward proximal end 244 with end 229 of suction fitting 180 fitting into or received into suction aperture 248.

With additional reference to FIG. 5, piston 300 is shown to have a generally rectangular shape. Other shapes such as round, oval or square can be utilized. Piston 300 is defined by six exterior surfaces including parallel and spaced apart generally horizontally oriented top and bottom surfaces 302 and 303; parallel and spaced apart generally vertically oriented surfaces 304 and 305; and parallel and spaced apart generally vertically oriented front and rear surfaces 306 and 307. Chamber 301 is defined within piston 300. A raised rim 308 extends at an angle peripherally outward from the front panel 306 and from surfaces 302, 303, 304 and 305. Another raised rim 310 extends at an angle peripherally outward from the rear panel 307 and from surfaces 302, 303, 304 and 305.

Piston 300 has a proximal end 318 and a distal end 319 that faces toward bore 246. A generally rectangular recess 312 is defined toward the center of top surface 302. The bottom of recess 312 is defined by shelf 313. An aperture 314 is located in shelf 313 toward distal end 319. Aperture 314 extends through piston 300 between shelf 313 and bottom surface 304. An opening 316 (FIG. 8) is located in bottom surface 303 toward distal end 319. Opening 316 is coaxial with aperture 314. Piston 300 is adapted to be received by bore 246 of sleeve 240. Piston 300 can slide along inner surface 243 with raised rims 308 and 310 in contact with inner surface 243. Piston 300 can be formed from any suitable material such as injection molded elastomer. Piston 300 forms a seal between raised rims 308 and 310 and inner surface 243.

With reference to FIGS. 11A-11E and 12A-12E, the tissue trap 350 is shown. Tissue trap 350 is generally rectangular in shape. Other shapes such as round, oval or square can be utilized. Tissue trap 350 can be formed from any suitable material such as low durometer plastic or thermoplastic elastomer. Tissue trap 350 is defined by five exterior panels including parallel and spaced apart generally vertically oriented panels 352 and 353; parallel and spaced apart generally vertically oriented front and rear panels 354 and 355; and a horizontally oriented bottom panel 356. Notch 357 is defined in panel 355. A flange 358 extends peripherally outward from the front panel 354 and from panels 352, 353, 354 and 356. Tissue trap 350 defines a cavity 360

A pair of diametrically opposed spaced apart centering features 362 and 364 extend distally away from side or end 355. Centering feature 362 is located toward side or end 353 and centering feature 364 is located toward side or end 352. Centering features 362 and 364 guide tissue trap 350 during insertion into bore 246 (FIG. 7) of sleeve 240. An aperture 366 is defined in bottom panel 356 adjacent to the interior of panel 355. Aperture 366 is in fluid communication with cavity 360.

An L-shaped screen 368 is rotatably coupled to tissue trap 350 by a living hinge 374. Screen 368 has a rectangular bottom section 369 and a rectangular side section 370. Bottom section 369 is oriented perpendicular to side section 370. A number of holes 372 are defined through bottom section 369. Screen 368 can be rotated about hinge 374 between a closed position within cavity 360 as shown in FIGS. 11A-11E and an open position outside of cavity 360 as shown in FIGS. 12A-12E.

An identification device 376 (best seen in FIGS. 3 and 6) is attached to side 352 of tissue trap 350. Identification device 376 can be any suitable identification device such as a radio frequency identification (RFID) tag or device, a bar code, a magnetic strip or other memory device. The identification device can contain information such as set-up information, expiration information and controls for re-use or reprocessing.

Another identification device 378 (best seen in FIGS. 5 and 6) is attached to cover 224 of cassette 200. Identification device 378 can be any suitable identification device such as a radio frequency identification (RFID) device, a bar code, a magnetic strip or other memory device. The identification device can contain information such as set-up information, expiration information and controls for re-use or reprocessing.

Figure 13:
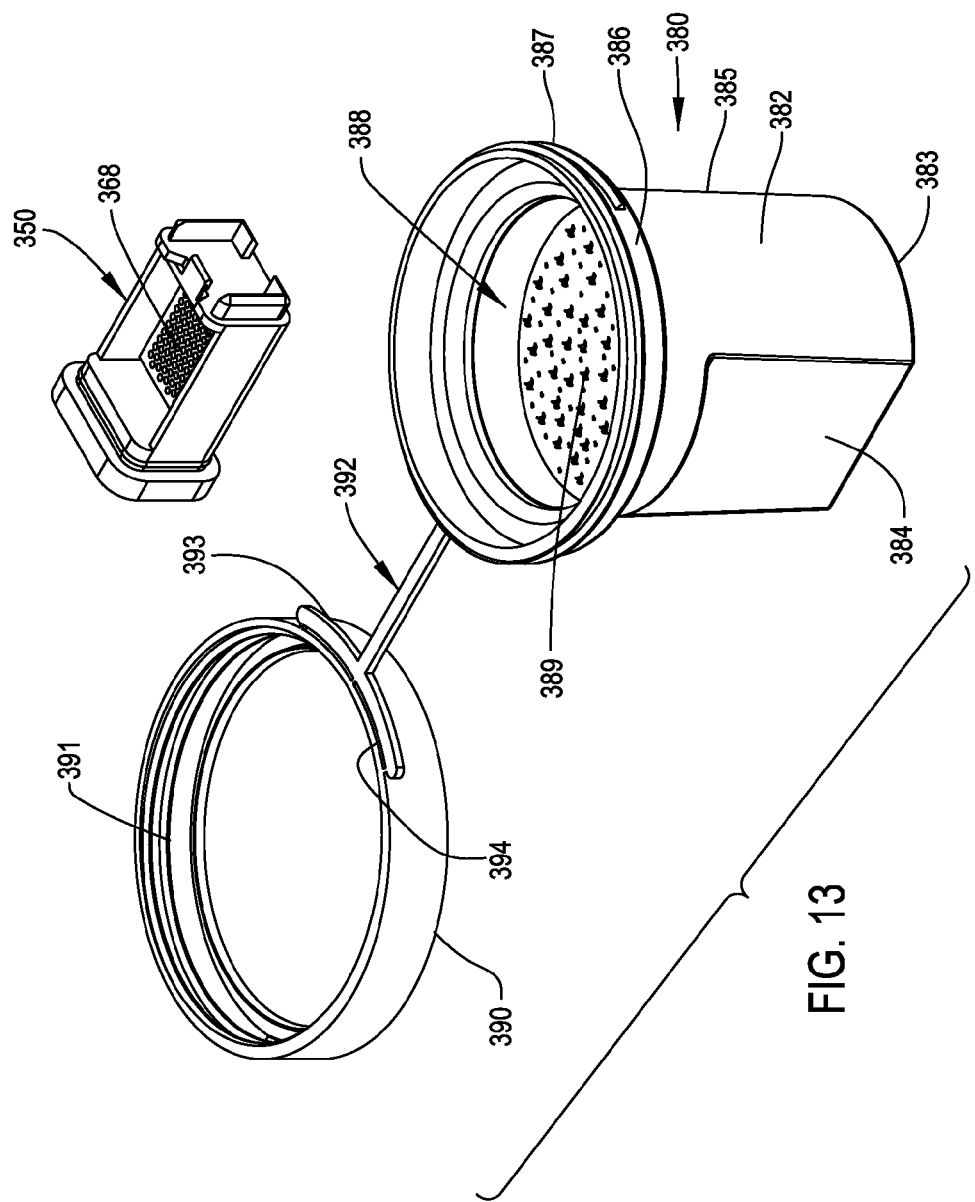
FIG. 13 is a perspective view of a specimen container and the tissue trap.
Figure 14:
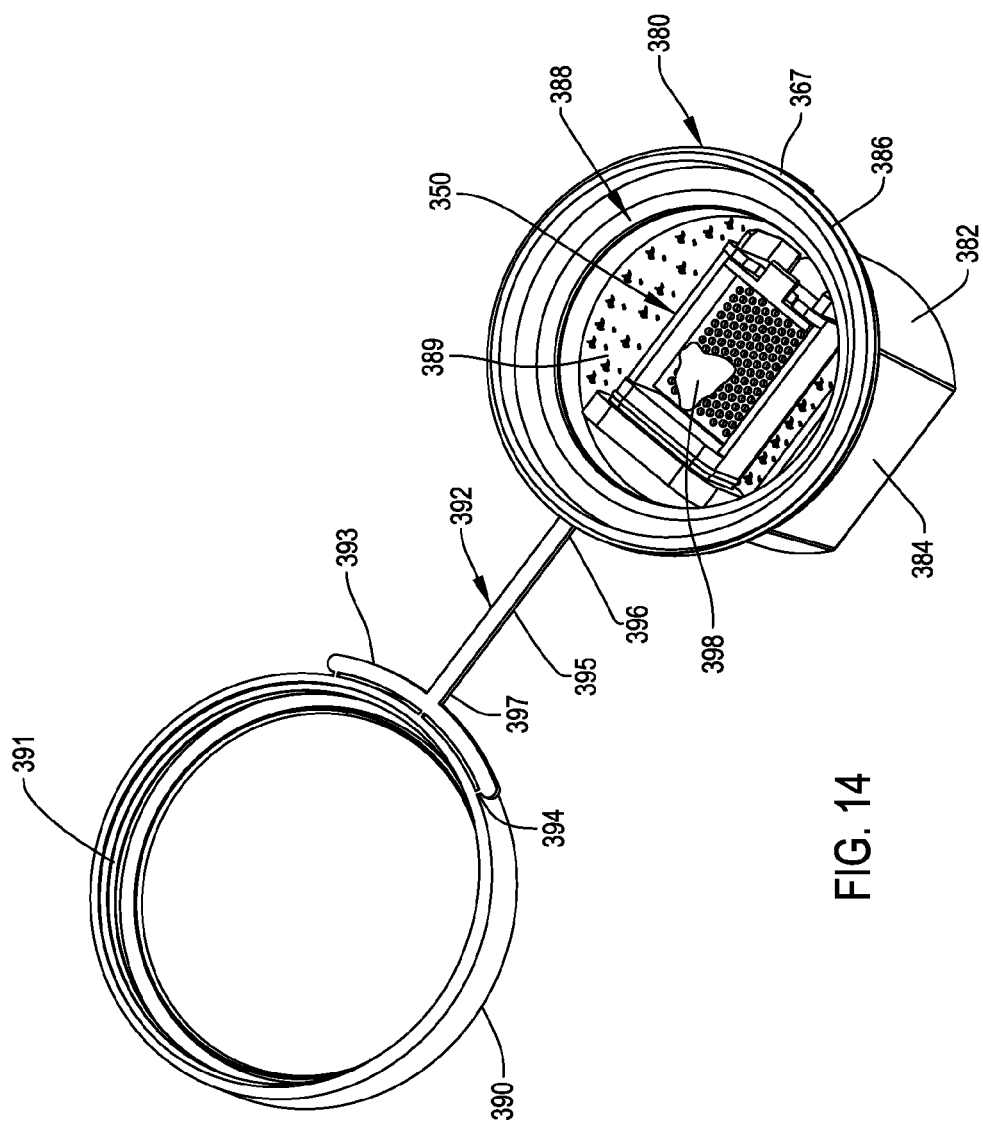
FIG. 14 is a perspective view of the tissue trap contained within the specimen container.

FIGS. 13 and 14 illustrate a specimen container or jar 380. Specimen container or jar 380 has a generally cylindrical shape with an outer panel 382, a bottom panel 383. Two planar diametrically opposed spaced apart grasping sections 384 are located in outer panel 382 of specimen container 380. A compartment 388 is defined within specimen container 380. In one embodiment, compartment 388 contains a preservative solution 389 such as formalin or other suitable preservative solution. In another embodiment, the preservative solution is omitted. Specimen container 380 is formed from a transparent material such that the contents of compartment 388 may be viewed by a user.

An annular flange 386 extends peripherally upward and outward from panel 382. Annular threads 387 are defined in the outer face of flange 386. Circular cap 390 has annular threads 391. Cap 390 is attached to specimen container 380 by the rotation of cap 390 relative to specimen container 390 to mate threads 387 and 391.

Cap 390 is removably retained to specimen container 380 by a cap retainer 392. Cap retainer 392 has an elongated arm 395 having a proximal end 396 removably attached to flange 386 and a distal end 397 attached to arc shaped rib 393. Rib 393 is connected to cap 390 by tabs 394. Tabs 394 provide a weak connection between rib 393 and cap 390.

A user places cap 390 over specimen container 380. Cap retainer 392 aligns threads 387 and 391. As cap 390 is rotated relative to specimen container 380, tabs 394 break separating cap 390 from cap retainer 392. A user can then pull on arm 395 to remove cap retainer 392 from specimen container 380.

As shown in FIG. 14, a user may place tissue trap 350 containing a tissue sample 398 into compartment 388 thereby submerging the tissue trap 350 and the tissue sample 398 under preservative solution 389. Tissue sample 398 can be a wide variety of tissue specimens. For example, tissue sample 398 can be a biopsy sample from a body location or a polyp from a colon. Cap 390 is then screwed onto specimen container 380 to seal the tissue sample 398 and tissue trap 350 within specimen container 380.

C. Operation of the First Embodiment

Referring to FIGS. 1-14, mobile unit 30 (FIG. 1) is prepared for use by a user inserting the cassette 200 into the complementary receptacle 102 of manifold assembly 100 associated with the canister 38. This step is performed by inserting the cassette 200 into the receptacle 102 so that back panel 215 is directed to open door 136. When door 136 is open foot 141 extends through opening 124. Cassette 200 slides into passage 118 until back panel 215 contacts rear panel 110. In this position, cassette discharge port 250 (FIG. 8) is seated against and in fluid communication with suction conduit 59. Curved tubing section 284 is pressed against peristaltic pump roller 74 such that the rotation of the rollers 74 forces irrigation fluid through pump tube 280.

RFID reader 194 recognizes RFID tag 376 of the inserted cassette 200 and sends a signal to controller 192 to allow operation of mobile unit 30 when cassette 200 is seated in receptacle 102. After cassette 200 is inserted into receptacle 102, controller 192 activates light source 129 to illuminate piston 300 and tissue trap 350.

Irrigation line 162 is connected between irrigation fluid source 72 and irrigation connector 150. Irrigation coupler 150 is inserted into slot 132. A user can insert the irrigation coupler 150 by grasping handle 154 and guiding distal end 153 towards slot 132 such that beveled sides 156 engage grooves 135. Continued pushing of handle 154 towards receptacle 102 with manual force causes beveled sides 156 to slide along grooves 135 until the irrigation coupler 150 is fully seated within slot 132. In this position, outlet fitting 158 makes a connection through irrigation connector 260 to pump tube 280. Outlet fitting 158 is then in fluid communication with pump tube 280.

Mobile unit 30 is completed for use by coupling of an applicator 52 such as a colonoscope to the unit by attaching suction line 50 to fitting 180 and irrigation line 51 to fitting 181.

Cassette 200 is selected for a mode of operation by the positioning of piston 300 within sleeve 240. Piston 300 is initially in a position as shown in FIG. 3 where piston 300 is located in the distal end 244 of sleeve 240. This is the bypass position. In the bypass position, piston 300 is aligned such that recess 312 is aligned under end 229 of fitting 180 and aperture 314 is aligned with aperture cassette discharge port thereby allowing fluid flow through piston 300.

Mobile unit 30 is actuated by activating the suction pump 58 and peristaltic pump 70. Activation of suction pump 58 results in a waste stream being drawn along a suction fluid communication path 184 from the surgical site into the applicator 52, through the suction line 50 and into fitting 180. From fitting 180, the waste stream travels through the piston specifically through recess 312, into aperture 314, through the hollow interior cavity 301. The waste then flows out through piston aperture 316 and cassette discharge port 250 into conduit 59. From conduit 59, the waste stream flows into canister 38. This mode of operation is referred to as the bypass mode because the suction fluid communication path 184 bypasses tissue trap 350.

Liquid and solid components of the waste stream that enter the canister 36 or 38 precipitate out of the stream and are held in the canister 36 and 38 for final disposal.

Activation of peristaltic pump 70 results in irrigation fluid being pumped along an irrigation fluid communication path 182 from irrigation source 72, through irrigation line 162, irrigation connector 150, pump tube 280, irrigation fitting 181, irrigation line 51 and into the applicator 52 for application at the surgical site.

A user can elect to collect a tissue sample such as a polyp using cassette 200. Cassette 200 is placed in a tissue collection mode by repositioning piston 300 within sleeve 240.

A user manually inserts tissue trap 350 into sleeve 240 such that piston 300 is displaced distally away from screen 350 and further into sleeve 240. Centering features 362 and 364 guide tissue trap 350 into flange 308 of piston 300 and into abutting contact with panel 306.

This position is shown in FIG. 2, where piston 300 is located toward the proximal end 245 of sleeve 240. When tissue trap 350 is fully inserted into sleeve 240, flange 358 abuts cassette proximal end 244. This is the tissue collection position. In the tissue collection position, tissue trap 350 is aligned such that cavity 360 is aligned under the opening of fitting 180 and aperture 366 is aligned with cassette discharge port 250 thereby allowing fluid flow through piston tissue trap 350. In the tissue collection position, piston 300 is not part of the fluid communication path.

When the system is in the tissue collection mode, the waste stream is drawn along a suction fluid communication path 184 from the surgical site into the applicator 52, through the suction line 50 and into fitting 180. This waste stream includes the tissue sample 398 entrained in the suction applicator 52 as a result of suction draw through the applicator. From fitting 180, the waste stream travels through cavity 360, screen 368, aperture 366 and aperture 250 into conduit 59. From conduit 59, the waste stream flows into canister 38. The tissue sample 398 is trapped by the screen 368 within tissue trap 350. This mode of operation is referred to as the tissue collection mode because the suction fluid communication path 184 travels through tissue trap 350. It is noted that in order to collect samples in the tissue collection mode, it is not required to disconnect or re-connect the suction line 50.

The plastic from which the tissue trap 350 is formed from is at least partially transparent allowing a user to view the tissue sample 398. The tissue sample 398 is illuminated within tissue trap 350 by light source 129.

Tissue trap 350 is removed from sleeve 240 by a user activating linear actuator 80. Alternatively, tissue trap 350 can be removed by a user manually pulling on tissue trap 350 or by the use of a lever or spring mechanism (not shown). The user presses an input device such as a button on control panel 196 to activate actuator 80. Actuator 80 drives shaft 82 in a linear manner pushing on piston 300 and causing piston 300 to move from proximal end 245 towards distal end 244 of sleeve 240. The movement of piston 300 causes tissue trap 350 to move out from bore 246 of sleeve 240 where the user may grasp tissue trap 350. With the return of the piston to the proximal position, the system is considered returned to the bypass mode.

If at a later time during the procedure, the practitioner believes it useful to collect another tissue sample, another trap 350 can be inserted into bore 246 of sleeve 240 in order to collect another tissue sample. Multiple tissue samples may be collected using multiple tissue traps 350. Multiple tissue samples can be collected without disconnection or re-connection of the suction line 50 during the procedure.

It should be appreciated that another feature of this invention is that the system can be switched between the bypass and tissue collection modes of operation without having to, during this transition, deactivate the suction pump. This means that when performing tissue collection using this invention, the overall length of time to perform the procedure is not lengthened by the need to have take the time required to repeatedly turn the suction pump 58 on and off.

After removing tissue trap 350 from cassette 200, the user places tissue trap 350 into specimen container 380 where it is submerged into preservative solution 389 thereby covering tissue sample 398 as seen in FIG. 14. The user places cap 390 over specimen container 380. Cap retainer 392 aligns threads 391 and 387. As cap 390 is rotated onto specimen container 380, tabs 394 break separating cap 390 from cap retainer 392. A user can then pull on arm 395 to remove cap retainer 392 from specimen container 380. The specimen container 380 is sent to a pathology lab for analysis.

Once the medical/surgical procedure is completed, and use of the mobile unit 30 is no longer required, suction line 50 and irrigation line 51 may be disconnected from fittings 180 and 181, respectively and irrigation coupler 150 may be disconnected from receptacle 102. Cassette 200 is removed from receptacle 102. After cassette 200 is removed from receptacle 102, door 136 closes passage 118. When door 136 is in the closed position, foot 141 covers conduit 59 sealing the entrance to conduit 59. The closing of the passage 118 substantially eliminates leakage of any waste material remaining in the receptacle 102. Cassette 200 is disposed of as medical waste.

After use, the mobile unit 30 is coupled to a docker (not illustrated and not part of this invention.) Waste material in the canister 36 or 38 is flowed through the docker to a treatment facility.

The outlet fitting 158 forms a seal with body 262 at inlet port 268. These components are dimensioned so that, when mated together, the feet 264 apply a spring force to body 262 biasing inlet port 268 against outlet fitting 158. The compression of these two components against each other forms a substantially fluid tight barrier between these components. Thus, the need to provide an O-ring or other sealing element is eliminated. This simplifies the manufacture of cassette 200.

It should likewise be recognized that in versions of the invention, the plastic from which the tissue trap 350 and specimen container 380 are formed from are at least partially transparent. This provides medical personnel with a quick means to verify that the tissue sample has been collected. Further cassette 200 is formed from materials that are at least partially transparent. This provides medical personnel with a quick means to verify that the cassette has not been previously used and does not contain previously collected waste.

III. Second Embodiment

A. Receptacle

Figure 15A:
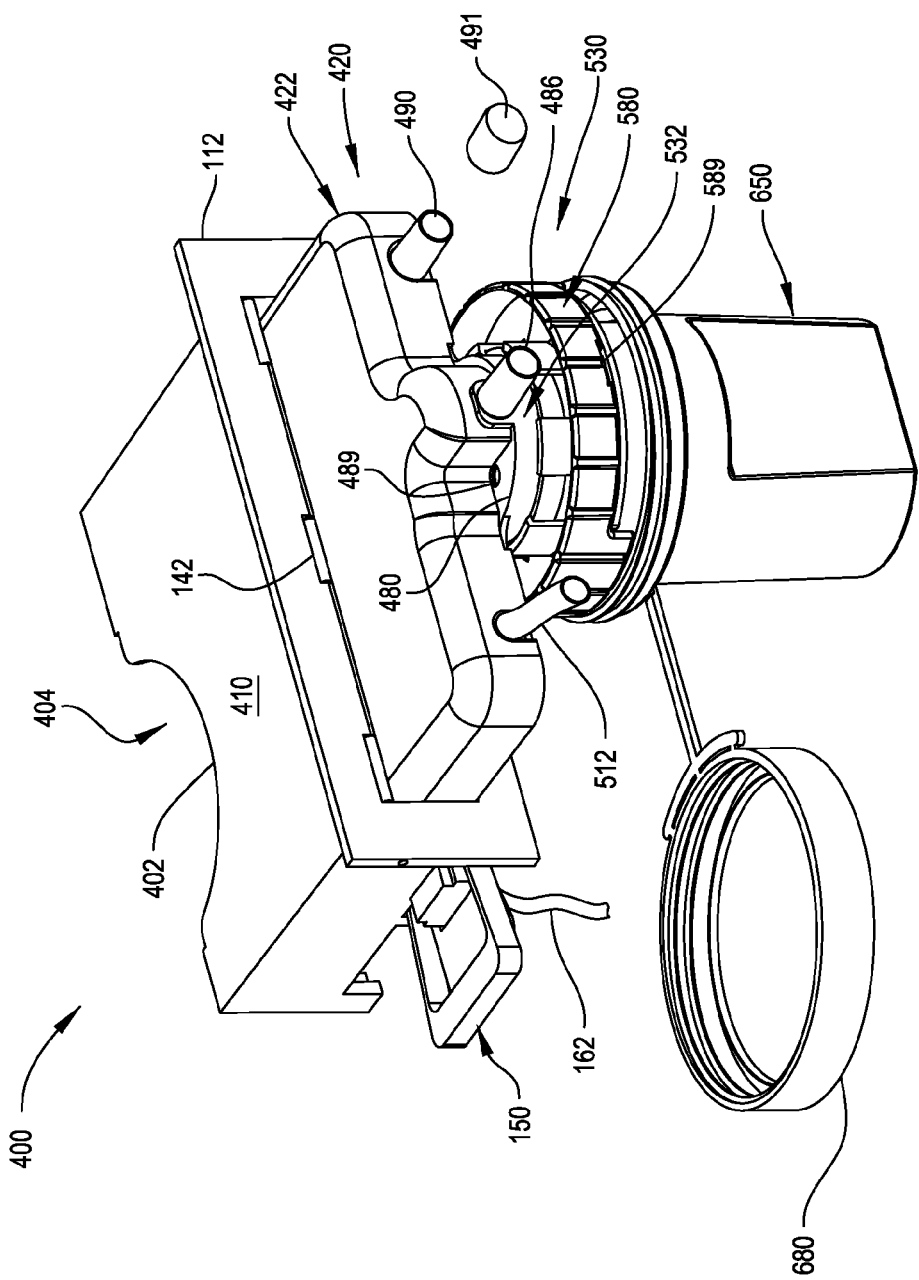
FIG. 15A is a left front perspective view of another embodiment of a manifold assembly.
Figure 15B:
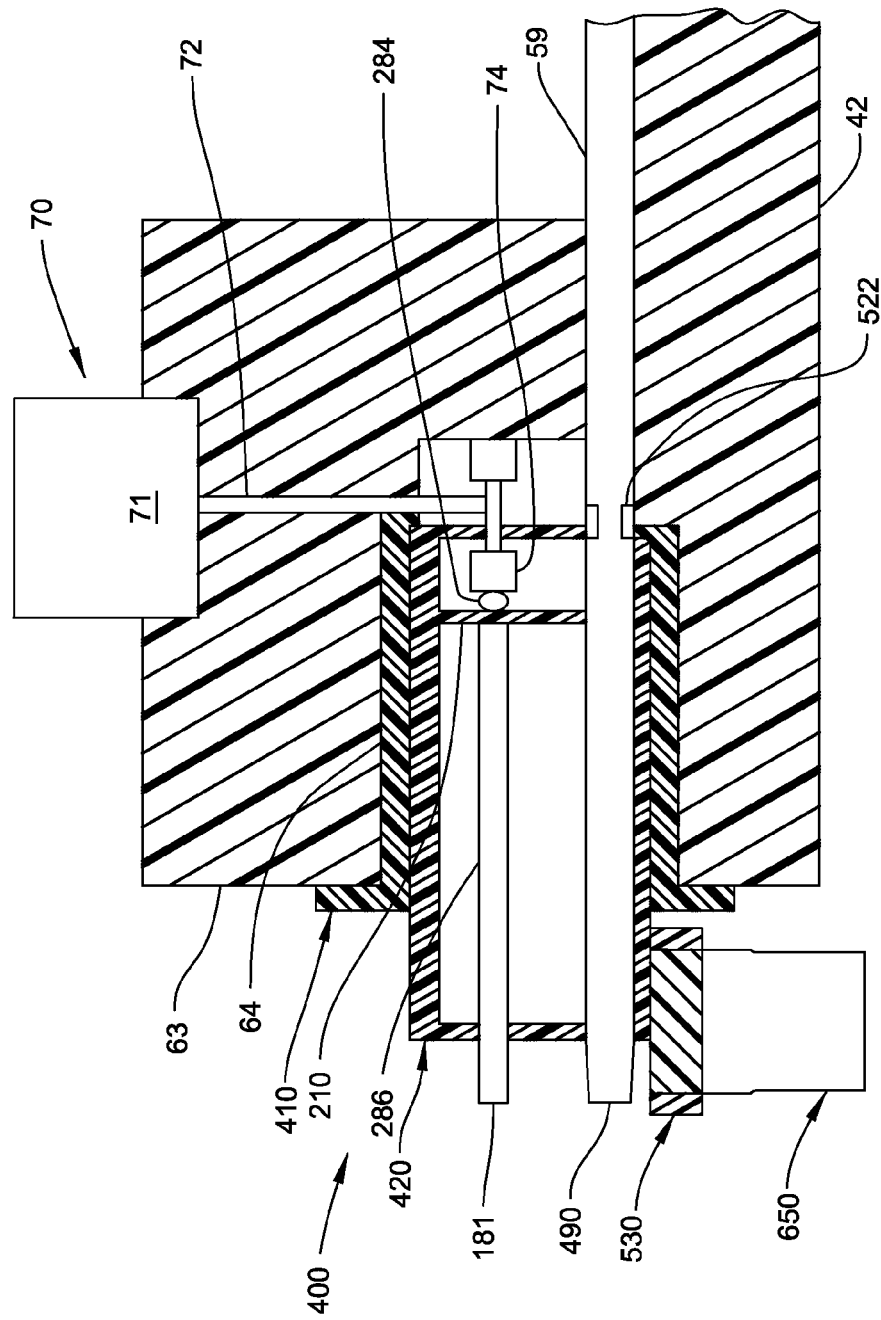
FIG. 15B is a cross sectional view of the manifold assembly of FIG. 15A mounted in a waste collection system.
Figure 16:
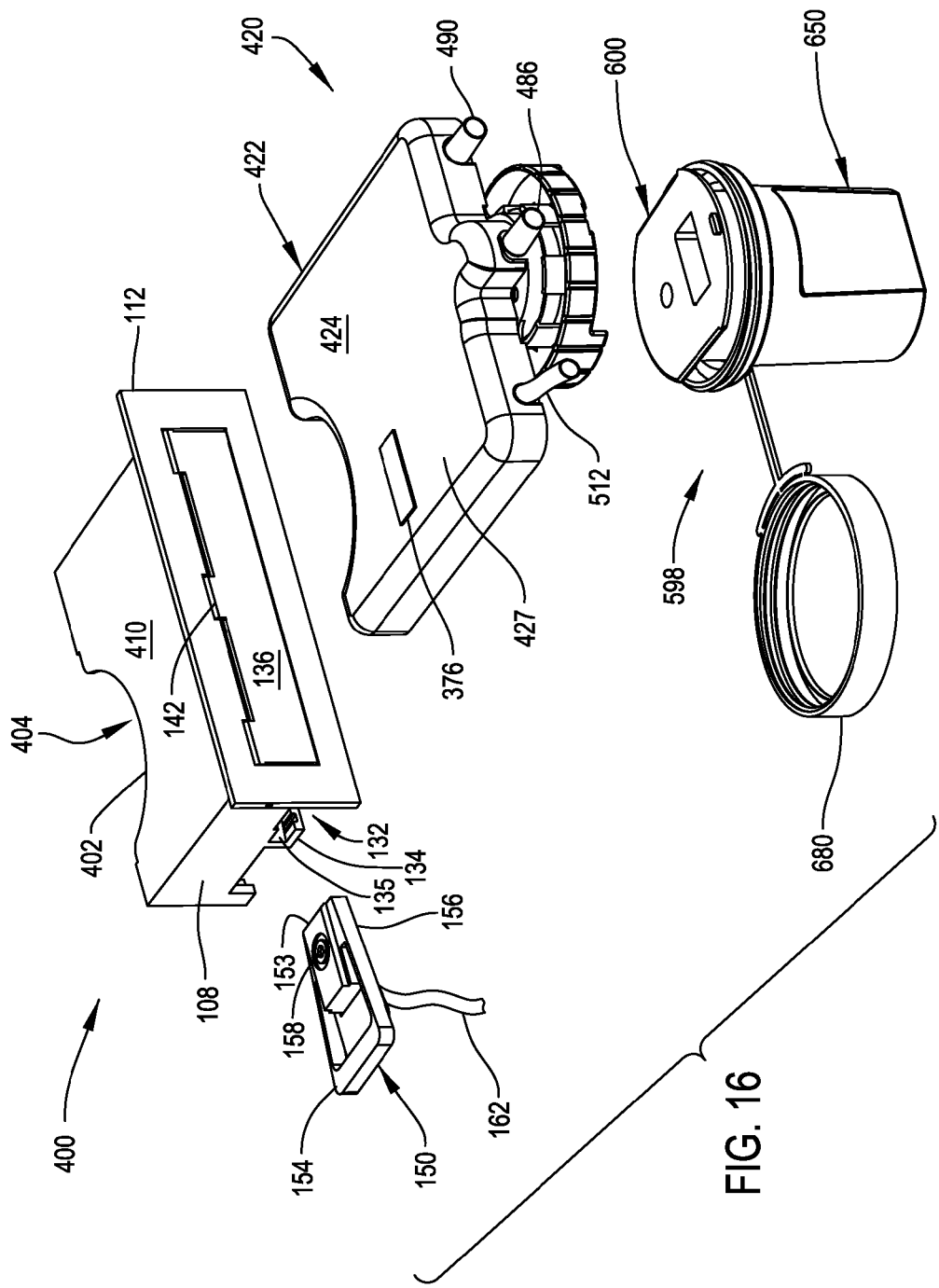
FIG. 16 is a left front exploded view of the manifold assembly of FIG. 15.
Figure 17:
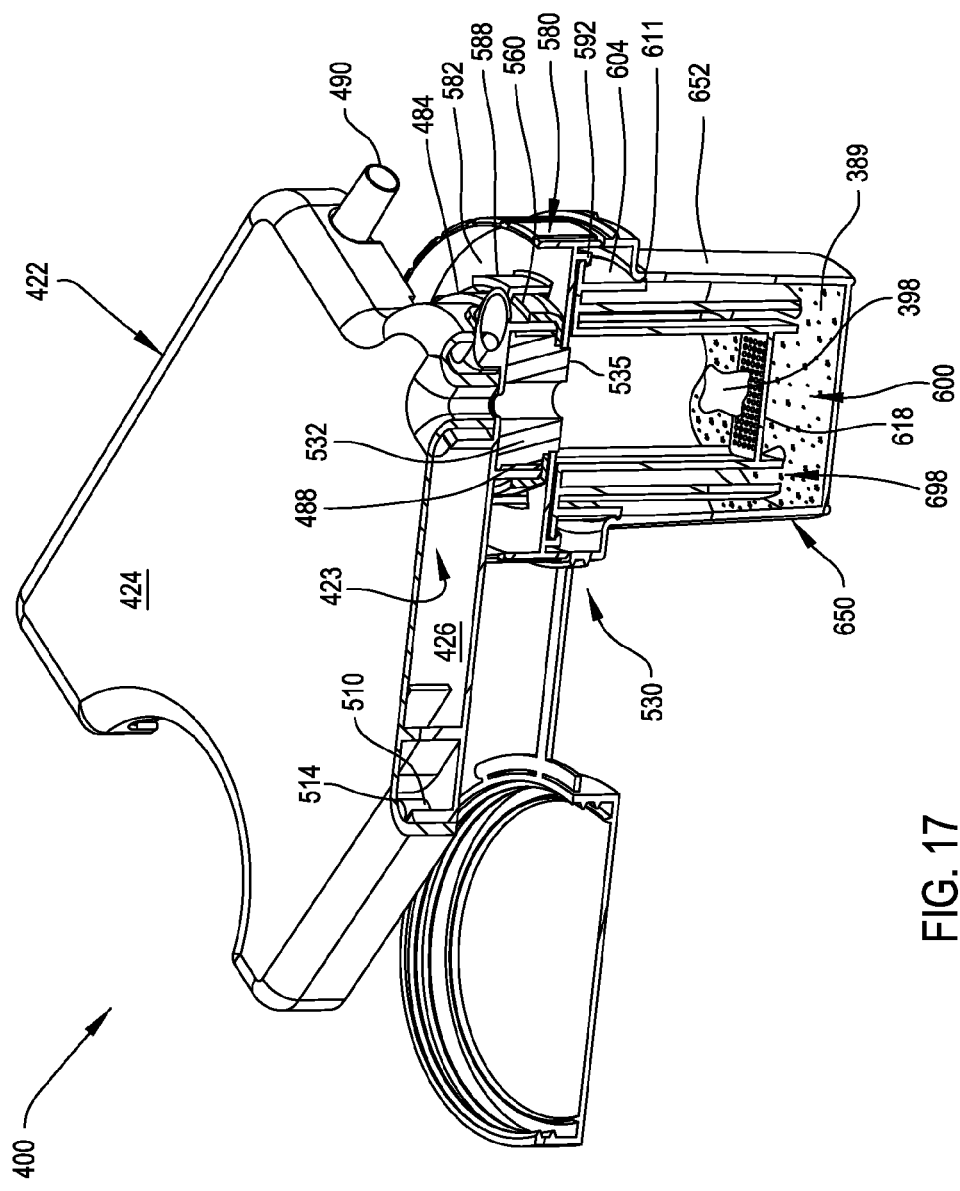
FIG. 17 is a cross-sectional view of the manifold assembly of FIG. 15.
Figure 18A:
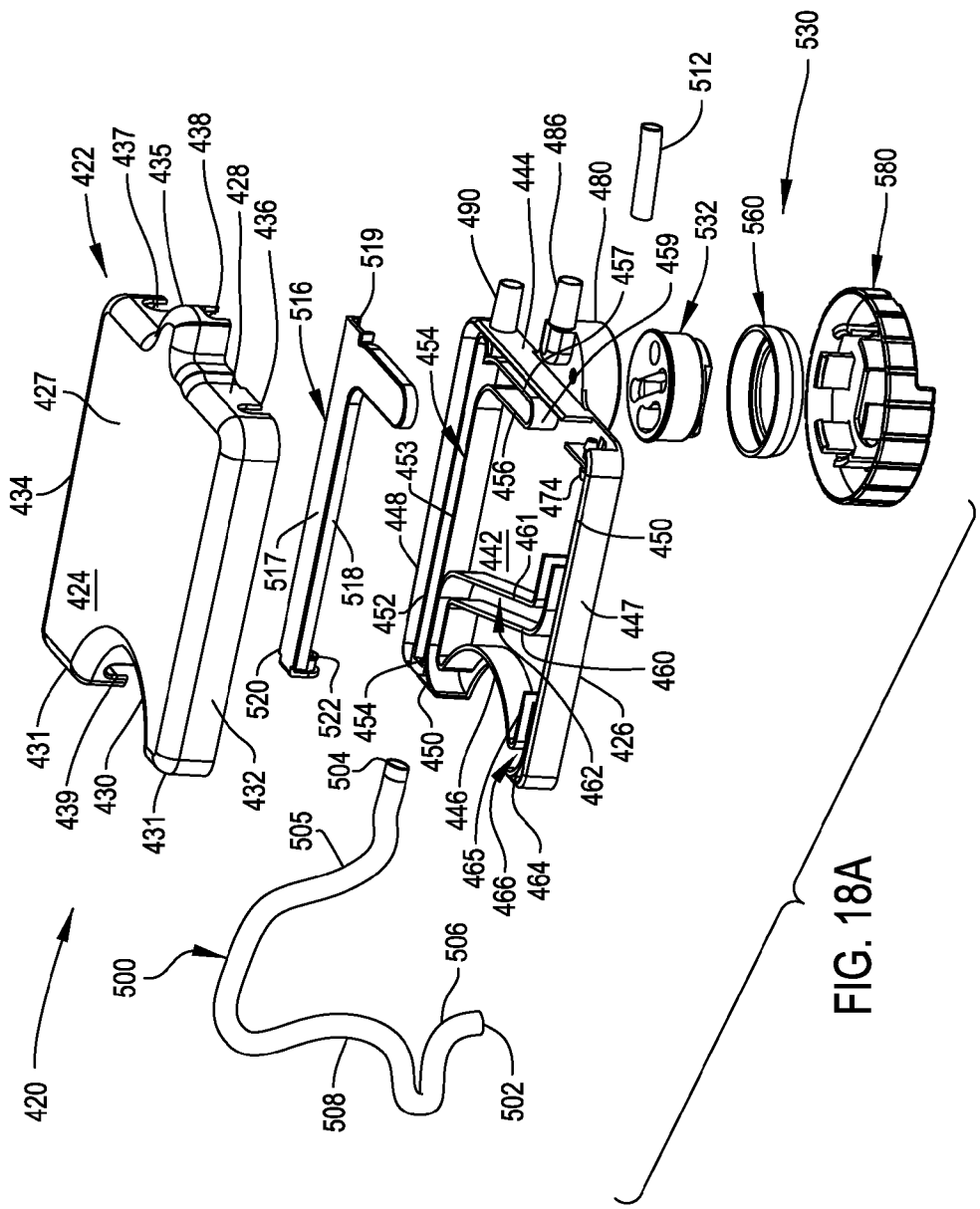
FIG. 18A is a perspective exploded view of the cassette of FIG. 15.
Figure 18B:
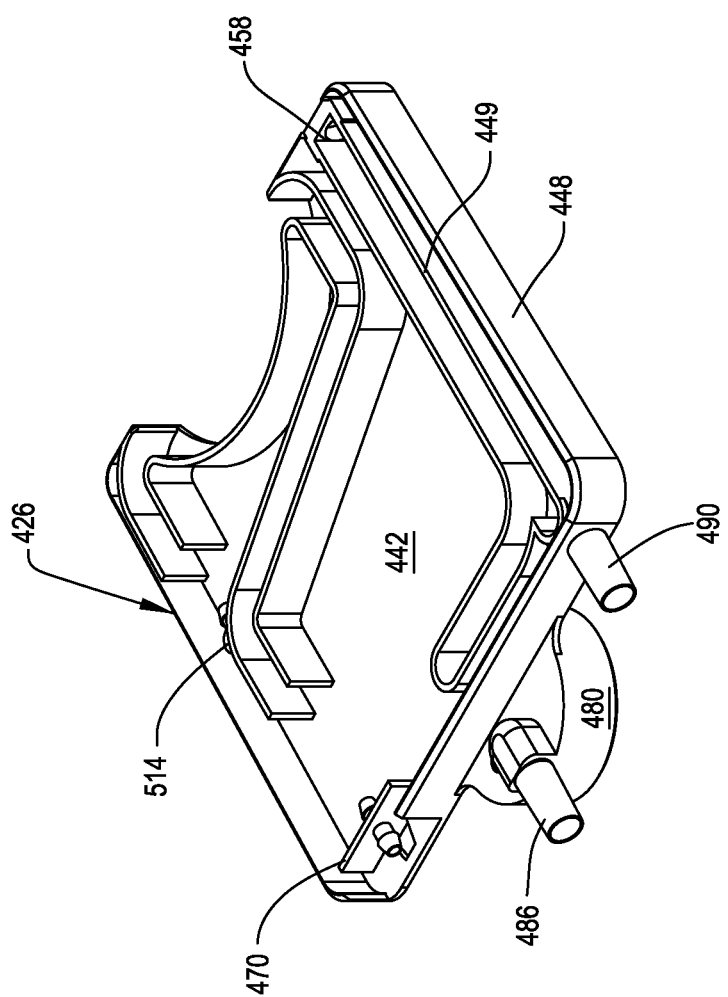
FIG. 18B is a perspective view of an lower housing.
Figure 18F:
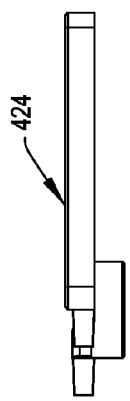
FIG. 18F is a right side view of the upper housing.
Figure 18C:
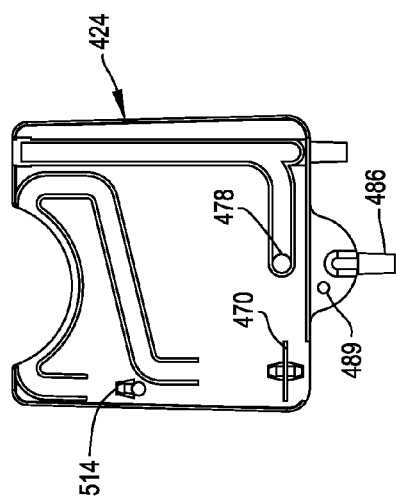
FIG. 18C is top view of the lower housing.
Figure 18E:
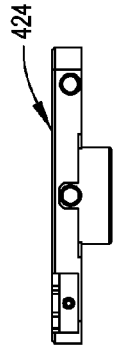
FIG. 18E is a front view of the lower housing.
Figure 18D:
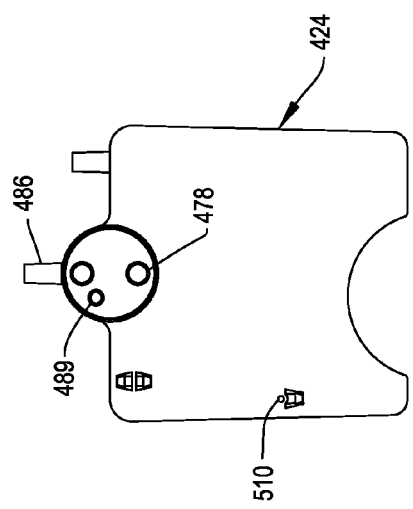
FIG. 18D is a bottom view of the lower housing.

Turning now to FIGS. 15-17, details of a second manifold assembly 400 that can be employed as part of the waste and tissue collections system of this invention are illustrated. Manifold assembly 400 includes receptacle 410, cassette 420, and tissue trap 598. Tissue trap 598 includes a specimen container 650 in which a tissue filter 600 is seated. Receptacle 402 is similar to receptacle 102 described in the first embodiment. Receptacle 410 in the second embodiment has different dimensions including height, length and width than receptacle 102. Receptacle 410 also includes a curved rear panel 402 that defines a recess 404 distal to rear panel 402. Door 136 of FIG. 15 does not include a foot 141 as was shown in the receptacle 102 of FIG. 3.

With additional reference to FIGS. 1A and 15B, attached to canister cap 42 of canister 38 is a manifold assembly 400. Manifold assembly 400 includes a receptacle 410 and a cassette 420. Cassette 420 is removably seated in receptacle 410. As described below, cassette 420 is formed with a number of fittings 490 and 181. Fitting 490 can receive a suction line 50 and fitting 181 can receive an irrigation line 51. The distal end of each suction line 50 and irrigation line 51 is attached to a suction applicator colonoscope 52. (Here, "distal", refers to towards the surgical site at which the suction is applied and "proximal" means away from the surgical site.) In FIG. 1A, suction applicator 52 is diagrammatically shown as a hand piece specifically and solely designed to apply suction and irrigation, it should be understood that this is exemplary, not limiting. Sometimes the suction applicator 52 is built into another surgical tool, such as a colonoscope biopsy tool or ablation tool, applied to a surgical site to accomplish a task other than applying suction and irrigation.

Internal to cap 42 is conduit 59. Conduit 59 functions as a fluid communications path from the receptacle 410 into the canister 36 or 38 with which the receptacle is associated. The suction fluid channel 454 within cassette 420 exits from the rear of cassette 420 and receptacle 410 into horizontally oriented conduit 59 located at the back of cavity 64.

Also part of mobile unit 30 is a suction pump 58 and peristaltic pump 70. Conduits 59 and 60, (shown as dashed lines in FIG. 1A) connect each canister 36 and 38 to the inlet port of the suction pump 58. When suction pump 58 is actuated, the resultant suction draws matter into the applicator 52 and through the associated suction line 50, cassette and receptacle.

A continuous suction fluid communication path 184 is formed from applicator 52 to suction pump 58. The waste stream flows from the receptacle 410 into the associated canister 36. Liquid and small solid bits of matter entrained in this flow stream precipitate out of the stream into the canister 38. This waste is thus stored in the canister 36 until the canister is emptied. Gas and any small bits of matter entrained in this flow stream flow from the canister towards the suction pump 58.

As seen in FIG. 2, cap 42 is formed to have a solid cap head 63 that projects upwardly from the top surface of the base of the cap. A cavity 64 is defined in cap head 63. Receptacle 410 is mounted in cavity 64. Receptacle 410 is secured to cavity 64 with the panels of receptacle 410 in contact with the interior panels of cap head 63. Cassette 420 is removably retained within receptacle 410. Irrigation fitting 180 and suction fitting 490 extend distally away from cassette 420.

Peristaltic pump 70 is coupled with irrigation line 51 such that rotation of peristaltic pump 70 forces irrigation liquid from an irrigation liquid source 72 through irrigation line 162, cassette 200 and irrigation line 51 to applicator 52 where it is supplied to a surgical site. Peristaltic pump 70 comprises a rotary electric motor 71 that is connected to eccentric rollers 74. Peristaltic pump 70 can supply irrigation fluid to applicator 52 as will be described later in more detail. A continuous irrigation fluid communication path 182 is formed from irrigation liquid source 72 to applicator 52.

B. Cassette

With additional reference to FIGS. 18A-F and 19, cassette 420 is generally square in shape and comprises a housing 422 that has two pieces, an upper housing 424 and an opposed lower housing 426. While the housing is illustrated using two pieces, it is contemplated that housing 422 can be formed as a single unitary part. Upper housing 424 and lower housing 426 are mated together to form housing 422. A cavity 423 is defined within housing 422 between upper housing 424 and lower housing 426. Upper housing 424 includes a planar top panel 427, front panel 428, curved back panel 430, and side panels 432, and 434. Panels 428, 430, 432, and 434 extend perpendicularly away from top panel 427. A nose 435 extends outwardly from the center of front panel 428. A U-shaped opening 436 is located in front panel 428 towards panel 432. A U-shaped opening 437 is located in front panel 428 towards panel 434. A U-shaped opening 438 is located in nose 435. A U-shaped opening 439 is located in rear panel 430. Cassette 420 is formed from any suitable material such as injection molded plastic.

Lower housing 426 includes a planar bottom panel 442, front panel 444, curved back panel 446, back panel 450 and side panels 447 and 448. Panels 444, 446, 447 and 448 extend perpendicularly away from bottom panel 442 and each have a beveled edge 449 except for back panel 446.

A pair of interior support panels, 452 and 453, extend between front panel 444 and back panel 450 adjacent to and spaced from panel 448. Interior support panels 452 and 453 are generally parallel to each other and extend perpendicularly away from bottom panel 442. Interior support panels 452 and 453 define a channel 454. Support panels, 452 and 453 have ends 456 and 457, respectively that make a ninety degree bend adjacent and slightly spaced from panel 444 and extend parallel with panel 444 and terminate at end 459 toward the center of panel 444. An aperture 458 is located in back panel 450 and is in fluid communication with channel 454. Aperture 478 extends through bottom panel 442 at end 459. Aperture 478 is in fluid communication with channel 454. A secondary suction fitting 490 extends through and outwardly from front panel 444. Secondary suction fitting 490 is in fluid communication with channel 454. Secondary suction fitting 490 is coupled to an optional second suction line (not shown) and is sealed off with a cap 491 (FIG. 15) when not in use.

Another pair of interior support panels, 460 and 461, extend in a sinuous manner between curved back panel 446 and a location adjacent to panel 447 and spaced from panel 447. Interior support panels 460 and 461 are spaced apart generally equal to each other and extend perpendicularly away from bottom panel 442. Interior support panels 460 and 461 define a first irrigation tube channel 462.

An additional pair of interior support panels, 464 and 465, extend for a short distance between curved back panel 446 and a location adjacent to panel 447. Interior support panels 464 and 465 are generally parallel and extend perpendicularly away from bottom panel 442. Interior support panels 464 and 465 define a second irrigation tube channel 466.

An identification device 376 (FIG. 16) is attached to top panel 427 of upper housing 424. Identification device 376 any suitable identification device such as a radio frequency identification (RFID) device, a bar code, a magnetic strip or other memory device. The identification device can contain information such as set-up information, expiration information and controls for re-use or reprocessing.

Figure 19:
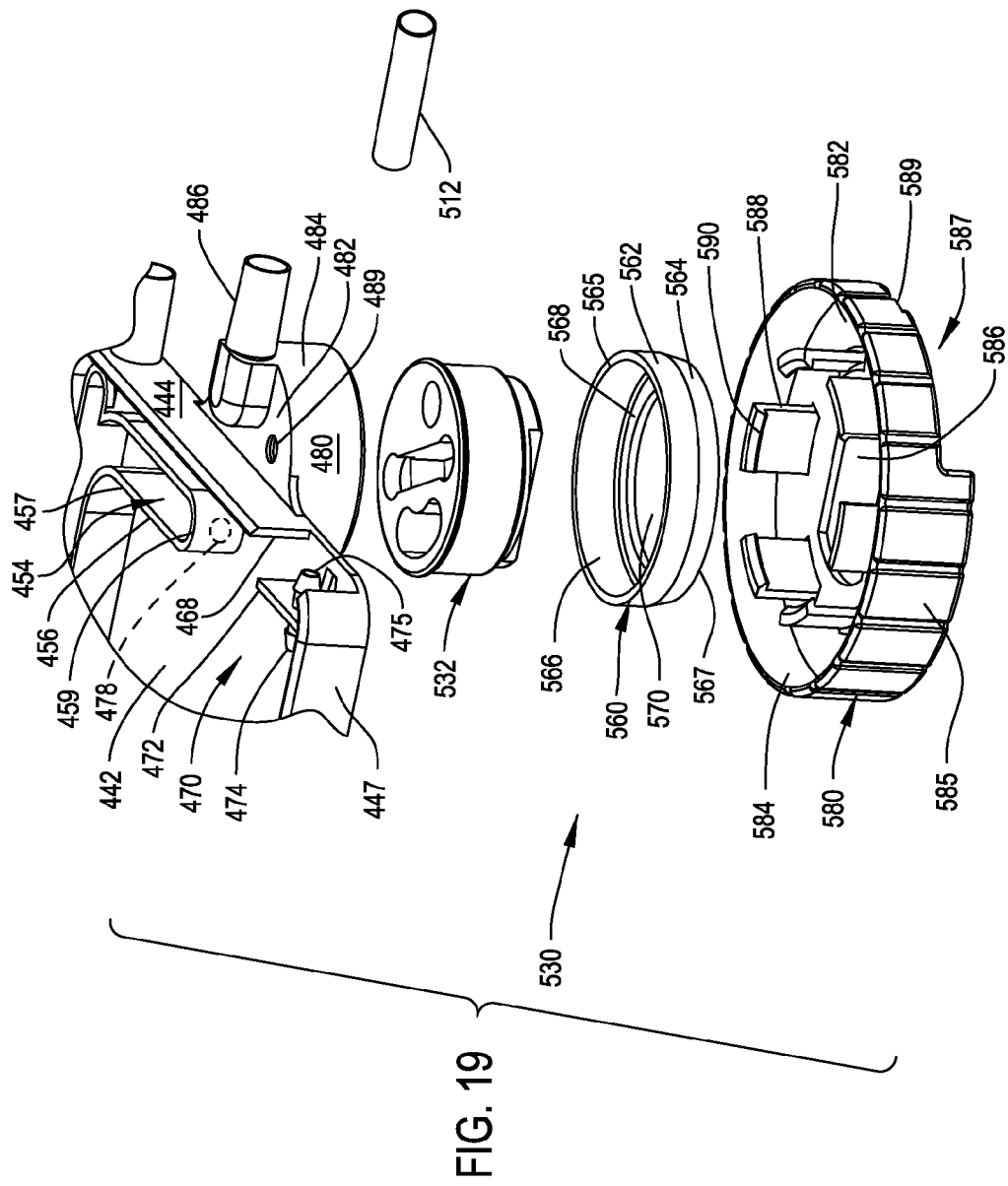
FIG. 19 is an enlarged perspective exploded view showing details of FIG. 18A.
Figure 21D:
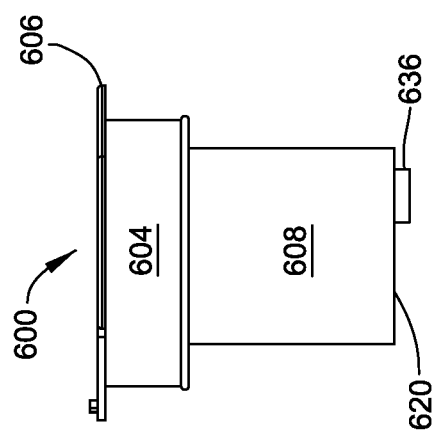
FIG. 21D is a side view of the tissue trap.
Figure 21C:
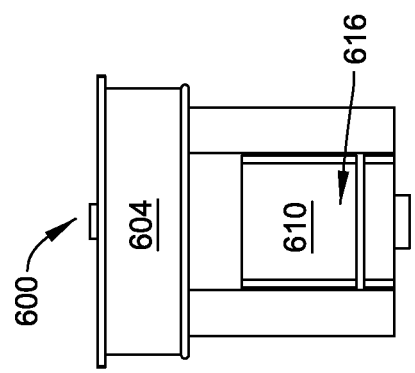
FIG. 21C is front view of the tissue trap.

With reference to FIG. 19, a generally rectangular opening 468 is located in front panel 444. An irrigation connector 470 is located within a corner of cassette 420 adjacent to panel 447 and opening 468. Irrigation connector 470 has a panel 472 that extends perpendicularly upward from bottom panel 442. A tapered nozzle 474 extends in a distal direction away from panel 472 and a tapered nozzle 475 extends in a proximal direction away from panel 472 towards opening 468. Irrigation fitting 512 extends through opening 468 and is connected with nozzle 475.

A circular boss 480 extends outwardly from front panel 444 and downwardly from bottom panel 442. Boss 480 has a generally horizontal top panel 482 and a generally vertical curved side 484. Side panel 484 is perpendicular to top panel 482. Side panel 484 and top panel 482 define an annular cavity 488 (FIG. 17) therein. A fitting 486 extends upwardly from top panel 482 and outwardly from side panel 484. Tissue deposit port 489 extends through top panel 482.

Returning to FIGS. 18A-F, a sinuous shaped pump tube 500 has ends 502 and 504, sections 505 and 506 and curved pump section 508. Pump tube 500 is retained within cassette 420 between upper housing 424 and lower housing 426. Pump tube 500 can be formed from any suitable material such as plastic or silicone rubber. End 504 is press fit over tapered nozzle 474. Section 505 is positioned and retained within channel 462 between panels 460 and 461. Section 506 is positioned and retained within channel 466 between panels 464 and 465. Curved pump section 508 is located adjacent to and extends along the outer surface of curved back panel 446. The rotating peristaltic pump roller 74 (FIG. 2) is adapted to movably press on and squeeze curved pump section 508 between pump roller 74 and curved back panel 446. End 502 is press fit over a ninety degree elbow fitting 514. Elbow fitting 514 is located inwardly adjacent to panel 447. Elbow fitting 514 turns downward to extend through panel 426 at aperture 510 (FIG. 17). Pump tube 500 provides a fluid communication path for irrigation liquid to flow from irrigation coupler 150 to irrigation fitting 512.

An elongated L-shaped cover 516 rests on panels 452, 453, 456 and 457 and provides a fluid seal for channel 454. Cover 516 has a top panel 517 and side panels 518. Side panels 518 extend over and partially down panels 452, 453, 456 and 457. Cover 516 has a proximal end 519 positioned toward back panel 450 and a distal end 520 positioned toward front panel 444. A duct 522 is located at distal end 520 below top panel 517. Duct 522 is positioned through aperture 458 and extends into channel 454. Duct 522 is in fluid communication with channel 454.

Upper housing 424 and lower housing 426 are mated together to form housing 422 of cassette 420. Housings 424 and 426 are retained to each other by press-fitting or snap fitting the two housing sections together. Alternatively, housings 424 and 426 can be retained by an adhesive or welding. When housings 424 and 426 are pressed together to mate, beveled edges 450 force panels 444, 447, and 448 to be seated inwardly of panels 428, 432 and 434, respectively.

Cassette 420 further includes a valve assembly 530. Valve assembly 530 comprises valve member 532, retaining ring 560 and knurled knob 580. As seen in FIGS. 20A-20D, valve member 532 has a generally cylindrical shape with a top face 534, bottom face 535 and side surface 536. A rim 537 extends circumferentially outward from top face 534 extending slightly over side surface 536. An opposed pair of parallel spaced apart steps 538 are defined in bottom face 535. Bores 540 and 542 extend through valve member 532 between top face 534 and bottom face 535. Curved slot 544 is defined in top face 534 and is coextensive with bore 542.

Bypass channel 550 is defined in top face 534 and extends substantially across the width of top face 534. Bypass channel 550 is defined by a central groove 552 and partial bores 554 and 556. Partial bores 554 and 556 extend partially into valve member perpendicularly from top face 534. Central groove 552 is coextensive with partial bores 554 and 556.

Turning to FIG. 19, annular ring 560 has an upper outer surface 562 and a tapered lower outer surface 564, rim 565, inner surface 566, bottom side 567 and annular step 568. Hole 570 is defined in ring 580. Annular step 568 extends partially into hole 570.

Knurled knob 580 includes a bottom panel 582 and an annular side panel 584. Side panel 584 extends perpendicularly from bottom panel 582. A series of knurled portions or ribs 585 extend circumferentially around the outer surface of side panel 584. A user may grasp knurled portions or ribs 585 with their hand. Opening 586 is defined in bottom panel 582. Recess 587 is defined in the front face of side panel 584. A notch 589 is defined in the front face of side panel 584 above recess 587. A series of projections 588 extend perpendicularly upward from bottom panel 582 and are arrayed around opening 586. Projections 588 are flexible and are angled slightly inwardly toward opening 586. A lip 590 is located at the distal end of each projection 588 and extends inwardly from projection 588. A pair of opposed spaced apart L-shaped rails 592 (seen in FIG. 17) extend below the bottom surface of bottom panel 582.

With reference now to FIGS. 15, 17, 19 and 20A, valve assembly 530 is attached to boss 480. Valve member 532 is seated in cavity 488 with top face 534 located adjacent the bottom of panel 482 and panel 442. Rim 537 is in contact with the inside of panel 484. Annular step 568 of ring 560 surrounds and is in contacting support with annular step 538 of valve member 532. Inner surface 566 of ring 560 is in contact with the outside of panel 484. Bottom panel 582 supports the bottom 567 of ring 560. Bottom face 535 extends through opening 586. Projections 588 grasp ring 560 with lip 590 extending over rim 565.

When knob 580 is pressed against ring 560, projections 588 flex outwardly and slide in contact with surfaces 562 and 564 until lip 590 moves over rim 565 and projections 588 flex inwardly grasping ring 560. Projections 588 squeeze ring 560 against boss 480 holding valve assembly 530 to housing 422. Valve member 532 is rotated by a user grasping knob 580 thereby rotating the entire valve assembly 530 relative to boss 480.

With reference to FIGS. 21A-21F, a tissue filter 600 is shown. Tissue filter 600 is generally cylindrical in shape. Other shapes such as round, oval or square can be utilized. Tissue filter 600 can be formed from any suitable material such as low durometer plastic or thermoplastic elastomer. Tissue filter 600 can be formed from a transparent material such that the contents may be viewed by a user. Tissue filter 600 is defined by a top panel 602. An annular side panel 604 extends perpendicularly away from the bottom of top panel 602 with a smaller diameter than top panel 602 and defines a circumferential flange 606. A lip 611, best viewed in FIG. 17, extends circumferentially outward from the bottom of side panel 604. Arc shaped vertically oriented side panels 608 and 609 depend downwardly from annular side panel 604. A U-shaped spaced vertically oriented panel 610 depends downwardly from annular side panel 604.

Figure 22A:
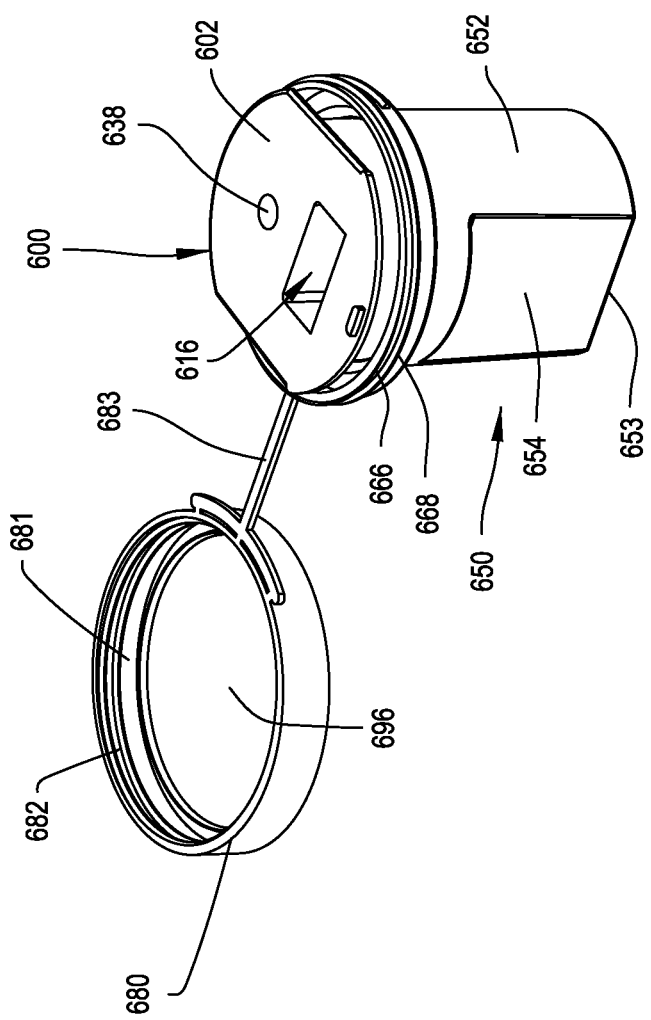
FIG. 22A is a perspective view of the tissue trap contained within a specimen container.

Panels 608, 609 and 610 define a reservoir 612 (FIG. 22D). In one embodiment, reservoir 612 can contain a preservative solution 389 (FIG. 22D) such as formalin or other suitable preservative solution. In another embodiment, the preservative solution is omitted. Preservative solution 389 is sealed within reservoir 612 by a foil or plastic seal 614.

U-shaped spaced vertically oriented panel 610 defines a rectangular shaped cavity 616. A rectangular shaped screen 618 is mounted in cavity 616 and is attached to panels 608 and 610. Screen 618 is spaced slightly from a distal end 620 in cavity 616. An opening 622 is located in top panel 602 and is continuous with cavity 616.

Circumferential flange 606 has a pair of parallel edges 623 and 624 located on opposite sides of top panel 602 and a pair of curved edges 626 and 627 located on opposite sides of top panel 602. Tab 630 extends upwardly from flange 606 adjacent to edge 627. Tab 630 is an alignment feature that prevents the backward insertion of tissue filter 600 into valve assembly 530. Tab 630 passes into notch 589 when tissue filter 600 is inserted into valve assembly 530.

A duct 632 has a proximal end 634 and distal end 636. Duct 632 is oriented generally parallel to and partially surrounded by panel 609. Proximal end 634 extends through side panel 604 and terminates at top panel 602. Distal end 636 extends slightly beyond and below end 620. Bore 638 extends through duct 632.

FIGS. 22A-22D illustrate a specimen container or jar 650. Specimen container or jar 650 has a generally cylindrical shape with an outer panel 652, a bottom panel 653. A pair of planar diametrically opposed spaced apart grasping sections 654 are located in outer panel 652 on opposing sides of specimen container 650. A compartment 658 is defined within specimen container 650. Specimen container 650 is formed from a transparent material such that the contents of compartment 658 may be viewed by a user through a single flat wall. The planar shape of the wall substantially eliminates the visual distortion of the contents of the compartment.

An annular flange 666 extends peripherally upward and outward from panel 652. Annular threads 668 are defined in the outer face of flange 666. Circular cap 680 has annular threads 682 located on an inner surface of side panel 683. Cap 680 is attached to specimen container 650 by the rotation of cap 680 relative to specimen container 650 to mate threads 668 and 682.

Cap 680 is removably retained to specimen container 650 by a cap retainer 683. Cap retainer 683 has an elongated arm 685 having a proximal end 686 removably attached to flange 666 and a distal end 687 attached to arc shaped rib 693. Rib 693 is connected to cap 680 by tabs 694. Tabs 694 provide a weak connection between rib 693 and cap 680.

An identification device 376 is attached to cap 680. Identification device 376 is any suitable identification device such as a radio frequency identification (RFID) device, a bar code, a magnetic strip or other memory device. The identification device can contain information such as: set-up information; expiration information; patient or specimen tracking; and data regarding re-use or reprocessing.

Tissue sample 398 can be a wide variety of tissue specimens. For example tissue sample 398 can be a biopsy sample from a body location or a polyp from a colon. Tissue filter 600 will slide into compartment 658 until lip 611 engages side panels 652 thereby providing a resistive force to further insertion of tissue filter 600 into compartment 658.

Tissue trap 598 is removably coupled to valve assembly 530. The trap 598 is inserted by pushing tissue filter 600 and specimen container 650 horizontally into recess 587 such that edges 623 and 624 slide into and along L-shaped rails 592. Tissue trap 598 hangs below valve assembly 530. Tissue trap 598 is removed from valve assembly 530 by pulling tissue filter 600 and specimen container 650 horizontally away from valve assembly 530 such that edges 623 and 624 slide out from L-shaped rails 592. Tissue trap 598 is inserted and removed from cassette 420 as a single unit.

A user places cap 680 over tissue filter 600. Cap retainer 683 aligns threads 668 and 682. When cap 680 is rotated relative to specimen container 650, Inner surface 696 of cap 680 contacts top panel 602. Rotation of cap 680 forces tissue filter 600 to move downwardly into compartment 658. Side panel 604 and lip 611 flex inwardly and slide along specimen container panel 652 until distal end 636 contacts bottom panel 653. As tissue filter 600 moves downwardly into compartment 658, pointed tip 698 mounted to bottom panel 653 punctures the foil or plastic seal 614 releasing preservative solution 389 to cover tissue sample 398 as seen in FIG. 17.

As cap 680 is rotated onto specimen container 650, tabs 694 break separating cap 680 from cap retainer 683. A user can then pull on arm 685 to remove cap retainer 683 from specimen container 650.

C. Operation

Referring to FIGS. 1A-C and 15-19, mobile unit 30 (FIG. 1A) is prepared for use inserting the cassette 420 into the complementary receptacle 410 of manifold assembly 400 associated with the canister 36 or 38 in which the waste drawn from the surgical site is to be collected. This step is performed by inserting the cassette 420 into the receptacle 410 so that back panel 431 is directed to open door 136. Cassette 420 slides into passage 118 until back panel 431 contacts rear panel 110. In this position, duct 522 seats against and in fluid communication with suction conduit 59 (FIG. 15B). Curved tubing section 508 is pressed against peristaltic pump roller 74 such that the rotation of roller 74 forces irrigation fluid through pump tube 500. RFID reader 194 recognizes identification device 376 such as an RFID tag and sends a signal to controller 192 to allow operation of mobile unit 30 when cassette 420 is seated in receptacle 410.

Irrigation line 162 is connected between irrigation fluid source 72 and irrigation connector 150. Irrigation coupler 150 is inserted into slot 132. A user inserts the irrigation coupler 150 by grasping handle 154 and guiding distal end 153 towards slot 132 such that beveled sides 156 engage grooves 135. Continued pushing of handle 154 towards receptacle 102 using manual force causes beveled sides 156 to slide along grooves 135 until the irrigation coupler 150 is fully seated within slot 132. In this position, fitting 158 makes a connection through aperture 510 to elbow fitting 514. Outlet fitting 158 is then in fluid communication with pump tube 500.

The suction line 50 integral with the suction applicator 52 is attached to suction line 50 to fitting 486. If the suction applicator is also able to provide irrigating fluid, irrigating line 51 is attached to fitting 512. Cassette 420 is set in a mode of operation by the setting of knob 580. This results in the corresponding rotation of valve member 532. Often the knob 580 is set so that valve member 532 is rotated to a bypass position. In the bypass position, valve member 532 is aligned such that bore 554 is aligned with the outlet opening of fitting 486 internal to boss 480. Simultaneously, this results in the alignment of valve member bore 556 aligned with boss aperture 478. When the suction is drawn, this results in the fluid stream flowing from fitting 486 thereby allowing fluid flow through bypass channel 550.

Mobile unit 30 is actuated by activating the suction pump 58. Activation of suction pump 58 results in a waste stream being drawn along a suction fluid communication path 184 from the surgical site into the applicator 52, through the suction line 50 and into fitting 486. This waste stream includes liquid and solid waste to which the suction applicator 52 is applied as well as air adjacent the applicator 52. When the cassette is in the above described bypass mode, waste travels from fitting 486 travels through bypass channel 550, through aperture 478 into channel 454 and through duct 522 into conduit 59. From conduit 59, the waste stream flows into the canister 38.

Activation of peristaltic pump 70 results in irrigation fluid being pumped along an irrigation fluid communication path 182 from irrigation source 72, through irrigation line 162, irrigation connector 150, pump tube 500, irrigation connector 472, irrigation fitting 512, irrigation line 51 and into the applicator 52 for application at the surgical site.

A user can elect to collect a tissue sample such as a polyp using cassette 420. Cassette 420 is placed in a tissue collection mode by rotating knob 580. This results in the corresponding rotation of valve member 532. When valve member 532 is in the tissue collection position, the valve member is aligned such that valve member bore 540 is aligned with the opening of fitting 485 within boss 480. The positioning of the valve member in this position also results in the alignment of valve member bore 542 with aperture 478.

When the system is in the tissue collection mode, waste and an entrained tissue sample is drawn along a suction fluid communication path 184 from the surgical site into the applicator 52, through the suction line 50 and into fitting 486. From fitting 486, the waste stream travels through bore 540, cavity 616, screen 618, bore 638, bore 542, slot 545, aperture 478 into channel 454 and through duct 522 into conduit 59. From conduit 59, the waste stream flows into canister 38. Tissue sample 398 is trapped by the screen 618 within tissue filter 600. This mode of operation is referred to as the tissue collection mode because the suction fluid communication path 184 travels through tissue filter 600. It is noted that in order to collect samples in the tissue collection mode, it is not required to disconnect or re-connect the suction line 50.

Cassette 420 and tissue trap 598 may also be used to collect tissue extracted from the patient using instruments such as forceps. To perform this collection, knob 580 is rotated to an extracted tissue capture mode. The rotation of the knob into the position associated with this mode, results in the rotation of valve member 532 so that bore 540 is aligned with tissue deposit port 489. Slot 544 is aligned with aperture 478. Valve member bore 542 aligns with aperture 478 and tissue deposit port 489 aligned with slot 544. When the valve member 532 is in this position, no suction is drawn through fitting 486. Suction is drawn on the ambient environment through the tissue deposit port 489.

When the system is in the extracted tissue capture mode, the instrument used to extract the tissue is withdrawn from the patient. The distal end of the instrument, with the attached tissue, is inserted into tissue deposit port 489. The suction drawn through port 489 pulls the tissue off the instrument and draws the tissue into tissue trap container 650. As with any tissue drawn into container 650, movement of the tissue out of the container is blocked by tissue filter 600.

Tissue trap 598 is removably coupled to valve assembly 530. Prior to removal of the tissue trap 598, knob 580 is rotated back to the bypass position to remove filter 600 and specimen container 650 from the suction communication path.

Tissue trap 598 is removed from cassette 420 as a single unit. The trap 598 is removed from valve assembly 530 by pulling tissue filter 600 and specimen container 650 horizontally away from valve assembly 530. Another tissue trap 598 can be inserted to collect another tissue sample by pushing the trap container 650 horizontally into recess 587 such that edges 623 and 624 slide into L-shaped rails 592. Knob 580 is then rotated back to the tissue sample collection position in order to collect another tissue sample. Multiple tissue samples may be collected using multiple tissue traps 600.

During this process of removing one tissue trap 598 from the cassette 420 and attaching a new trap 598, there is no need to turn off the suction pump 58. In other words, the new tissue traps 598 can be attached to the cassette 420 without disrupting the suction draw applied to the suction applicator.

A user places cap 680 over tissue filter 600. Cap retainer 683 aligns threads 668 and 682. When cap 680 is rotated relative to specimen container 650, Inner surface 696 of cap 680 contacts top panel 602. Rotation of cap 680 forces tissue filter 600 to move downwardly into compartment 658. Side panel 604 and lip 611 flex inwardly and slide along specimen container panel 652 until distal end 636 contacts bottom panel 653. As tissue filter 600 moves downwardly into compartment 658, pointed tips 698 mounted to bottom panel 653 punctures foil or plastic seal 614 releasing preservative solution 389 to cover tissue sample 398 as seen in FIG. 17.

As cap 680 is rotated onto specimen container 650, tabs 694 break separating cap 680 from cap retainer 683. A user can then pull on arm 685 to remove cap retainer 683 from specimen container 650.

Once the medical/surgical procedure is completed, and use of the mobile unit 30 is no longer required, suction line 50 and irrigation line 51 may be disconnected from fittings 486 and 512, respectively and irrigation coupler 150 may be disconnected from the receptacle 410. Cassette 420 is removed from receptacle 102. After cassette 420 is removed from receptacle 410, door 136 closes passage 118. The closing of the passage 118 substantially eliminates leakage of any waste material remaining in the receptacle 410. Cassette 420 is disposed of as medical waste.

The outlet fitting 158 forms a seal with bottom panel 426 at aperture 510. These components are dimensioned so that, when mated together the outlet fitting 158 presses against bottom panel 426. The compression of these two components against each other forms a substantially fluid tight barrier between these components. Thus, the need to provide an O-ring or other sealing element is eliminated. This simplifies the manufacture of cassette 420.

It should likewise be recognized that in versions of the invention, the plastic from which the tissue filter 600 and specimen container 650 are formed from are at least partially transparent. This provides medical personnel with a quick means to verify that the tissue sample has been collected. Further cassette 420 is formed from materials that are at least partially transparent. This provides medical personnel with a quick means to verify that the cassette has not been previously used and does not contain previously collected waste.

IV. Third Embodiment

A. Receptacle

Figure 24A:
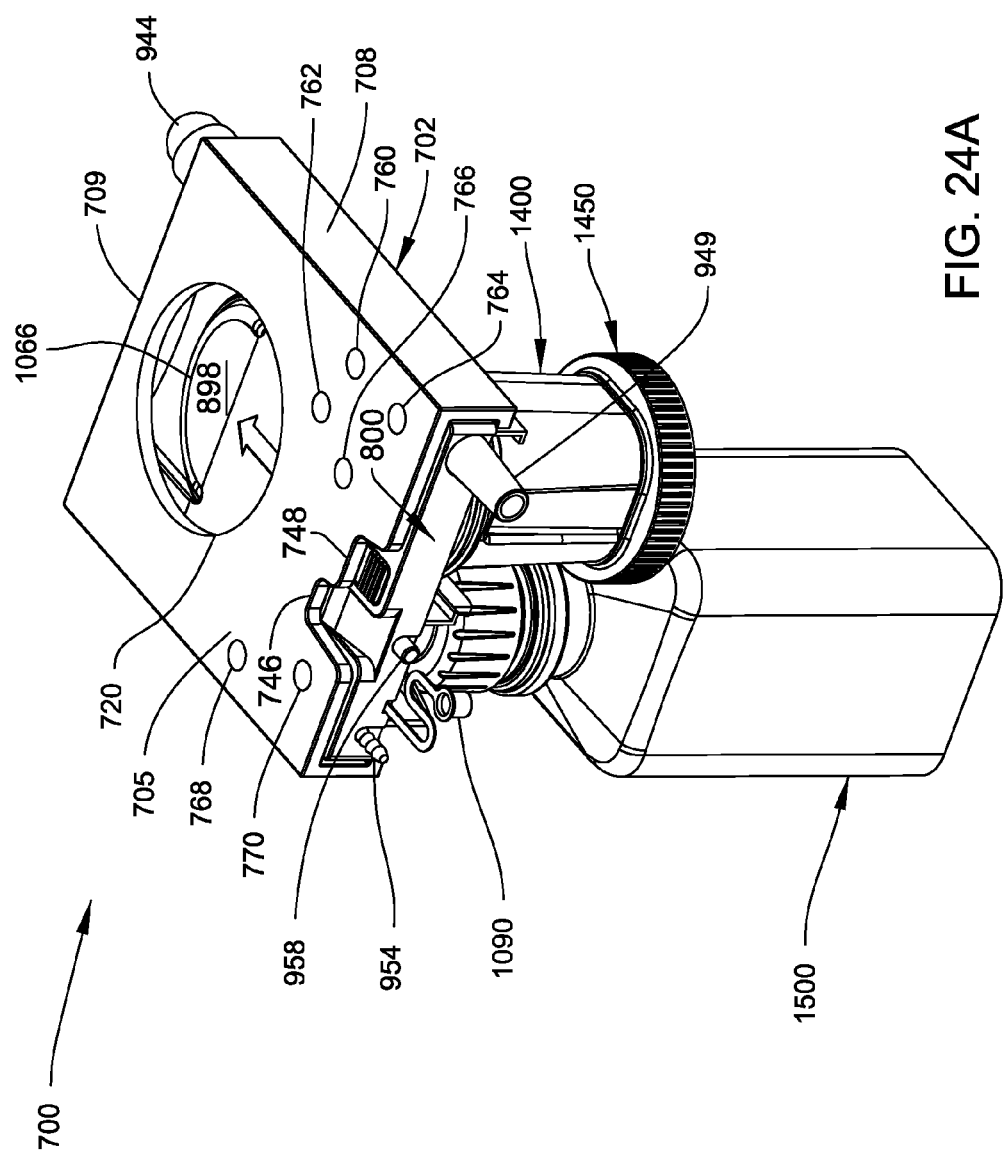
FIG. 24A is a right front perspective view of the manifold assembly of FIG. 23.
Figure 25:
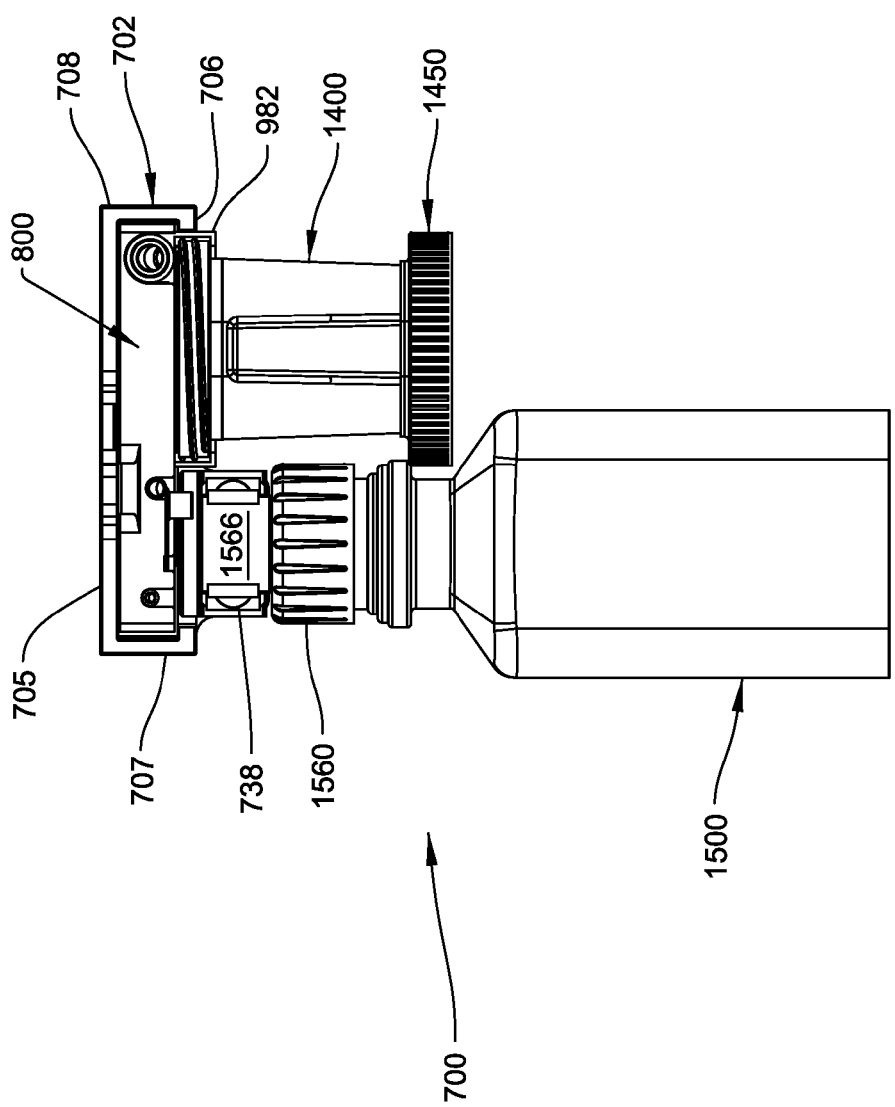
FIG. 25 is a front view of the manifold assembly of FIG. 23.
Figure 29A:
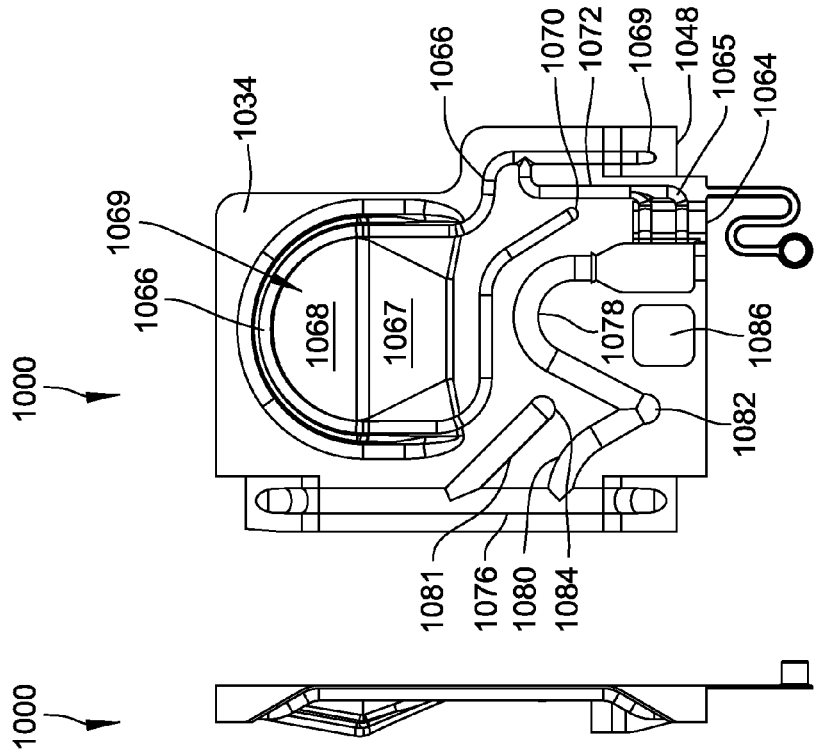
FIG. 29A is a top view of a rubber sheet.
Figure 29B:
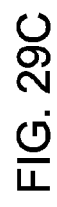
FIG. 29B is a right side view of the rubber sheet.
Figure 29C:
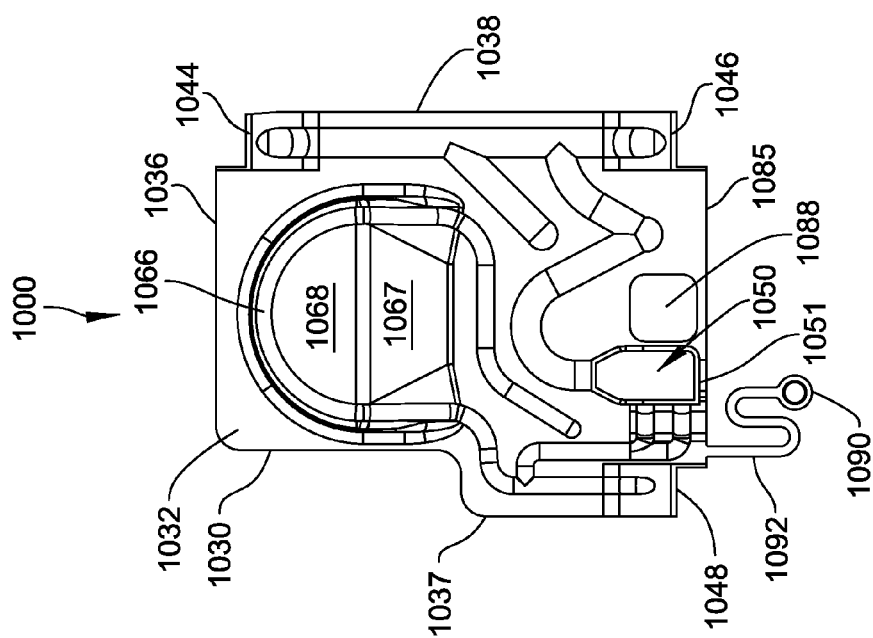
FIG. 29C is a bottom view of the rubber sheet.

Turning to FIGS. 23-25, a third manifold assembly 700 that can be employed as part of the waste and tissue collection system of this invention are illustrated. Manifold assembly 700 comprises a receptacle 702 and cassette 800. Receptacle 702 is shown generally square in shape. Other shapes such as round, oval or square can be utilized.

Receptacle 702 is defined by five exterior panels including parallel and spaced apart generally horizontally oriented top and bottom panels 705 and 706; parallel and spaced apart generally vertically oriented panels 707 and 708; and a generally vertically oriented rear panel 709. Receptacle 702 has a proximal end 710 and a distal end 712. Bottom panel 706 defines a cutout portion 714 that is located towards proximal end 710. Receptacle 702 can be formed from any suitable material such as injection molded plastic.

Receptacle 702 defines a horizontally oriented cavity or passage 716. The cavity or passage 716 extends across the width of receptacle 702 and extends into receptacle 702 to rear panel 709. A generally round opening 720 is defined in top panel 705 towards rear panel 709. Opening 722 extends through rear panel 709 at distal end 712 adjacent to panel 708. A pair of parallel diametrically opposed elongated spaced apart grooves 724 are defined in each of the interior surfaces of panels 707 and 708. Grooves 724 face cavity or passage 716. Top panel 705 defines a pair of adjacent and coextensive notches 746 and 748 at proximal end 710. Notch 746 extends slightly further into top panel 705 than notch 748.

Several holes extend through top panel 705. Holes 760, 762, 764, 766, 768 and 770 pass through top panel 705 into cavity 716. A wax motor or linear actuator 80 is mounted above each of holes 760-770, only one of which is shown in FIG. 24B. One end of rod 81 is connected to actuator 80 and the other rounded end of rod 81 rests on pinch valve 872. Rod 81 extends through top panel 705 to contact pinch valve 872.

Irrigation coupler 730 provides a fluid connection between a source of irrigation liquid such as water bottle 1500 and cassette 800. Irrigation coupler 730 extends away from and below bottom side or surface 706 towards proximal end 710 and adjacent to panel 707. Irrigation coupler 730 has a generally rectangular shaped body 732 with a proximal end 734 and distal end 736. A pair of generally parallel arms 738 extend towards proximal end 734 and define a slot 742 there between. Diametrically opposed grooves 740 are defined in the interior surfaces of each of arms 738 facing slot 742. A finger 744 is located in each arm 738 and extends into groove 740.

B. Cassette

Turning now to FIGS. 26 and 27, details of cassette 800 are illustrated. Cassette 800 is generally rectangular in shape and comprises a housing 822 that has three pieces, an upper housing 824, an opposed lower housing 826 and a rubber sheet 1000 that is disposed between upper housing 824 and lower housing 826. While the housing is illustrated using two pieces, it is contemplated that housing 822 can be formed as a single unitary part. Upper housing 824, rubber sheet 1000 and lower housing 826 are mated together to form housing 822. A cavity 827 is defined within housing 822 between upper housing 824 and lower housing 826.

Upper housing 824 includes a planar top panel 828, front panel 829, back panel 830, and side panels 832, and 834. Panels 828, 829, 830, 832 and 834 extend perpendicularly away from top panel 828. Upper housing 824 has a proximal end 835 and a distal end 836. Tapered sections 837 are defined in each of panels 832 and 834, respectively at distal end 836. Tapered sections 831 guide housing 822 into receptacle 702 during the insertion of cassette 800. Cassette 800 can be formed from any suitable material such as injection molded plastic. In an embodiment, cassette 800 is formed from a material that is transparent.

As shown in FIGS. 26, 27 and 30A-30C, a flexible tab 838 is defined by U-shaped slit 840 in top panel 828. A projection 841 extends upwardly from flexible tab 838 and a series of parallel ribs 842 extend upwardly from flexible tab 838 and are oriented perpendicular to the longitudinal axis of flexible tab 838. Flexible tab 838 is slightly displaced using manual depression applied by a user. An angled face 844 slopes downwardly in top panel 828 adjacent to flexible tab 838 toward front panel 829 and ends approximately in the center of front panel 829 above U-shaped opening 846. Angled face 844 is transparent.

Another U-shaped opening 847 is located in front panel 829 adjacent to panel 834. An additional U-shaped opening 848 is located in front panel 829 adjacent to panel 835. A shallow notch 849 is defined in panel 829 between openings 846 and 848. Yet another U-shaped opening 852 is located in rear panel 830 adjacent to panel 834.

Referring to FIGS. 30A-30C, six pinch valves are defined in top panel 828. The pinch valves are flexible and are be downwardly depressed by a device such as a solenoid or wax motor (not shown). Irrigation supply pinch valve 860 is defined in top panel 828 by a generally U-shaped slit 862. Irrigation supply pinch valve 860 has a downwardly extending finger 864 that faces into cavity 827.

Instruments rinsing irrigation pinch valve 866 is defined in top panel 828 by a generally U-shaped slit 868. Instruments rinsing irrigation pinch valve 860 has a downwardly extending finger 870 that faces into cavity 827.

Suction bypass pinch valve 872 is defined in top panel 828 by a generally U-shaped slit 874. Suction bypass pinch valve 872 has a downwardly extending finger 876 that faces into cavity 827. Tissue collection suction pinch valve 878 is defined in top panel 828 by a generally U-shaped slit 880. Tissue collection suction pinch valve 878 has a downwardly extending finger 882 that faces into cavity 827.

Another tissue collection suction pinch valve 884 is defined in top panel 828 by a generally U-shaped slit 886. Tissue collection suction pinch valve 884 has a downwardly extending finger 888 that faces into cavity 827. Forceps rinse suction pinch valve 890 is defined in top panel 828 by a generally U-shaped slit 892. Forceps rinse suction pinch valve 890 has a downwardly extending finger 894 that faces into cavity 827.

Linear actuators 80 (FIG. 24B) can depress and open the pinch valves. In FIG. 24B, actuator 80 is shown connected to a rod 81 that is in contact with pinch valve 872. Lowering of rod 81 causes finger 876 to contact suction channel 1076. Suction channel 1076 is squeezed between finger 876 and bottom panel 932 such that the flow of fluid through suction channel 1076 is cutoff. Raising of rod 81 causes the lifting of finger 876 from suction channel 1076 allowing flow of fluid through suction channel 1076.

A curved panel portion 896 of top panel 828 defines a recess 897. Curved panel portion 896 begins at rear panel 830 and extends towards dome 898. Semi-circular dome 898 is defined in top panel 828. A semi-circular slot 900 is defined in top panel 828 between dome 898 and curved panel portion 896.

A pair of curving spaced apart panels 902 and 903 extend from slot 900 towards proximal end 835. Panels 902 and 903 are generally parallel to each other and extend perpendicularly away from top panel 828 and define a channel 904. Another pair of spaced apart panels 905 and 906 are located between fingers 864 and 870, respectively. Panel 905 extends perpendicularly from top panel 828 and joins with the proximal end of panel 903 to form channel 908. Panel 906 extends perpendicularly from top panel 828 and curves to end at angled face 844 and together with panel 902 forms channel 910. Panel 911 is located between panels 902 and 906 and is adjacent to angled face 844. Panel 911 extends perpendicularly away from top panel 828. Panels 902, 911 and 906 define a pair of outlets 912 adjacent to angled face 844.

An additional pair of curving spaced apart panels 914 and 916 extends from slot 900 towards finger 870 and terminates at panel 902. Panels 914 and 916 are generally parallel to each other and extend perpendicularly away from top panel 828 and define a channel 917. Generally parallel spaced apart panels 918 and 919 extend substantially between proximal end 835 and distal end 836 adjacent to panel 834. Panels 918 and 919 are generally parallel to each other and extend perpendicularly away from top panel 828 and define a channel 920. Generally curving spaced apart panels 926 and 927 form a V-shape and extend substantially between panel 919 and panel 917. Panels 926 and 927 extend perpendicularly away from top panel 828 and define a channel 928. Channel 928 merges into channel 920. A branch 922 angles off of channel 920 in the direction of finger 888.

Turning now to FIGS. 26, 27 and 28A-28C, Lower housing 826 includes a base panel 930 having a top surface 932, bottom surface 934 and sides 937 and 938. Lower housing 826 has a proximal end 935 and a distal end 936. A post 940 extends perpendicularly from top surface 932 at the corner of side 937 and distal end 936. A wedge shaped column 942 extends perpendicularly from top surface 932 at the corner of side 938 and distal end 936. Fitting 944 extends through column 942. Fitting 944 has a tapered outward facing distal end 945 that contains an annular groove 946 dimensioned to receive O-ring 947.

Another wedge shaped column 948 extends perpendicularly from top surface 932 at the corner of side 938 and proximal end 935. Fitting 949 extends through column 948. Fitting 949 has a tapered outward facing proximal end 950 that is dimensioned to receive suction line 50 (FIG. 1A). An additional wedge shaped column 952 extends perpendicularly from top surface 932 at the corner of side 937 and proximal end 935. Fitting 954 extends through column 952. Fitting 954 has an outward facing distal end 955 that is dimensioned to receive irrigation line 51 (FIG. 1A). A series of cones or barbs 956 surround fitting 954 in order to retain irrigation line 51 to fitting 954. The wider base of barbs 956 face front panel 935.

A fitting 958 extends perpendicularly from front panel surface 935. Recess 960 is defined in top surface 932 directly distal to fitting 958. A generally square stop 962 extends perpendicularly from top surface 932 at proximal end 935 adjacent to recess 960. An angled panel 964 slopes upwardly from top surface 932 at a location adjacent to column 952 and terminates at a location adjacent to stop 962. Angled panel 964 defines groove 990 in bottom surface 934. A recess 963 is defined in bottom surface 934 below stop 962.

Angled panel 967 slopes upwardly from top surface 932 beginning at a location near the center of lower housing 826 and terminating at dome 968. Dome 968 extends distally away from top surface 932. Recess 969 is defined in bottom surface 934 under angled panel 967 and dome 968. Furrow 966 is defined in top surface 932 are extends from column 952, up angled panel 967, around the outer perimeter of dome 968, down angled panel 967 and terminates at aperture 970. Aperture 970 extends through panel 930.

A pair of parallel furrows 965 is defined in and extends along the width of angled panel 964. Another furrow 972 is defined in top surface 932 and extends between furrow 966 and furrows 965. Apertures 974 and 975 are defined in and extend through panel 930. Furrow 976 is defined in top surface 932 and extends between columns 942 and 948. Furrow 976 is coaxial and coextensive with fittings 949 and 945. Furrow 978 is defined in top surface 932 and extends between recess 960 and aperture 974. Furrow 980 is defined in top surface 932 and extends between furrow 976 and aperture 974. Furrow 981 is defined in top surface 932 and extends between furrow 976 and aperture 975.

A U-shaped semi-circular rail 982 extends perpendicularly away from and below bottom surface 934 towards proximal end 935 and adjacent to side 938. Rail 982 has opposing ends 983 and an inward facing lip 984. Rail 982 and bottom surface 934 define recess 985. A rounded boss 986 extends from bottom surface 934 into recess 985 and surrounds aperture 975. A recess 988 is defined in bottom surface 934 between rail 982 and side 937 and surrounds aperture 970.

Turning to FIGS. 26, 27 and 29A-29C, details of flexible sheet 1000 are illustrated. Flexible sheet 1000 is sandwiched between upper housing 824 and lower housing 826. Flexible sheet 1000 can be formed from any suitable flexible material such as rubber or silicone rubber.

Flexible sheet 1000 includes a base panel 1030 having a top surface 1032, bottom surface 1034 and sides 1037 and 1038. Flexible sheet 1000 has a proximal end 1035 and a distal end 1036. An angled section 1042 inclines distally away from top surface 1032 at the corner of side 1038 and distal end 1036. Angled section 1042 overlies column 942. Another angled section 1044 inclines distally away from top surface 1032 at the corner of side 1038 and proximal end 1035. Angled section 1044 overlies column 948. Still another angled section 1048 inclines distally away from top surface 1032 at the corner of side 1037 and proximal end 1035. Angled section 1048 overlies column 952.

An angled panel 1067 slopes upwardly from top surface 1032 beginning at a location near the center of flexible sheet 1000 and terminating at dome 1068. Dome 1068 extends distally away from top surface 1032. Recess 1069 is defined in bottom surface 1034 under angled panel 1067 and dome 1068.

Panels 1051, 1052, 1053 and 1050 extend perpendicularly away from top surface 1032 towards proximal end 1035 and define a instruments rinsing chamber 1050. Panels 1053 and 1052 slope downwardly from panel 1054 to panel 1051. A U-shaped port 1056 is defined in panel 1051.

An irrigation channel 1066 is defined in panel 1030 and opens towards bottom surface 934. Irrigation channel 1066 extends from end 1069 in angled panel 1048, along angled panel 1067, around the outer perimeter of dome 1068, along angled panel 1067 and terminates at end 1070.

A set of parallel irrigation tubes 1065 is defined in panel 1030 and opens towards bottom surface 1034. Irrigation tubes 1065 extend along the width of an angled panel 1064 and terminate in instruments rinsing chamber 1050. Another irrigation tube 1072 is defined in panel 1030 and opens towards bottom surface 1034. Irrigation tube 1072 extends between irrigation tubes 1065 and irrigation channel 1076. Irrigation tubes 1065, 1066 and 1072 are in fluid communication with each other.

Suction tube 1076 is defined in panel 1030 and opens towards bottom surface 1034. Suction tube 1076 extends between angled sections 1044 and 1046. Suction tube 1078 is defined in panel 1030 and opens towards bottom surface 1034. Suction tube 1078 extends between a junction 1082 and instruments rinsing chamber 1050. Suction tube 1080 is defined in panel 1030 and opens towards bottom surface 1034. Suction tube 1080 extends between suction tube 1076 and junction 1082. Instruments rinsing chamber 1050, suction tubes 1076, 1078 and 1080 are in fluid communication with each other. Suction tube 1081 extends between suction tube 1076 and junction 1083. Suction tubes 1076 and 1081 are in fluid communication with each other.

A generally square stop 1086 extends perpendicularly from top surface 1032 at proximal end 1035 adjacent to instruments rinsing chamber 1050. Recess 1088 is defined in bottom surface 1034 below stop 1086. A cap 1090 is connected to a flexible arm 1092. Arm 1092 is connected to proximal end 1035 adjacent to angled panel 1064.

Upper housing 824 and lower housing 826 are mated together with rubber sheet 1000 there between to form housing 822 of cassette 800. Housings 824 and 826 are retained to each other by press-fitting or snap fitting the two housing sections together. In one embodiment, housings 824 and 826 are retained to each other by an adhesive. In the mated position, rubber sheet 1000 is sandwiched between upper housing 824 and lower housing 825. Compressive forces between upper housing 824 and lower housing 826 create a fluid path seal between rubber sheet 1000 and lower housing 826.

Figure 32:
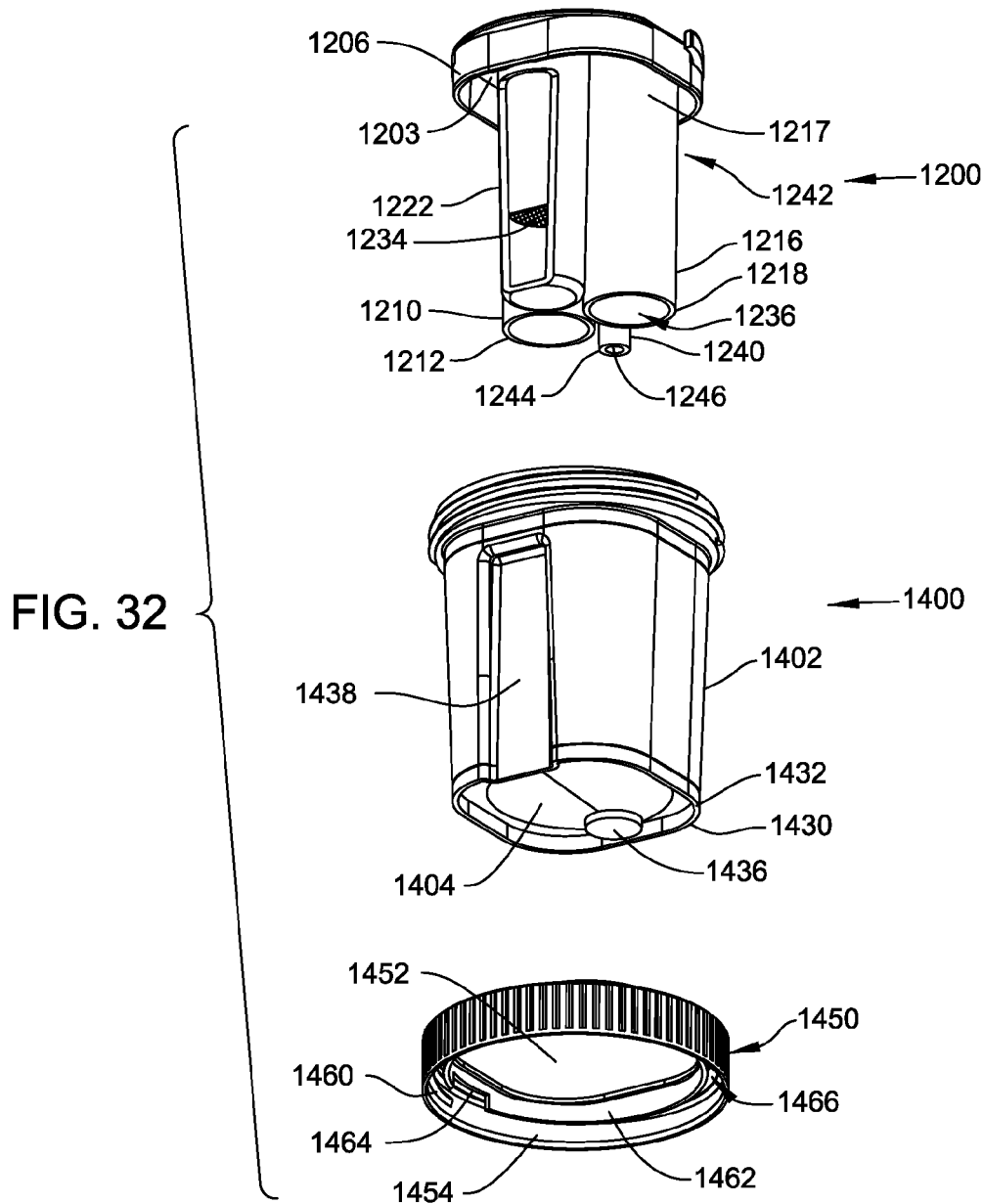
FIG. 32 is an exploded bottom view of the tissue trap and specimen container.

With reference to FIGS. 31 and 32, a tissue trap 1198 is shown. Tissue trap 1198 includes a specimen container 1400 in which a tissue filter 1200 is seated. Tissue filter 1200 is generally cylindrical in shape. Other shapes such as round, oval or square can be utilized. Tissue filter 1200 can be formed from any suitable material such as low durometer plastic or thermoplastic elastomer. Tissue filter 1200 can be formed from a transparent material such that the contents may be viewed by a user.

Tissue filter 1200 is defined by a top panel 1202. Top panel 1202 has a bottom surface 1203 and a top surface 1204. An aperture 1250 is defined in top panel 1202 and is surrounded by a recess 1252. An opening 1254 is defined in top panel 1202. A generally annular side panel 1206 extends perpendicularly away from the peripheral edge of top panel 1202 and bottom surface 1203. Flat portions 1256 are located on opposing sides of annular side panel 1206. A flexible prong or tang 1258 extends outward from each flat portion 1256 and is spaced from each flat portion 1256 by a gap 1260.

A pair of juxtaposed elongated hollow tubes 1210 and 1216 extend in a distal direction away from bottom surface 1203. Tube 1210 has a proximal end 1211 and a distal end 1212. Tube 1216 has a proximal end 1217 and a distal end 1218. Proximal ends 1211 and 1217 are connected to bottom surface 1203. In one embodiment, tubes 1210 and 1216 can contain a preservative solution 389 (FIG. 22D) such as formalin or other suitable preservative solution. In another embodiment, the preservative solution is omitted. Preservative solution 389 is sealed within tubes 1210 and 1216 by a foil or plastic seal 1236.

Another elongated tube 1222 extends in a distal direction away from bottom surface 1203. Tube 1222 has a proximal end 1224 and a distal end 1226. Proximal end 1224 is connected to bottom surface 1203. Bottom panel 1227 is located at the distal end 1126 of tube 1222. An elongated opening 1228 is defined in tube 1222 extending between proximal end 1224 and distal end 1226. Tube 1222 has a cavity 1230. Cavity 1230 is continuous or coextensive with opening 1254. A screen 1234 extends across the diameter of tube 1222 towards distal end 1226. A tissue sample 398 is shown trapped by screen 1234 in FIG. 31.

An elongated duct 1240 extends in a distal direction away from bottom surface 1203. Duct 1240 has a proximal end 1242 (not shown) and a distal end 1244. Proximal end 1242 is connected to bottom surface 1203. Distal end 1244 extends slightly beyond the ends of tubes 1210 and 1216. A bore 1246 is defined in duct 1240 extending between distal end 1244 and aperture 1250.

Specimen container or jar 1400 has a generally square shape with rounded corners. Specimen container 1400 has an outer panel 1402 and a bottom panel 1404. Two planar spaced apart flat grasping sections 1406 are located in outer panel 1402 on opposing sides of specimen container 1400. A compartment 1408 is defined within specimen container 1400. Specimen container 1400 has a top end 1410 and a bottom end 1412. Specimen container 1400 is formed from a transparent material such that the contents of compartment 1408 may be viewed by a user.

An annular flange 1416 extends peripherally outward from panel 1402 at top end 1410. Flange 1416 has an inner face 1418 and an outer face 1420. Annular threads 1422 are defined in the outer face 1420. Two opposing flat sections 1424 are located in inner face 1418. A step 1426 extends from inner face 1418 around the whole circumference of the face. Step 1426 slopes downwardly from flange 1416 towards panel 1402.

A rim 1430 extends peripherally downward away from bottom panel 1404. Rim 1430 has a beveled or angled edge 1432 that slopes inwardly from outer panel 1402. Boss 1436 extends distally away from bottom panel 1404 adjacent to one side of rim 1430. Pointed tip 1437 extends upwardly away from bottom panel 1404 into compartment 1408. A window 1438 is located in outer panel 1402. Window 1438 allows a user to view the contents of compartment 1408.

Circular cap 1450 has a top panel 1452 and an annular side panel 1454 that extends perpendicularly downward from top panel 1452. Knurled ribs 1456 are placed on the outer face of side panel 1454 to allow a user a better grip of cap 1450. A rim 1458 extends perpendicularly upward away from top 1452. Annular threads 1460 are defined on the inner face of side panel 1454. An annular flange 1462 extends perpendicularly away from top panel 1452 parallel to and slightly spaced from side panel 1454. A pair of opposed notches 1464 are defined in flange 1462. Slot 1466 is defined between flange 1462 and side panel 1454.

Cap 1450 is attached to top end 1410 of specimen container 1400 by the rotation of cap 1450 relative to specimen container 1400 to cause the mating of threads 1422 and 1460. Cap 1450 can also be attached to bottom end 1412 of specimen container 1400. Rim 1458 is placed by a user adjacent to rim 1430 and pressed onto rim 1430. Beveled edge 1432 guides rim 1458 into frictional contact with rim 1430 thereby holding cap 1450 to the bottom of specimen container 1400.

An identification device 376 is attached to outer panel 1402. Identification device 376 has the same structure and performs the function as the previously described identification devices.

Tissue sample 398 can be a wide variety of tissue specimens. For example tissue sample 398 can be a biopsy sample from a body location or a polyp from a colon. Tissue filter 1200 will slide into compartment 1408 until prongs or tangs 1258 engage flat section 1424 above step 1426. At this point, step 1426 provides a resistive force to the further insertion of tissue filter 1200 into compartment 1408.

Tissue trap 1198 is removably coupled to cassette 800. Trap 1190 is inserted by pushing tissue filter 1200 and specimen container 1400 horizontally into cavity 985 such that flange 1416 and threads 1422 slide into L-shaped rail 982 and are retained by lip 984. Trap 1198 hangs below cassette 800. Trap 1198 is removed from cassette 800 by pulling tissue filter 1200 and specimen container 1400 horizontally away from cassette 800. Multiple tissue samples may be collected using multiple tissue traps 1200.

A user places cap 1450 over tissue filter 1200. When cap 1450 is rotated relative to specimen container 1400, the inner surface cap top panel 1452 contacts the top panel 1204 of tissue filter 1200. Threads 1422 and 1460 cause the rotation of cap 1450 to force tissue filter 1200 to move downwardly into compartment 1408. Step 1426 causes prongs or tangs 1258 to flex inwardly and slide along specimen container panel 1406 until the bottom edge of panel 1206 abuts step 1426. As tissue filter 1200 moves downwardly into compartment 1408, pointed tip 1437 mounted to bottom panel 1404 punctures foil or plastic seal 1236 releasing preservative solution 389 (FIG. 17) to cover tissue sample 398.

Figure 33:
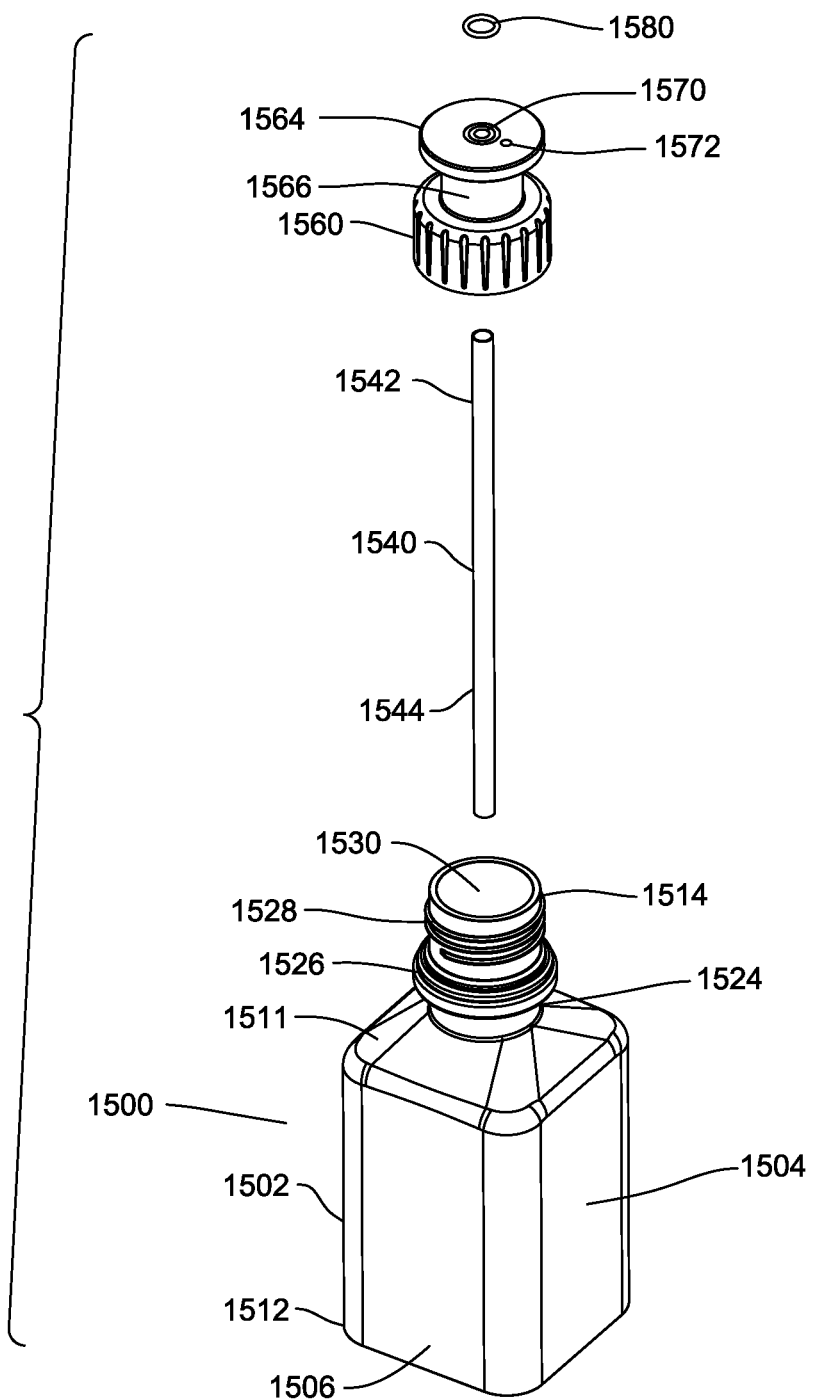
FIG. 33 is an exploded top view of a water bottle.
Figure 34:
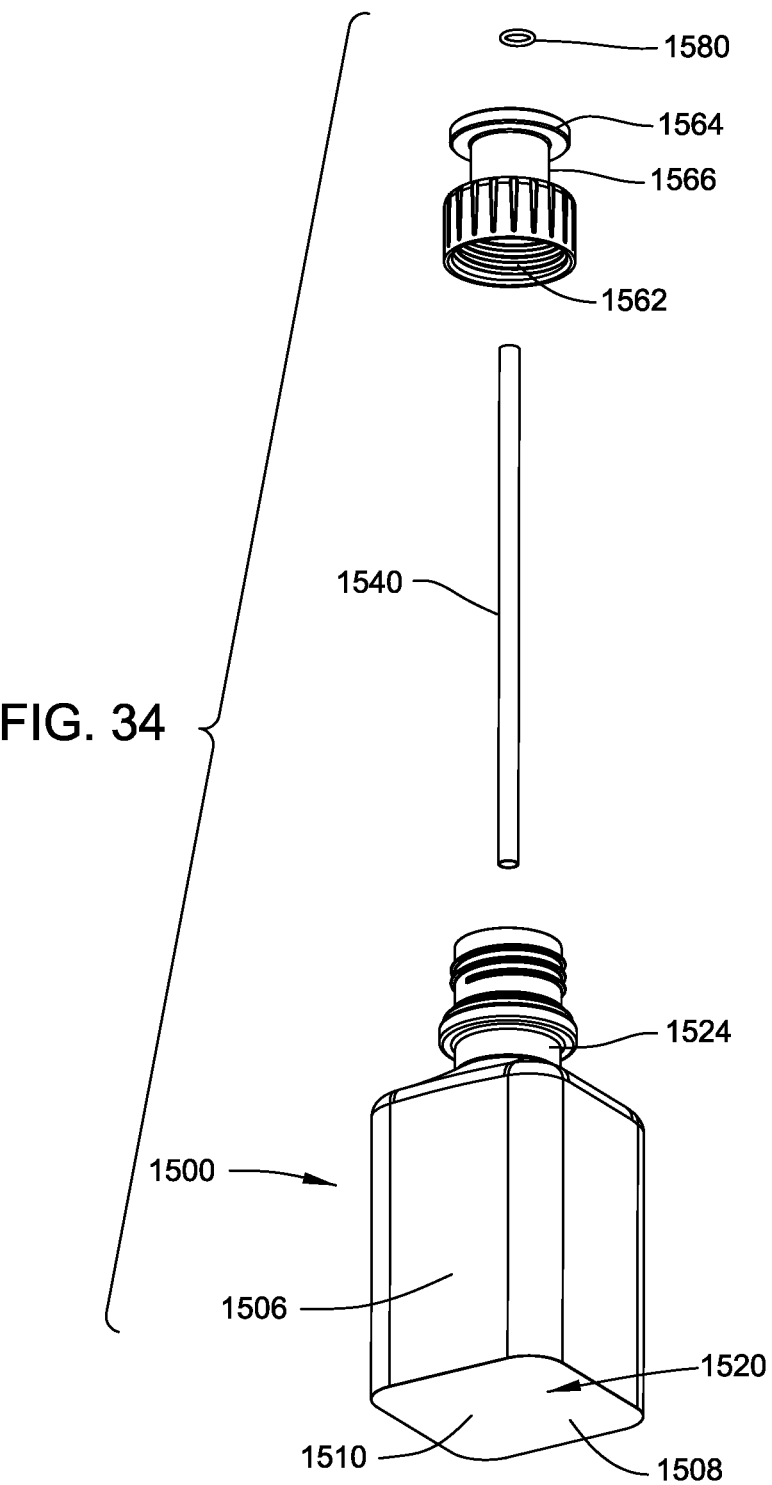
FIG. 34 is an exploded bottom view of the water bottle.

Turning now to FIGS. 33 and 34, a water bottle 1500 is shown. Water bottle 1500 is shown generally rectangular in shape. Other shapes such as round or oval can be utilized. Water bottle 1500 is defined by six exterior panels including opposed parallel and spaced apart generally vertically oriented panels 1502 and 1504; opposed parallel and spaced apart generally vertically oriented panels 1506 and 1508; and a generally horizontally oriented bottom panel 1510. Top panel 1511 is angled upwardly away from side panels 1502, 1504, 1506 and 1508. Side panels 1502, 1504, 1506 and 1508 are perpendicular to bottom panel 1510. Water bottle 1500 has a top end 1514 and a bottom end 1512.

Panels 1502, 1504, 1506, 1508, 1510 and 1511 define a reservoir 1520 within water bottle 1500. Water bottle 1500 can be formed from any suitable material such as blow molded plastic. In one embodiment, water bottle 1500 is formed from a transparent material such that the contents or level of reservoir 1520 may be viewed by a user.

Water bottle 1500 has a neck 1524 that extends away from top wall 1511. An annular flange 1526 encircles neck 1524. Threads 1528 are defined in the outer face of neck 1524 at top end 1514. Opening 1530 allows access to reservoir 1520. An elongated tube 1540 has ends 1542 and 1544. A circular cap 1560 has threads 1562, an annular flange 1564 at one end and a smaller diameter neck 1566. Apertures 1570 and 1572 are defined in flange 1564.

Water bottle 1500 is filled with an irrigation fluid. Water bottle 1500 is assembled by placing tube end 1542 through aperture 1570 of cap 1560 and placing tube end 1544 through opening 1530 into bottle 1500. Aperture 1572 allows the air pressure inside of bottle 1500 and outside of bottle 1500 to equalize such that a vacuum is not formed inside bottle 1500.

Water bottle 1500 is removably coupled to receptacle 702. Water bottle 1500 is inserted by a user manually sliding water bottle 1500 horizontally towards and into slot 742 such that arms 740 flex to grip neck 1566. Water bottle 1500 hangs below cassette 800 supported by flange 1564. Fingers 744 retain and prevent water bottle 1500 from sliding out of slot 742. Water bottle 1500 is removed from cassette 800 by a user manually pulling water bottle 1500 horizontally away from cassette 800 causing arms 740 to flex allowing neck 1566 to slide past fingers 744.

C. Operation

Referring to FIGS. 1A-C, 15B and 23-34, mobile unit 30 (FIG. 1A) is prepared for use by a user inserting the cassette 800 into the complementary receptacle 702 of manifold assembly 700 associated with the canister 38 in which the waste drawn from the surgical site is to be collected. This step is performed by aligning tapered sections 837 of cassette 800 with grooves 724 of receptacle 702 and sliding cassette 800 into passage or cavity 716. Sides 832 and 834 slide along groove 724 until back panel 830 contacts rear panel 709 of receptacle 702. In this position, fitting 944 is seated in and in fluid communication with suction conduit 59 (FIG. 15B). Ribs 842 of flexible tab 838 deflect under front edge 749 of top panel 705. Flexible tab 842 retains cassette 800 within cavity or passage 716.

Peristaltic pump roller 74 is mounted through opening 720 such that peristaltic pump roller contacts irrigation channel 1076. Irrigation channel 1076 is squeezed between peristaltic pump roller 74 and furrow 966 such that the rotation of roller 74 forces irrigation fluid through irrigation channel 1076. Roller 74 and pump motor 71 are mounted at an angle offset from a vertical axis defined perpendicular to top panel 705 to allow roller 74 to freely rotate without contacting dome 898.

RFID reader 194 recognizes identification device 376 such as an RFID tag and sends a signal to controller 192 to allow operation of mobile unit 30 when cassette 800 is seated in receptacle 702.

Water bottle 1500 is attached to receptacle 702 by inserting horizontally into slot 742 such that arms 740 flex to grip neck 1566. Water bottle 1500 hangs below cassette 800 supported by flange 1564. Fingers 744 retain and prevent water bottle 1500 from sliding out of slot 742. In this position, annular flange aperture 1570 is pressed against aperture 970 and is then in fluid communication with irrigation channel 1066.

Tissue filter 1200 and specimen container 1400 are attached to cassette 800 by inserting tissue filter 1200 and specimen container 1400 horizontally into cavity 985 such that flange 1416 and threads 1422 slide into L-shaped rail 982 and are retained by lip 984. Tissue filter 1200 and specimen container 1400 hang below cassette 800.

Mobile unit 30 is completed for use by coupling of an applicator 52 such as a colonoscope to the unit by attaching suction line 50 to fitting 949 and irrigation line 51 to fitting 954. Cap 1090 is initially placed over and sealing second suction fitting 958.

Mobile unit 30 is actuated by activating the suction pump 58 and peristaltic pump 70. The operator uses control panel 196 to select the mode of operation. In the case when the operator selects the bypass mode, pinch valve actuators 80 close pinch valves 884 and 878, respectively while pinch valve 872 remains open. Activation of suction pump 58 results in a waste stream being drawn along a suction fluid communication path 184 from the surgical site into the applicator 52, through the suction line 50 and into fitting 949. This waste stream includes liquid and solid waste to which the suction applicator 52 is applied as well as air adjacent the applicator 52. From fitting 949, the waste stream travels through furrow 976 and suction tube 1076 and through fitting 944 into conduit 59. From conduit 59, the waste stream flows into the associated canister 36 or 38. This mode of operation is referred to as the bypass mode because the suction fluid communication path 184 bypasses tissue filter 1200.

Liquid and solid components of the waste stream that enter the canister 36 or 38 precipitate out of the stream and are held in the canister 36 and 38 for final disposal.

Activation of peristaltic pump 70 results in irrigation fluid being pumped along an irrigation fluid communication path 182 from water bottle 1500, through tube 1540, through aperture 970, furrow 966 and irrigation channel 1076 and fitting 954, irrigation line 51 and into the applicator 52 for application at the surgical site.

A user can elect to collect a tissue sample such as a polyp using cassette 800. Cassette 800 is selected for a mode of operation by the movement of certain pinch valves by actuators 80. The operator uses control panel 196 to select the mode of operation. In the case when the operator selects the tissue collection mode, pinch valves 872 and 890 are closed and pinch valves 884 and 878 are opened.

Mobile unit 30 is re-actuated by re-activating the suction pump 58 and peristaltic pump 70. When the system is in this operational mode, a waste stream along with an entrained tissue sample is drawn along a suction fluid communication path 184 from the surgical site into the applicator 52, through the suction line 50 and into fitting 949. This waste stream includes liquid and solid waste and a tissue sample 398 to which the suction applicator 52 is applied as well as air adjacent the applicator 52.

From fitting 949, the waste stream travels through furrow 976 and suction tube 1076, furrow 980 and suction tube 1080, through aperture 974, cavity 1230, screen 1234, bore 1246, aperture 1250, aperture 975 into furrow 981 and suction tube 1081, furrow 976 and suction tube 1076 and through fitting 944 into conduit 59. From conduit 59, the waste stream flows into the associated canister 36 or 38. Tissue sample 398 is trapped by the screen 1234 within tissue filter 1200. This mode of operation is referred to as the tissue collection mode because the suction fluid communication path 184 travels through tissue filter 1200. It is noted that in order to collect samples in the tissue collection mode, it is not required to disconnect or re-connect the suction line 50.

A user can elect to collect a tissue sample extracted with an instrument using cassette 800 and tissue trap 1198. Cassette 800 is placed in an extracted tissue capture mode by movement of selected pinch valves by actuators 80. The operator uses control panel 196 to place the cassette in this mode. In the extracted tissue capture mode, pinch valves 872 and 878 are closed and pinch valves 884 and 890 are opened. Cap 1090 is removed from fitting 958.

When the system is in the extracted tissue capture mode, a waste stream is drawn along a suction fluid communication path 184 from fitting 958 into instruments rinsing chamber 1050. A user may place tissue sample 398 held by an instrument (not shown) through fitting 958 into instruments rinsing chamber 1050. The tissue sample is viewed within instruments rinsing chamber 1050 through transparent angled face 844.

The operator uses control panel 196 to regulate the supply of irrigation fluid. Irrigation fluid is supplied to instruments rinsing chamber 1050 by the opening of pinch valve 866 by one of actuators 80. Pressurized irrigation fluid flows from irrigation channel 1076 through irrigation tubes 1072 and 1065 into instruments rinsing chamber 1050 allowing rinsing of tissue samples placed into instruments rinsing chamber 1050.

From fitting 949, the tissue sample, and waste stream travels through furrow 978 and suction tube 1078, through aperture 974, cavity 1230, screen 1234, bore 1246, aperture 1250, aperture 975 into furrow 981 and suction tube 1081, furrow 976 and suction tube 1076 and through fitting 944 into conduit 59. From conduit 59, the waste stream flows into the associated canister 36 or 38. Tissue sample 398 is trapped by the screen 1234 within tissue filter 1200. This mode of operation is referred to as the forceps sample collection mode because the suction fluid communication path 184 travels through instruments rinsing chamber 1050 and tissue filter 1200.

In order to remove the tissue trap 1198, the operator first uses control panel 196 to return the mode of operation of mobile unit 30 to the bypass mode. This causes the suction communication path to be removed from tissue trap 1198. Tissue filter 1200 and specimen container 1400 are removed from cassette 800 by pulling tissue filter 1200 and specimen container 1400 horizontally away from cassette 800 causing specimen container 1400 to slide out along rails 982. Another tissue filter 1200 and specimen container 1400 are inserted to collect another tissue sample by pushing tissue filter 1200 and specimen container 1400 horizontally into cavity 985 along rails 982. Tissue trap 1198 is inserted and removed from cassette 800 as a single unit.

During this process of removing one tissue trap 1198 from the cassette 800 and attaching a new trap 1198, there is no need to turn off the suction pump 58. In other words, the new tissue traps 1198 can be attached to the cassette 800 without disrupting the suction draw applied to the suction applicator.

In order to collect another tissue sample, the operator uses control panel 196 to return the mode of operation of mobile unit 30 to the tissue sample collection mode.

A user places cap 1450 over tissue filter 1200. When cap 1450 is rotated relative to specimen container 1400, the inner surface of cap top panel 1452 contacts the top panel 1204 of tissue filter 1200. Threads 1422 and 1460 cause the rotation of cap 1450 to force tissue filter 1200 to move downwardly into compartment 1408. Wall 1462 causes prongs or tangs 1258 to flex inwardly and slide along specimen container panel 1406 until the bottom edge of panel 1206 abuts step 1426. As tissue filter 1200 moves downwardly into compartment 1408, pointed tip 1437 mounted to bottom panel 1404 punctures foil or plastic seal 1236 releasing preservative solution 389 (FIG. 17) to cover tissue sample 398.

Once the medical/surgical procedure is completed, and use of the mobile unit 30 is no longer required, suction line 50 and irrigation line 51 are disconnected from fittings 949 and 958, respectively. Flexible tab 838 is manually depressed and cassette 800 is manually removed by pulling cassette 800 from receptacle 702. Cassette 800 is then disposed of as medical waste.

After use, the mobile unit 30 is coupled to a docker (not illustrated and not part of this invention.) Waste material in the canister 36 or 38 is flowed through the docker to a treatment facility.

It should likewise be recognized that in versions of the invention, the plastic from which the tissue filter 1200 and specimen container 1400 are formed from are at least partially transparent. This provides medical personnel with a quick means to verify that the tissue sample has been collected. Further cassette 800 is formed from materials that are at least partially transparent. This provides medical personnel with a quick means to verify that the cassette has not been previously used and does not contain previously collected waste.

The present invention allows for a suction fluid communication path to be selectively routed into and out of a tissue sample container.

V. Fourth Embodiment

A. Receptacle

FIGS. 35-42 illustrate an alternative cassette 1700 for use with the alternative manifold receptacle 1699 that may be part of collection system 30 of FIG. 1A. Manifold receptacle 1699, sometimes referred to as a manifold receiver, is disclosed in detail in the incorporated by reference U.S. Pat. No. 7,615,037.

Figure 35:
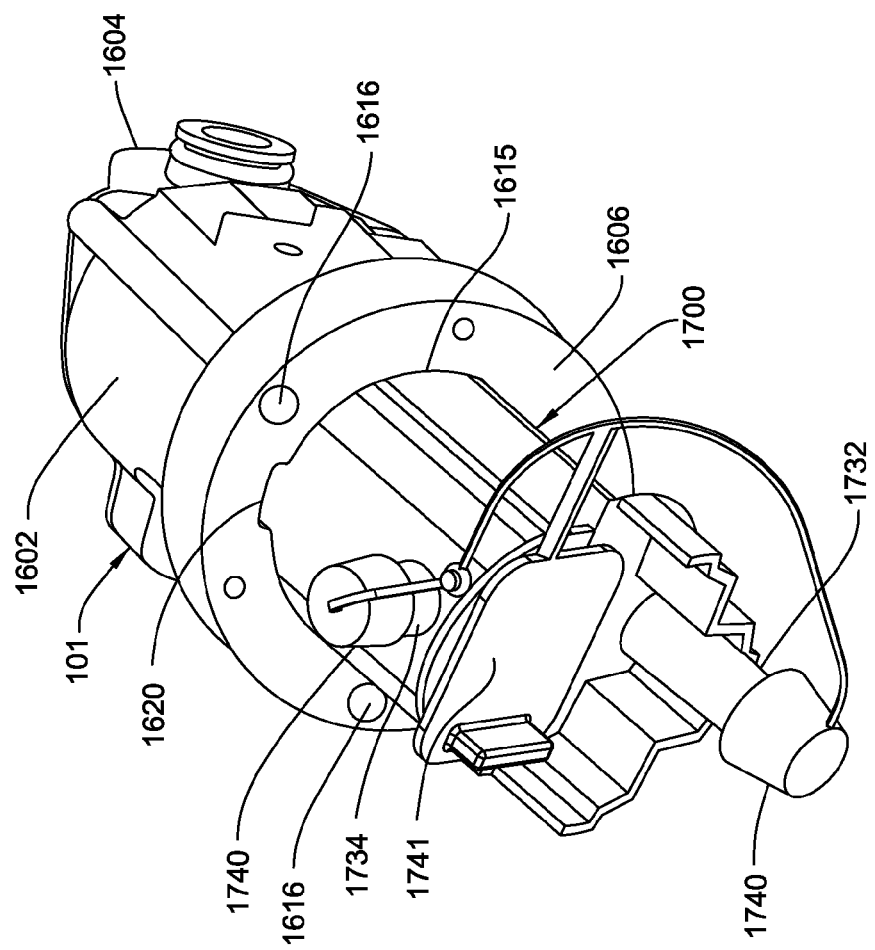
FIG. 35 is a perspective view of another embodiment of a manifold assembly showing a cassette seated in a receptacle.
Figure 36:
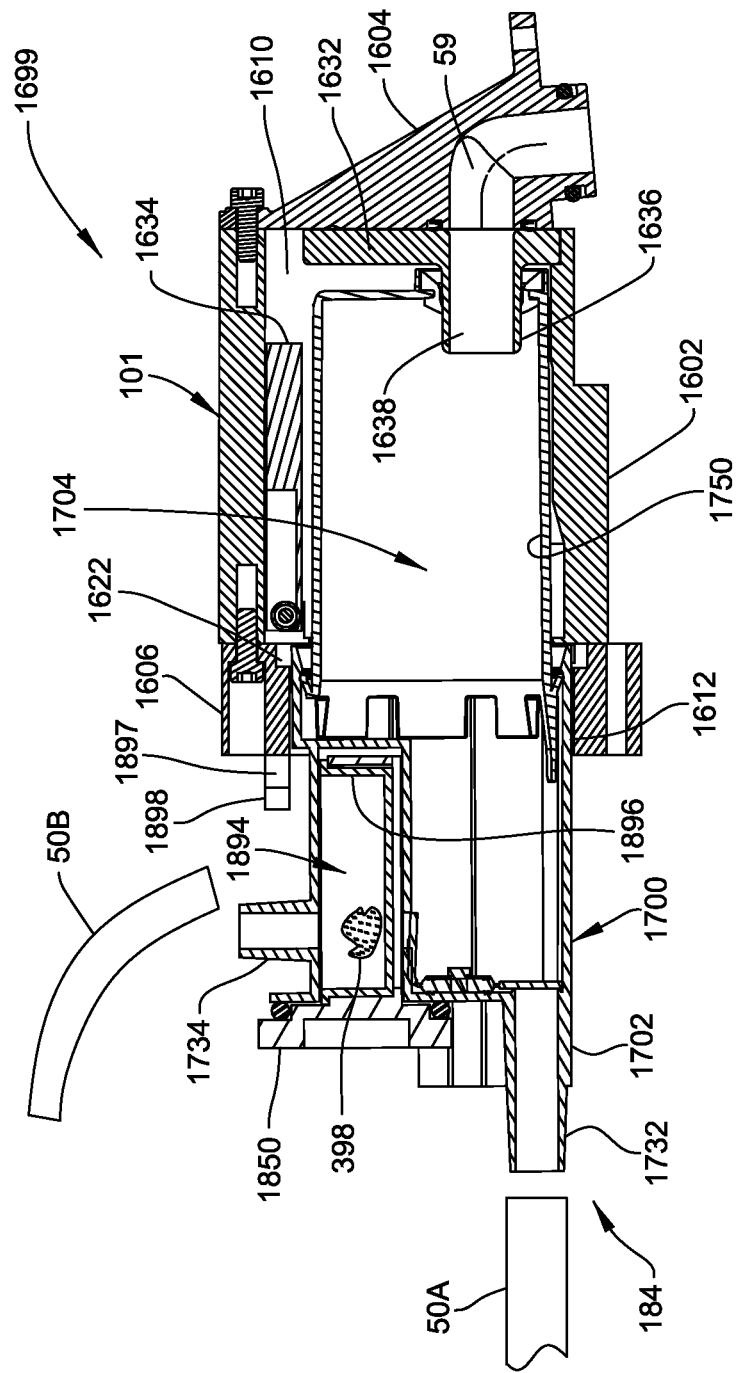
FIG. 36 is a cross-sectional view of the manifold assembly of FIG. 35 with the cassette seated in a receptacle.
Figure 40C:
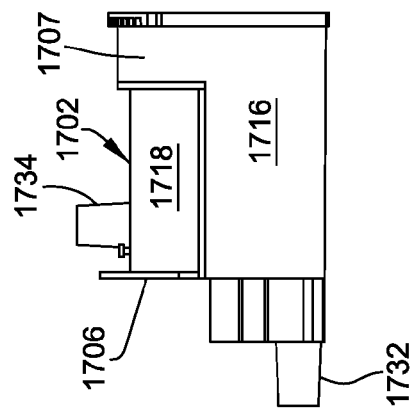
FIG. 40C is a right side view of the cassette cap.
Figure 40E:
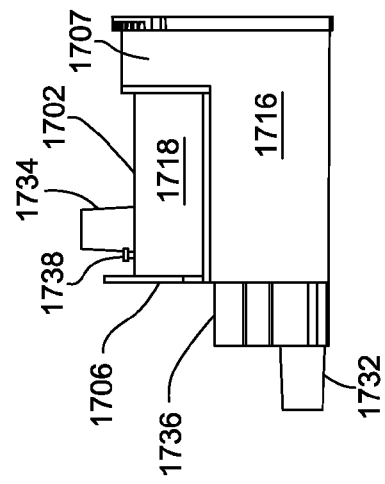
FIG. 40E is a left side view of the cassette cap.
Figure 40B:
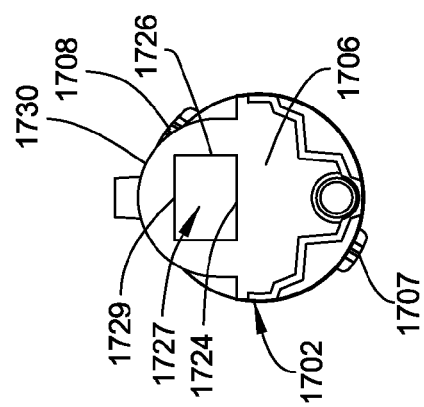
FIG. 40B is a front view of the cassette cap.
Figure 42A:
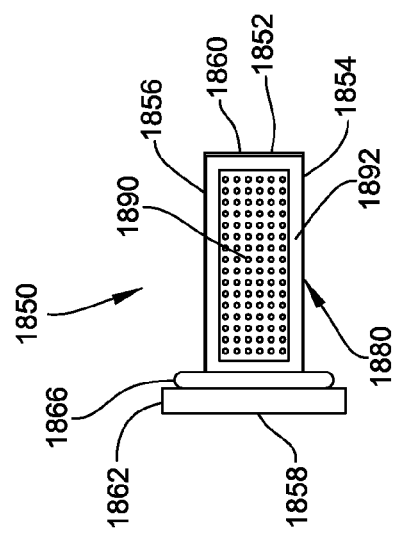
FIG. 42A is a top view of a tissue trap.
Figure 42D:
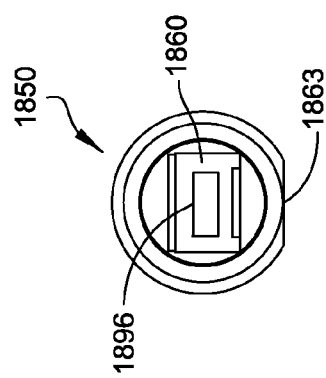
FIG. 42D is a rear view of the tissue trap.
Figure 42C:
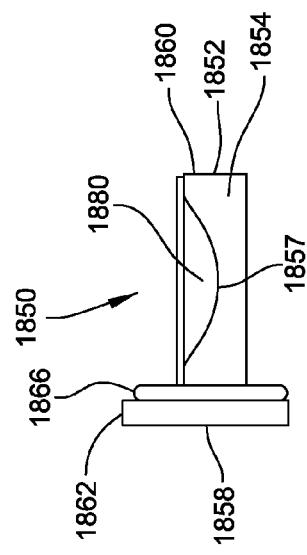
FIG. 42C is a right side view of the tissue trap.
Figure 42E:
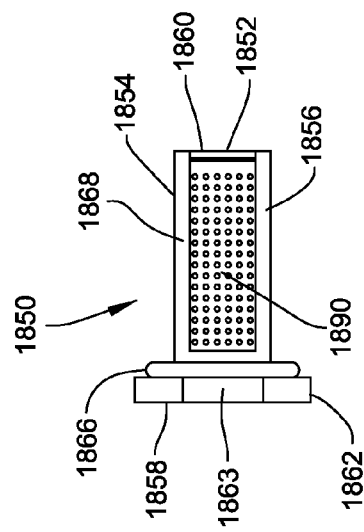
FIG. 42E is a left side view of the tissue trap.
Figure 42B:
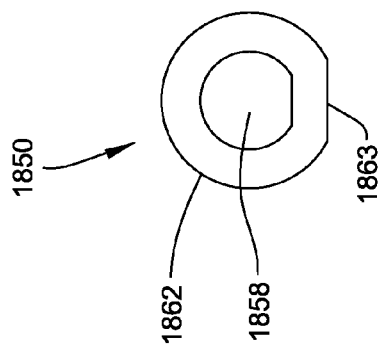
FIG. 42B is a front view of the tissue trap.
Figure 44:
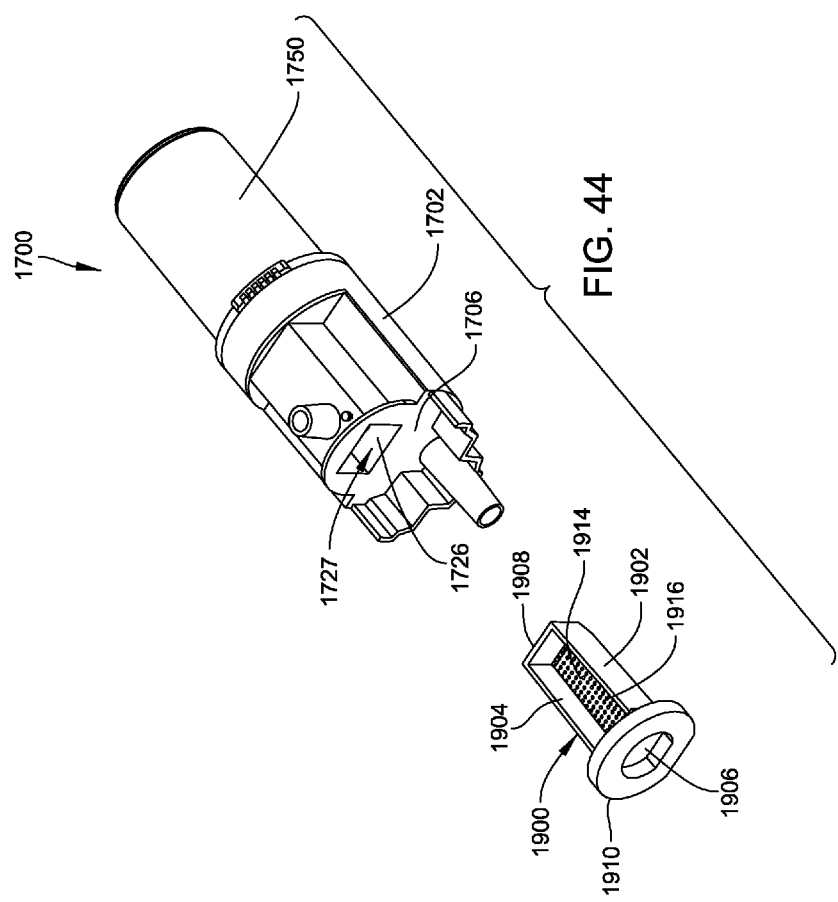
FIG. 44 is a perspective exploded view of an additional embodiment of a manifold assembly.
Figure 45A:
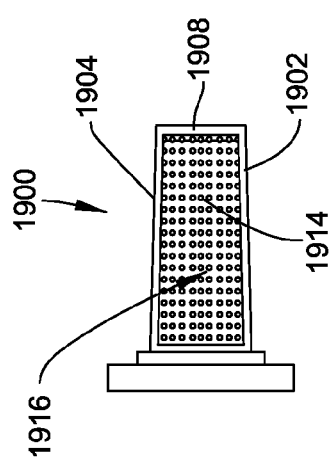
FIG. 45A is a top view of the tissue trap of FIG. 44.
Figure 45D:
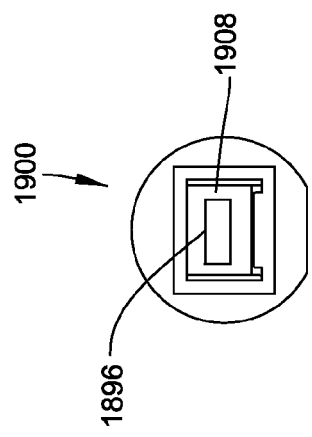
FIG. 45D is a rear view of the tissue trap of FIG. 44.

With specific reference to FIGS. 35 and 36, manifold receptacle 1699 comprises three primary static components. A housing 1602 that receives the proximal end of the cassette 1700. A receiver adaptor 1604 that holds the manifold receptacle housing 1602 to the associated canister cap 40 (FIG. 1A). Adaptor 1604 also includes a conduit 59 that functions as the flow path from the manifold housing 1602 into the associated canister 36. A lock ring 1606 is attached to the distal front end of manifold housing 1602. Lock ring 1066 is formed with geometric features to ensure that, when a cassette 1700 is fitted in receptacle 1699, the cassette 1700 is properly aligned.

Housing 1602 is formed to define co-axial passages or bores 1610 and 1612 that extend through housing 1602. At the distal end, a spring loaded door 1634 is mounted to housing 1602 that can selectively be opened by the insertion of cassette 1700 and closed by the removal of cassette 1700.

Conduit 59, the conduit that provides a fluid communication path from the housing 1602 to the associated canister 36, is elbow shaped, so as to have a bend between 80 and 90 degrees. The distal end of conduit 59 extends into cassette 1700.

Lock ring 1606, is generally ring shaped and has a centrally located through opening 1615. A number of bores 1616 extend longitudinally through the ring. Bores 1616 receive fasteners used to hold the lock ring 1606 to the manifold housing 1602. The lock ring 1606 is further formed to define a pair of slots 1618 (located behind cassette 1700 in FIG. 35) and 1620. Slots 1618 and 1620 are contiguous with through opening 1615 and extend radially outwardly from opening 1615 to the proximal end of the lock ring 1606. Slots 1618 and 1620 are diametrically opposed and have different arcuate profiles. Slot 1618 subtends an arc that is greater than the arc subtended by slot 1620.

Both of slots 1618 and 1620 extend the length of the lock ring 1606. At the proximal end, lock ring 1606 is further formed to have a pair of grooves 1622. Each groove is arcuately shaped and is formed in the inner portion of the lock ring. Each groove 1622 is also contiguous with one of slots 1618 or 1620. Grooves 1622 are generally diametrically opposed to each other. Owing to the abutment of the proximal end of the lock ring 1606 against the distally directed face of the housing 1602, grooves 1622 function as slots through which tabs integral with the cassette 1700 travel as will be described later in more detail.

A valve disk 1632 normally covers the opening into conduit 59. A spring loaded door 1634 extends over the distal end opening into the bore 1610 of housing 1602 when a cassette 1700 is not inserted.

Manifold receptacle 1699 is constructed so that, when the valve disk 1632 is in a specific rotational position within the housing 1602, the valve disk 1632 covers the opening into conduit 59. Valve disk 1632 is rotatable to align bore 1638 with the conduit 59.

B. Cassette

With additional reference now to FIGS. 37-39, the major components of cassette 1700 are shown. Cassette 1700 comprises a housing 1701 having a proximal shell 1750 with a distal attached cap 1702. Shell 1750 is open ended with cap 1702 covering the open end. Shell 1750 and cap 1702 can be formed from a suitable material such as injection molded plastic. Internal to cassette 1700 and housing 1701 is a chamber or void space 1704 (FIG. 38B).

Turning to FIGS. 41A-E, shell 1750 has a generally cylindrical shape. The shell 1750 is formed to have a circular proximal end or base 1752 from which a tubular shaped side wall 1754 upwardly extends. A lip 1756 extends circumferentially around the open top end of side wall 1754. Lip 1756 projects radially outwardly. Two fingers 1761 and 1762 and a tab 1763 extend distally upward from the top of side wall 1754. Each finger 1761 and 1762 has an arcuate cross sectional profile. Finger 1761 subtends a relatively large arc. Finger 1762 subtends a relatively short arc.

An opening 1770 is formed in the shell base 1752. The opening is dimensioned to receive a boss integral with valve disk 1632. The shell is formed so that opening 1770 is centered along an axis that is off center to the longitudinal axis of the shell 1750. A circular lip 1772 extends downwardly from the shell base 1752 around opening 1770. Lip 1772 is spaced radially away from the annular section of the shell base 1752 that defines the outer perimeter of opening 1770.

A drip stop 1774 is fitted in manifold opening 1770. Drip stop 1774 is formed from a compressible, elastomeric material such as polyisoprene rubber. Drip stop 1774 has a pair of lips 1775 with a slit or slot 1790 therebetween. Slot 1790 allows conduit 59 to slide through drip stop 1774 into chamber 1704 forming part of a suction fluid communication path. When cassette 1700 is removed from receptacle 1699, drip stop 1774 blocks the flow of any material out from opening 1770.

FIGS. 40A-E show details of cassette cap 1702. Cap 1702 is formed from a single piece of polypropylene or similar plastic. Cap 1702 has ends 1705 and 1706 and a cylindrical tube shaped skirt 1707. Cap 1702 is sized to allow the housing 1701 to be disposed in and rotated into receptacle 1699. At the proximal end 1705 of the skirt 1707, two tabs 1708 and 1709 project radially outwardly. Tabs 1708 and 1709 are diametrically opposed from each other. The tabs subtend different arcs. Tab 1708 subtends a relatively large arc; this tab is designed to slip fit into manifold receptacle lock ring slot 1618. Tab 1709 subtends a shorter arc; this tab is designed to slip fit into manifold receptacle lock ring slot 1620.

Cap skirt 1707 is formed to have an inwardly tapered rim 1710 at end 1705. Adjacent to rim 1710, skirt 1707 has an outwardly extending step 1712 that extends circumferential around the interior of the skirt. Cap 1702 is dimensioned so that the inner diameter of skirt 1707 above step 1712 is less than the outer diameter of shell lip 1756 by approximately 0.5 mm. When cassette 1700 is assembled, shell 1750 is inserted into cap 1702 such that lip 1756 is compressed and then seated on step 1712. The compression of the inner surface of the cap skirt 1707 around the lip 1756 substantially eliminates loss of suction between the cap and the skirt.

A number of ribs extend inwardly from the inner surface of the skirt 1707 and are located above step 1712. There are two pairs of adjacent ribs 1713 and another pair of adjacent ribs 1714. Ribs 1713 are arcuately spaced apart from each other a sufficient distance from each other to allow shell fingers 1761 to be slip fitted therebetween. Ribs 1714 are spaced apart a sufficient distance so that tab 1763 and not fingers 1761 can be slip fitted therebetween. Shell fingers 1761 and tab 1763 and rib pairs 1713 and 1714 thus facilitate the proper alignment of cassette shell 1750 and cassette cap 1702 when these components are assembled together.

A half barrel 1716 extends distally from the lower half of skirt 1707 and a rectangular shaped housing or box 1718 extends distally from the upper half of skirt 1707. A semicircular face 1719 extends over the top end of skirt 1707 and another semi-circular face 1720 extends over the top end of barrel 1716. Face 1720 is formed so as to have a center-located bore 1721 and a fitting 1734 located toward the bottom of face 1720. Fitting 1734 has a through bore 1722 is in fluid communication with chamber 1704. A planar wall 1724 (best seen in FIG. 38B) extends between face 1719 and face 1720. A circular aperture 1725 (FIG. 38B) extends through wall 1724 adjacent to face 1720.

Housing or box 1718 defines a rectangular shaped sleeve 1726 that defines a closed end bore 1727. The base of the sleeve 126 is defined by wall 1724. An opening 1729 is formed in the face of end cap 1706 where the bore defining sleeve 1726 extends inwardly from the cap. An inlet fitting 1734 extends from the top of housing 1718. The bore 1728 of fitting 1738 is in fluid communication with bore 1727. Specifically, bore 1728 opens into an interior surface of sleeve 1726 that is opposite the surface of wall 1724. A semi-circular rim 1730 extends radially outward from housing 1718. Rim 1730 is coplanar and contiguous with the planar face of cap end 1706.

Fittings 1732 and 1734 are sized to receive a suction line 50.

A generally U-shaped half flange 1736 extends away from the end of barrel 1716. A post 1738 extends perpendicularly away from the top of box 1718 and slightly spaced from rim 1730 and fitting 1734.

With reference to FIGS. 37A and 37B, removable caps 1740 are provided for fittings 1732 and 1734. A removable cover 1741 is provided to cover opening 1729 of sleeve 1726. Cover 1741 has a handle 1742 that can be grasped by a user and a portion that fits into sleeve 1726. Each fitting cap 1740 and cover 1741 is integrally attached to cassette cap 1702 by a tether 1744 with several arms 1746. Arms 1746 are anchored to post 1738.

Cassette 1700 includes a flapper valve unit 1800, now described by reference to FIGS. 38B, 38C and 38D. Flapper valve unit 1800 is formed from a single piece of compressible, flexible material such as polyisoprene or other elastomeric material. Flapper valve unit 1800 has a disk shaped hub 1802. Hub 1802 is formed with a center through hole 1804.

The flapper valve unit 1800 is mounted to face 1720 of cassette cap 1702. A post 1806 is inserted through hole 1804 and into bore 1721 of face 1720. The post 1806 is heat staked to face 1720 thereby holding flapper valve unit 1800 to cassette cap 1702.

The flapper unit hub 1802 also has a number of annular ribs 1810 and 1812. One rib 1810 extends outwardly from the opposed distally and proximally directed faces of hub 1802. One rib 1812 also extends outwardly from each of the opposed faces of hub 1802. Ribs 1810 are located proximal to hub through hole 1804. Ribs 1812 surround ribs 1810. Each rib 1810 and 1812 has an inwardly angled cross sectional profile. Thus, each rib 1810 and 1812 extends outwardly from the hub face and is angled so as to be directed to the longitudinal axis through hub hole 1804.

Flapper valves 1814 are pivotally connected to and extend from hub 1802. Each flapper valve 1814 covers a separate one of the fitting ports 1722 and aperture 1725. A hinge 1816, also an integral part of the flapper valve unit 1800, pivotally connects each flapper valve 1814 to the hub 1802. Hinges 1816 are formed out of sections of the material from which the valve is formed and have a thinner cross sectional thickness than the adjacent hub 1802 and flapper valve 1800. It should be appreciated that the valve 1814 that covers port 1722 is normally generally planar to hub 1802. The valve 1814 that covers aperture 1725 is at an angle, here a right angle, to hub 1802.

Each flapper valve 1814 is generally disk shaped. Each flapper valve 1814 is dimensioned to cover both the associated port 1722 and aperture 1725 and to abut over the area that surrounds the ports. Generally each flapper valve 1814 has a diameter that is approximately 4 mm greater than the inner diameter of the associated port 1722 and aperture 1725. Thus one flapper valve 1814 abuts face 1720 and the other flapper valve 1814 abuts the bottom of wall 1724. Flapper values 1814 act as one way valves allowing fluid flow from port 1722 and aperture 1725 into chamber 1704 and preventing fluid flow from chamber 1704 into port 1722 and aperture 1725.

With reference to FIGS. 39A, 39B, 42A-42E and 43, details of tissue trap 1850 are illustrated. Tissue trap 1850 is generally rectangular in shape. Other shapes such as round, oval or square can be utilized. Tissue trap 1850 can be formed from any suitable material such as low durometer plastic or thermoplastic elastomer. Tissue trap 1850 comprises a holder 1852 and a catch tray 1880. Holder 1852 is defined by four panels including parallel and spaced apart generally vertically oriented side beams 1854 and 1856 and parallel and spaced apart generally vertically oriented front and rear beams 1858 and 1860. Side beams 1854 and 1856 have a curving lowered top edge 1857 toward the center of beams. A circular flange 1862 extends peripherally outward from the front beam 1858 and has a flat section or edge 1863 on a lower portion. Holder 1852 defines a hollow slot 1864 therethrough. Holder 1852 and catch tray 1880 can both be formed from injection molded plastic. In an embodiment, the plastic can be transparent such that a user may view the contents of tissue trap 1850.

A circular O-ring 1866 abuts the proximal face of flange 1862. O-ring 1866 provides a seal between flange 1862 and cap end 1706 when tissue trap 1850 is inserted into bore 1727. In one embodiment, O-ring 1866 can be omitted. In this embodiment, a seal is formed directly between flange 1862 and cap end 1706.

Holder 1852 includes a pair of parallel juxtaposed rails 1868 that extend perpendicularly inward from the bottom interior surface of side panels 1854 and 1856 into slot 1864.

A filter or catch tray 1880 is removably coupled to tissue trap 1850. Catch tray 1880 is generally rectangular in shape and is defined by four walls and a bottom mesh. Catch tray 1880 includes parallel and spaced apart generally vertically oriented side walls 1882 and 1884 and parallel and spaced apart generally vertically oriented front and rear walls 1886 and 1888. A bottom mesh or screen 1890 is mounted to the bottom of walls 1882-1888. Walls 1882-1888 and screen 1890 form an open ended shell (not identified) that defines a cavity 1894. Mesh 1890 contains holes such that a fluid passes through mesh 1890. A lip 1892 extends peripherally outward from top of walls 1882-1888.

Filter or catch tray 1880 can be inserted into and removed from holder 1852. Filter or catch tray 1880 is placed into holder 1852 by inserting catch tray 1880 into slot 1864 and pressing on catch tray 1880 until the bottom of walls 1882-1888 abut rails 1868 and lip 1892 rests on the top of walls 1882-1888. Filter or catch tray 1880 is removed from holder 1852 by lifting catch tray 1880 out from slot 1864.

An identification device 1896 is attached to rear panel 1860 of tissue trap 1850. Identification device 1896 can be any suitable identification device such as a radio frequency identification (RFID) tag or device, a bar code, a magnet or other device. The presence of identification device 1896 can be sensed by a sensor 1897 (FIG. 36) that is mounted in receptacle 1699. In one embodiment, sensor 1897 can be a hall-effect sensor. Sensor 1897 is used to detect the insertion of a tissue trap 1850 into cassette 1700 and to turn on light 1898 (FIG. 36) such that the interior of tissue trap 1850 is illuminated.

An alternative version or embodiment of a tissue trap 1900 is shown in FIGS. 44 and 45A-45E. Tissue trap 1900 is a single unitary piece. Tissue trap 1900 is generally rectangular in shape. Other shapes such as round, oval or square can be utilized. Tissue trap 1900 can be formed from any suitable material such as low durometer plastic or thermoplastic elastomer. Tissue trap 1900 is defined by four panels including parallel and spaced apart generally vertically oriented side panels 1902 and 1904 and parallel and spaced apart generally vertically oriented front and rear panels 1906 and 1908. A circular flange 1910 extends peripherally outward from the front panel 1906 and has a flat section or edge 1912 on a lower portion. In the embodiment of tissue trap 1900 the use of an O-ring is omitted. A screen 1914 is mounted to the bottom of panels 1902-1908 and forms the bottom of tissue trap 1900. Screen 1914 contains holes such that a fluid may pass through screen 1914. Panels 1902-1908 and screen 1914 define a cavity 1916. An identification device 1896 is attached to rear panel 1908 of tissue trap 1900.

In these versions of the invention flange 1910 serves as the cap that covers the opening 1727 in the manifold. In these versions of the invention when there is no need to collect a specimen, a cap, essentially flange 1910 without the attached screen 1914 is seated in the outlet opening. Fluid then flows from the outlet opening through space 1727 without any filtering or collection of entrained tissue. When there is a point in the procedure in which it is useful to collect a specimen, the tissue trap 1900 is inserted in the void space. The tissue entrained in the waste stream is captured by screen 1914.

C. Operation of the Fourth Embodiment

Referring to FIGS. 1A-C, 35-38 and 43, mobile unit 30 (FIG. 1A) is prepared for use by a user inserting the cassette 1700 into the complementary receptacle 1699 associated with the canister 36. A user grasps the cap 1702 and inserts the cassette 1700 into the receptacle 1699 so that shell base 1752 opens door 1634 and slides into chamber 1610. Shell base is directed to the valve disk 1632. For mobile unit 30 to function, valve disk boss 1636 must seat in shell opening 1770. Lock ring slots 1618 and 1620 and manifold tabs 1708 and 1709 cooperate to ensure this alignment of the cassette 1700 to the valve disk 1632. Specifically, these components are positioned so positioning of manifold tab 1608 in slot 1618 results in the cassette 1700 being rotationally positioned so that shell opening 1770 is aligned with valve disk boss 1636. After the cassette is so positioned, continued insertion of cassette 1700 into receptacle 1699 results in shell base 1752 fitting over the valve disk boss 1636.

Cassette 1700 is then rotated causing the like rotation of the valve disk boss 1636 and the valve disk 1632. This rotation places valve bore 1638 in registration with the distal end opening into conduit 59 allowing fluid communication between chamber 1704 and conduit 59.

Initially when the cassette is seated in the receptacle 1699 the distal end of the cassette shell seats over valve boss 1636. More particularly, the boss 1636 extends into shell opening 1770. Drip stop 1774 forms a fluid tight barrier between the boss 1636 and the surrounding section of shell base 1750 that defines opening 1770.

Two suction lines can be attached to cassette 1700. If there is need to draw suction and not collect tissues from the fluid stream, the suction line through which this stream is flowed is attached to fitting 1732. This may be the fitting to which the suction tube employed drawn by the anesthesiologist is attached. The suction line from which it may be desirable to collect a section of tissue is attached to fitting 1732. It should be appreciated that if a suction line is not attached to one of the fittings 1732 or 1734 the cap is left in place over the fitting. The cap thus prevents the unnecessary loss of suction through the fitting.

Mobile unit 30 is actuated by activating the suction pump 58. This suction is sufficient to flex both flapper valves 1814 into their open states. Should a suction line be attached to fitting 1732, a fluid stream is drawn through this suction line into cassette chamber 1704. From chamber 1704 this fluid stream flows through conduit 59 into the associated canister.

The suction drawn by pump 58 also causes a fluid stream to be drawn through the suction line attached to fitting 1734. The flange 1862 of trap 1850 serves as the cap that is removably fitted over housing opening 1729. When flange 1862 is in position, O-ring 1866 prevents the loss of suction at the outer interface between the front end of the cassette and trap flange 1862. When there is no interest in collecting material entrained in this stream, a filter 1880 is not disposed in trap holder 1852. The fluid stream flows unfiltered through the cassette and out through conduit 59.

Alternatively, when cassette is operated in this bypass mode, trap 1850 is not even fitted to the cassette. Cover 1741 is fitted over cassette opening 1729. The cover 1741 may include a layer of elastomeric material. This elastomeric layer functions as a seal that prevents the loss of suction at the interface between the cassette and the cover.

A user can collect a tissue sample such as a polyp using cassette 1700. If the cover 1741 is in place, the cover is removed by grasping handle 1742 and manually pulling on cover 1741. Tissue trap 1850 including catch tray 1880 is inserted into sleeve 1726. A user grasps flange 1862 and position proximal panel 1860 through opening 1729 into sleeve 1726 and bore 1727. Tissue trap 1850 slides into sleeve 1726 until O-ring 1866 abuts cap end 1706. O-ring 1866 provides a suction seal between flange 1862 and cap end 1706. This mode of operation is called the tissue sample collection mode because the suction fluid communication path is through tissue trap 1850.

Alternatively, if the cover is not in place, the filterless trap is simply withdrawn from the cassette. A filter 1880 is seated in the trap holder 1852. The trap is then reseated in sleeve 1726.

It should be appreciated that this process of inserting a trap with filter in the cassette interrupts the suction drawn at the head of the suction applicator. This interruption of suction serves to substantially eliminate the likelihood that the tissue the practitioner is interested in collecting is inadvertently drawn through the cassette and into the waste collection canister.

When tissue trap 1850 is seated in sleeve 1726, sensor 1897 detects the presence of tissue trap 1850 and recognizes identification device 1896. Sensor 1897 is in communication with controller 192 (FIG. 1B). Controller 192 can turn on light 1898 such that the interior of tissue trap 1850 is illuminated.

In the tissue sample collection mode, the waste stream is drawn along a suction fluid communication path 184 from the surgical site into the applicator 52, through the suction line 50B and into fitting 1734. This waste stream can include a tissue sample 398 entrained in the suction applicator 52 as a result of suction draw through the applicator. From fitting 1734, the waste stream travels through port 1728, cavity 1894, bottom mesh 1890, aperture 1725, flapper valve 1814, chamber 1704 and into conduit 59. From conduit 59, the waste stream flows into canister 36.

The tissue sample 398 is trapped by bottom mesh 1890 of catch tray 1880 within tissue trap 1850. This mode of operation is referred to as the tissue collection mode because the suction fluid communication path 184 travels through tissue trap 1850. It is noted that in order to collect samples in the tissue collection mode, it is not required to disconnect or re-connect the suction line 50B.

The plastic from which the cap 1702 and tissue trap 1850 is formed from is at least partially transparent allowing a user to view the tissue sample 398 within cavity 1894. The tissue sample 398 is illuminated within tissue trap 1850 by light source 1898.

Tissue trap 1850 is removed from sleeve 1726 by a user manually pulling on flange 1862 in a direction parallel to the horizontal axis of cassette 1700. After tissue trap 1850 is removed from sleeve 1726, catch tray 1880 containing tissue sample 398 is removed from holder 1852. A user grasps and lifts lip 1892 of catch tray 1880 at lowered edge 1857 of holder 1852 separating catch tray 1880 from holder 1852.

With additional reference to FIG. 14, after removing tissue catch tray 1880, the user places catch tray 1880 into specimen container 380 (FIG. 14) where it is submerged into preservative solution 389 thereby covering tissue sample 398. The user places cap 390 over specimen container 380. Cap retainer 392 aligns threads 391 and 387. As cap 390 is rotated onto specimen container 380, tabs 394 break separating cap 390 from cap retainer 392. A user can then pull on arm 395 to remove cap retainer 392 from specimen container 380. The specimen container 380 is sent to a pathology lab for analysis. Door 1741 can then be replaced over opening 1729 of sleeve 1726 to prevent any loss of suction.

It should be appreciated that this process of removing the tissue trap 1850 again interrupts the suction draw at the head of the suction applicator. This gives the practitioner the opportunity to briefly examine the trapped tissue to ensure that the whole of the sample the practitioner wanted to collect was in fact collected. If the practitioner decides additional collection of this sample is necessary, the practitioner can either reseat the present filter or fit a new filter to the cassette.

If at a later time during the procedure, the practitioner believes it useful to collect another tissue sample, another catch tray 1880 can be inserted into holder 1852 and the tissue trap 1850 can be re-inserted into sleeve 1726 and bore 1727 in order to collect another tissue sample. Multiple tissue samples may be collected using multiple screens 1880. Multiple tissue samples can be collected without disconnection or re-connection of the suction line 50B during the procedure.

Once the medical/surgical procedure is completed, and use of the mobile unit 30 is no longer required, suction lines 50A and 50B may be disconnected from fittings 1732 and 1734, respectively. Caps 1740 are then replaced on fittings 1732 and 1734, respectively and door 1741 is replaced over opening 1729. Cassette 1700 is then removed from receptacle 1699. Cassette 1700 is rotated so that tabs 1708 and 1709 align in slots 1618 and 1620, respectively. As a consequence of having to rotate the cassette 1700, the valve disk 1632 undergoes a like rotation. The rotation of the valve disk 1632 reorients the disk so the disk again covers the open end of the receiver adapter conduit 59.

Once cassette 1700 is properly positioned, the cassette is manually withdrawn from the receptacle 1699 closing door 1634. After drip stop 1774 passes over the distal end of the valve disk boss 1632, the opposed sections of the drip stop that define slot 1790 come together so as reclose opening 1770. The closing of the opening 1770 substantially eliminates leakage of waste material remaining in the cassette. Cassette 1700 and holder 1852 are disposed of as medical waste.

After use, the mobile unit 30 is coupled to a docker (not illustrated and not part of this invention.) Waste material in the canister 36 is flowed through the docker to a treatment facility.

It should likewise be recognized that in versions of the invention, the plastic from which the cassette 1700 and tissue trap 1850 are formed from are at least partially transparent. This provides medical personnel with a quick means to verify that the tissue sample has been collected. In addition, this provides medical personnel with a quick means to verify that the cassette has not been previously used and does not contain previously collected waste.

Because cassette 1700 is angled slightly or inclined upward when seated in receptacle 1699, tissue trap 1850 is also angled slightly upward. Any liquid waste adhering to tissue trap 1850 when it is removed will flow into sleeve 1726 preventing the waste from leaking into the surgical environment.

The angled orientation of cassette 1700 ensures that, when the mobile unit 30 is in operation, the proximal shell base opening 1770 is, in a gravity orientation, below inlet ports 1722 and 1728. This makes it unlikely that waste in the cassette can flow upstream towards ports 1722, 1728 or tissue trap 1850.

Flapper valve unit 1800 also stops the leakage of any waste from the cassette 1700 into suction lines 50A and 50B. Individual flapper valves 1814 normally cover the port 1722 and aperture 1725, when suction pump 58 is actuated, and a fitting cap 1740 is removed, the suction drawn by the pump is sufficient to generate a pressure head that flexes the flapper valve 1814 to an open position. The waste stream is thus able to flow into the cassette chamber 1704. When the pump is deactivated, hinge 1816 has sufficient resilient force to return the flapper valve 1814 against the adjacent face or wall to a closed position.

A tissue sample can be collected in a similar manner using tissue trap 1900 as was described using tissue trap 1850. Because tissue trap 1900 is a single unitary piece and does not have a separate screen, after a tissue sample is collected with tissue trap 1900 and tissue trap 1900 is removed from sleeve 1726, the entire tissue trap 1900 would be placed into a preservative container 380. In order to collect an additional tissue sample, another unused tissue trap 1900 would be inserted into sleeve 1726.

VI. Fifth Embodiment

A. Cassette

Figure 47:
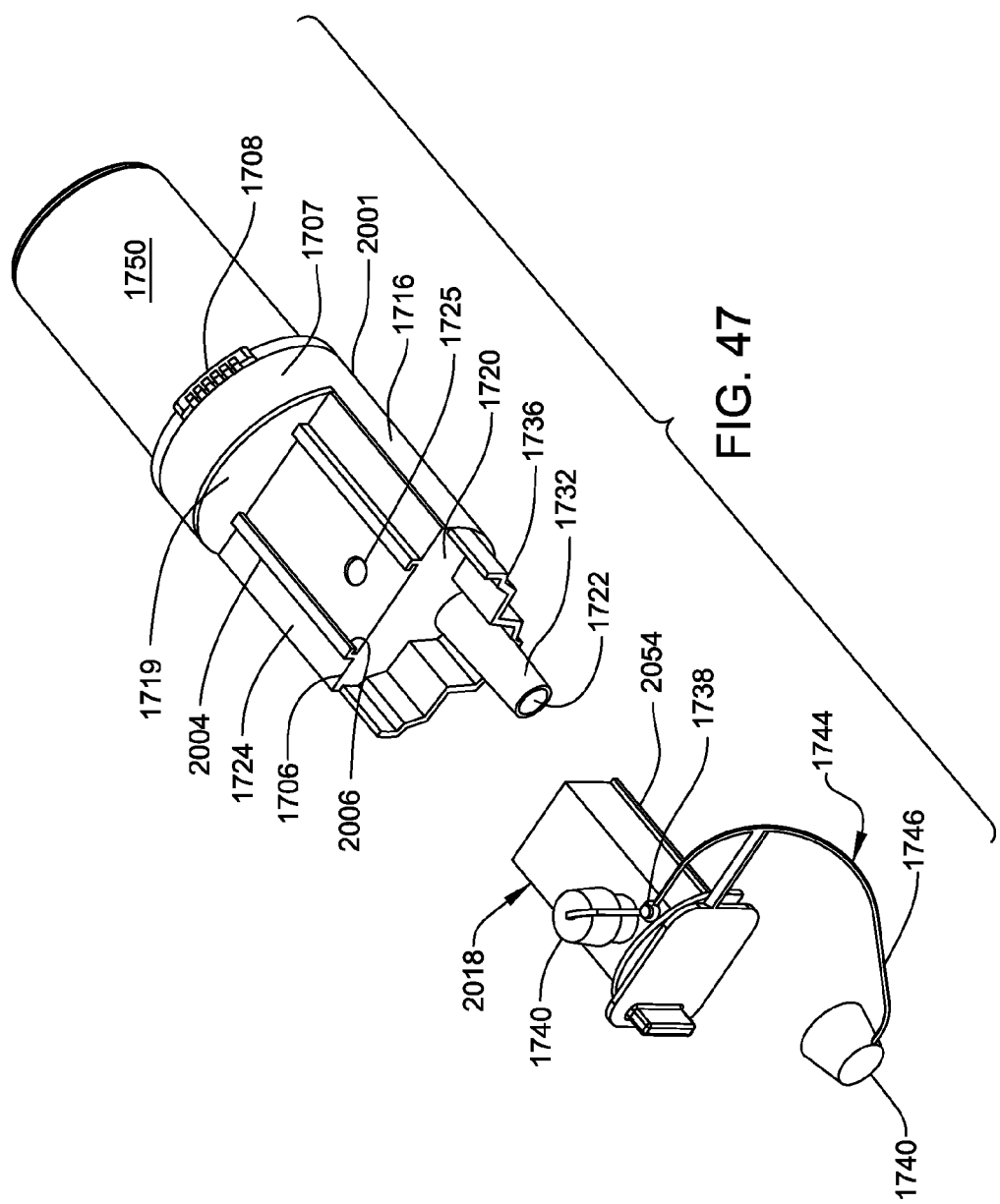
FIG. 47 is an exploded view of the manifold assembly of FIG. 46.
Figure 48A:
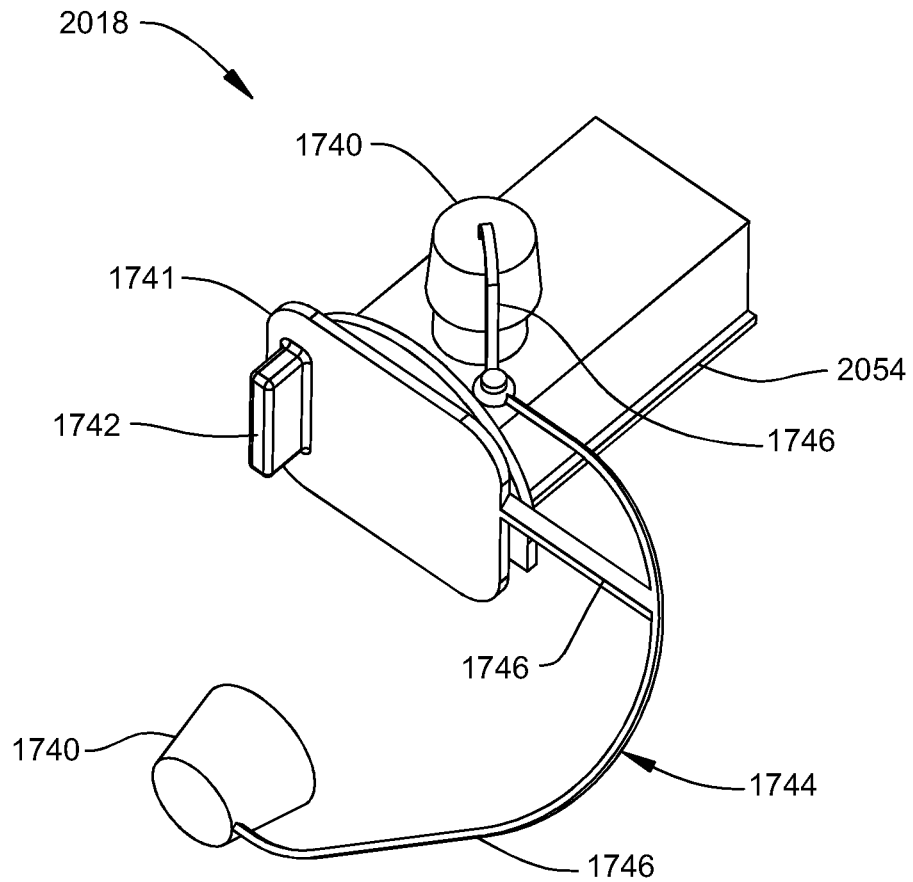
FIG. 48A is a perspective view of a tissue trap receiver with attached caps.
Figure 48B:
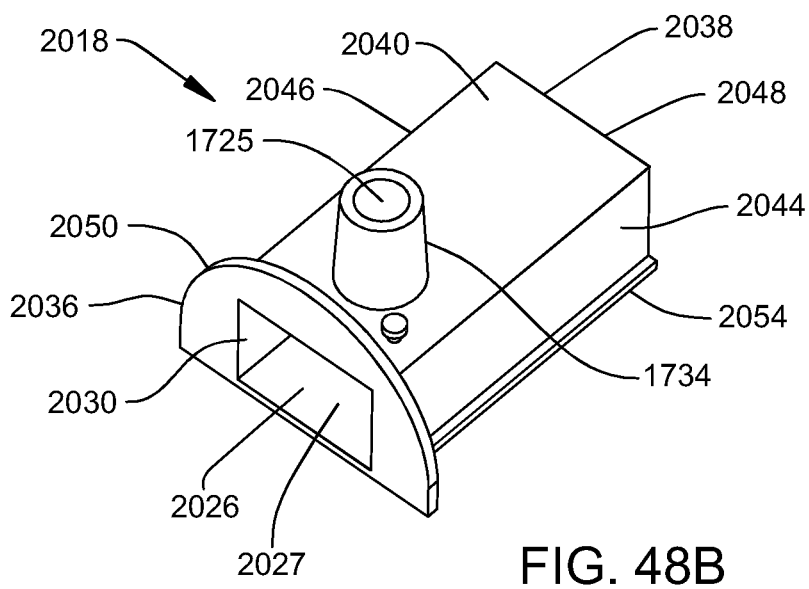
FIG. 48B is a perspective view of a tissue trap receiver with the caps removed.
Figure 50:
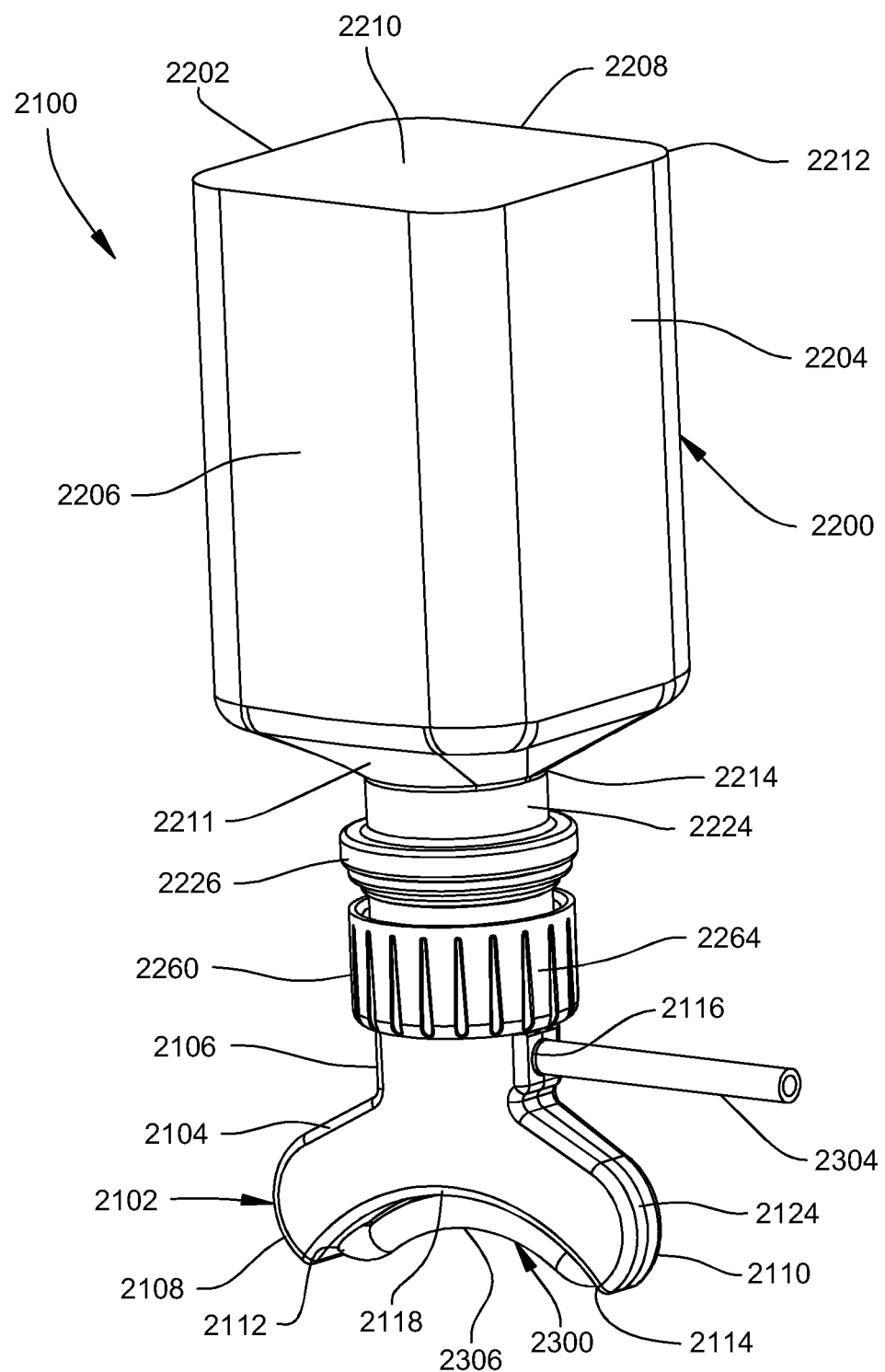

Turning now to FIGS. 46-48, another embodiment of a cassette 2000 is illustrated. Cassette 2000 is used in association with the receptacle 1699 of FIGS. 35 and 36. Cassette 2000 shares some common components and features with cassette 1700. The shell 1750 and tissue traps 1850 and 1900 of cassette 2000 are the same as previously described in cassette 1700. The interior features of cap 2002 are the same as previously described for cap 1702. However, housing or box 2018 is removable from cap 2002. Housing or box 2018 of cassette 2000 is molded separately from the rest of cap 2002. The housing or box 1718 of cap 1702 is a single unitary piece.

Cassette 2000 comprises a housing 2001 having a proximal shell 1750 with a distal attached cap 2002 and a removable sample housing or box 2018. Cap 2002 and sample housing 2018 can be formed from a suitable material such as injection molded plastic.

Cap 2002 has the same ends 1705 and 1706 and skirt as cap 1702. Cap 2002 is sized to allow the housing 1701 to be disposed in and rotated into receptacle 1699. At the proximal end 1705 of the skirt 1707, two tabs 1708 and 1709 project radial outwardly (only tab 1708 is shown in FIG. 47). Tab 1708 is designed to slip fit into manifold receptacle lock ring slot 1618. Tab 1709 is designed to slip fit into manifold receptacle lock ring slot 1620.

A half barrel 1716 extends distally from the lower half of skirt 1707. A semi-circular face 1719 extends over the proximal end of skirt 1707 and another semi-circular face 1720 extends over the proximal end of barrel 1716. A planar wall 1724 extends between face 1719 and face 1720. A pair of parallel diametrically opposed spaced apart L-shaped rails 2004 extends perpendicular upward from wall 1724. An elongated slot 2006 is located along the length of each of rails 2004. A circular aperture 1725 extends through wall 1724 between the center of rails 2004 and spaced from face 1720. In this version of the invention, for reasons that are apparent from the following description, aperture 1725 functions as an inlet port.

A generally U-shaped half flange 1736 extends in a distal direction away from face 1720. The fitting 1732 integral with cassette 1700 is integral with cassette 2000. As with cassette 1700, this fitting 1732 functions as fitting to which a fluid stream from which there is no need to collect tissue can be drawn through cassette 2000.

With additional reference to FIGS. 49A-49E, removable housing or box 2018 is generally rectangular in shape and comprises five sides or walls including parallel and spaced apart generally horizontally oriented top and bottom walls 2040 and 2042; parallel and spaced apart generally vertically oriented side walls 2044 and 2046; and a generally vertically oriented back wall 2048 that is perpendicular to walls 2044 and 2046. Housing 2018 has ends 2036 and 2038. A semicircular flange 2050 extends radially outward from walls 2040-2046 at end 2036. An elongated raised spline 2054 extends perpendicularly away from and along the length of each of side walls 2044 and 2046 at the bottom of side walls 2044 and 2046. Splines 2054 slide into and mate with slots 2006 of rails 2004 when sample housing 2018 is mounted to cap 2002.

An elongated rectangular shaped internal sleeve 2026 having a bore 2027 is defined in housing 2018 by walls 2040-2046. An opening 2030 is defined where sleeve 2026 terminates at flange 2050. An aperture 2052 extends through bottom wall 2042. Aperture 2052 functions as an outlet port.

A fitting 1734 extends perpendicularly away from top wall 2040. Fitting 1734 is in the form of a hollow tube. Fitting 1734 is sized to receive suction line 50B (FIG. 36). A port 1728 is defined through fitting 1734 and is in fluid communication with bore 2027.

A post 1738 extends perpendicularly away from top wall 2040 slightly spaced from flange 2050 and fitting 1734. Removable caps 1740 are provided for fittings 1732 and 1734. A removable cover 1741 is provided to cover opening 2030 of sleeve 2026. Cover 1741 has a handle 1742 that can be grasped by a user and a portion that fits into sleeve 1726. Each fitting cap 1740 and cover 1741 is integrally attached to sample housing 2018 by a tether 1744 with several arms 1746. Arms 1746 are anchored to post 1738.

Sample housing 2018 is attachable to cap 2002. A user would grasp housing 2018 and align splines 2054 with slots 2006 of rails 2004. Housing 2018 is moved in a proximal direction towards face 1719. Splines 2054 slide along rails 2004 until rear wall 2048 contacts face 1719. In this position, aperture 2052 of housing 2018 is in coaxial alignment with aperture 1725 of cap 2002. A fluid communication path is formed between port 1728, bore 2027, apertures 2052 and 1725 and chamber 1704.

Sample housing 2018 can be used with either tissue trap 1850 of FIGS. 42A-E or with tissue trap 1900 of FIGS. 45A-E. After cover 1741 is removed from opening 2030, either tissue trap 1850 or 1900 can be inserted into bore 2027 thereby completing cassette 2000 for use with receptacle 1699.

B. Operation of the Fifth Embodiment

Referring to FIGS. 1A-C, 36, 38B and 46-49, mobile unit 30 (FIG. 1A) is operated using cassette 2000 in a similar manner to cassette 1700. Mobile unit 30 is prepared for use by a user inserting the cassette 2000 with attached housing 2018 into the complementary receptacle 1699 associated with the canister 36. A user grasps the cap 2002 and inserts the cassette 2000 into the receptacle 1699 so that shell base 1752 opens door 1634 and slides into chamber 1610. Shell base 1752 is seated on valve disk 1632 and cap 2002 is retained in receptacle 1699 in the same manner as previously described.

The activation of suction pump 58 results in the drawing of fluid streams through fittings 1732 and 1734. The fluid stream drawn through fitting 1734 flows through box sleeve 2026 and out of aperture 2052. From box aperture 2052 the fluid stream flows into, through, cassette aperture 1725. In practice cassette aperture 1725 is larger in diameter and extends radially beyond the whole of the perimeter of box aperture 2052. This relative sizing and positioning of these apertures substantially eliminates the leakage of fluid between box 2018 and the adjacent surface of the cassette.

A user can elect to collect a tissue sample such as a polyp using cassette 2000. A user removes cover 1741 from sleeve 2026 by grasping handle 1742 and manually pulling on cover 1741. Tissue trap 1850 (FIGS. 42A-E) including catch tray 1880 is inserted into sleeve 2026. A user can grasp flange 1862 and position proximal panel 1860 through opening 2030 into sleeve 2026 and bore 2027. Tissue trap 1850 slides into sleeve 2026 until O-ring 1866 abuts flange 2050. O-ring 1866 provides a suction seal between flange 1862 and flange 2050. This mode of operation is called the tissue sample collection mode because the suction fluid communication path is through tissue trap 1850.

When the system is in the tissue sample collection mode, the waste stream is drawn along a suction fluid communication path 184 from the surgical site into the applicator 52, through the suction line 50B and into fitting 1734. This waste stream can include a tissue sample 398 entrained in the suction applicator 52 as a result of suction draw through the applicator. From fitting 1734, the waste stream travels through port 1728, cavity 1894, bottom mesh 1890 and out through aperture 2052, the outlet port of box 2018. The waste stream then passes through aperture 1725, the inlet port into half barrel 1716, across the open flapper valve 1814, chamber 1704 and into conduit 59. From conduit 59, the waste stream flows into canister 36.

The tissue sample 398 is trapped by bottom mesh 1890 of catch tray 1880 within tissue trap 1850. This mode of operation is referred to as the tissue collection mode because the suction fluid communication path 184 travels through tissue trap 1850. It is noted that in order to collect samples in the tissue collection mode, it is not required to disconnect or re-connect the suction line 50B.

Tissue trap 1850 is removed from sleeve 2026 by a user manually pulling on flange 1862 in a direction parallel to the horizontal axis of cassette 2000. After tissue trap 1850 is removed from sleeve 2026, catch tray 1880 containing tissue sample 398 is removed from holder 1852. A user grasps and lifts lip 1892 of catch tray 1880 at lowered edge 1857 of holder 1852 separating catch tray 1880 from holder 1852.

After removing tissue catch tray 1880, the user can place catch tray 1880 into a specimen container as previously described.

If at a later time during the procedure, the practitioner believes it useful to collect another tissue sample, another catch tray 1880 can be inserted into holder 1852 and the tissue trap 1850 can be re-inserted into sleeve 2026 and bore 2027 in order to collect another tissue sample. Multiple tissue samples may be collected using multiple screens 1880. Multiple tissue samples can be collected without disconnection or re-connection of the suction line 50B during the procedure.

A tissue sample can be collected in a similar manner using tissue trap 1900 with cassette 2000 as previously described using tissue trap 1900 with cassette 1700.

It is noted that in some examples, where mobile unit 30 is used during several surgical procedures in a day, it is advantageous to re-use portions of cassette 2000 during multiple procedures in order to reduce cost and the amount of medical waste generated. Specifically, cap 2002 and shell 1750 of cassette 2000 are re-used throughout the day with tissue housing 2018 being replaced for each new patient that mobile unit 30 is used with.

Sample housing 2018 is removable from cap 2002. Suction lines 50A and 50B are disconnected from fittings 1732 and 1734, respectively. Caps 1740 are replaced on fittings 1732 and 1734, respectively and door 1741 is replaced over opening 2030. A user would grasp housing 2018 and pull on housing 2018 thereby moving housing 2018 in a distal direction away from face 1719. Splines 2054 slide along rails 2004 until splines 2054 are separated from rails 2004. Sample housing 2018 is then disposed of as medical waste. Another sample housing 2018 is then mounted to cap 2002 as previously described.

At the end of the day when the medical/surgical procedures are completed, and use of the mobile unit 30 is no longer required, suction lines 50A and 50B may be disconnected from fittings 1732 and 1734, respectively. Caps 1740 are replaced on fittings 1732 and 1734, respectively and door 1741 is replaced over opening 2030. Cassette 2000 is then removed from receptacle 1699 in the same manner as previously described. Cassette 2000 and holder 1852 are disposed of as medical waste.

After use, the mobile unit 30 is coupled to a docker (not illustrated and not part of this invention.) Waste material in the canister 36 is flowed through the docker to a treatment facility.

It should likewise be recognized that in versions of the invention, the plastic from which the cassette 2000, including housing 2018 and tissue trap 1850 are formed from are at least partially transparent. This provides medical personnel with a quick means to verify that the tissue sample has been collected. In addition, this provides medical personnel with a quick means to verify that the cassette has not been previously used and does not contain previously collected waste.

Similarly, as when cassette 1700 is used to trap tissue, the suction flow is interrupted during the processes of installing and removing the trap. This reduces the initial likelihood that the tissue-of-interest may flow to the canister prior to collection. Post-collection this provides an opportunity for the practitioner to ensure that all the tissue of interest is collected prior to allowing the flow of the unfiltered fluid stream to the canister.

VII. Irrigation Cassette

An irrigation assembly 2100 for use with mobile unit 30 is illustrated in FIGS. 50-54. Irrigation assembly 2100 provides a source of irrigation fluid to a surgical site. Irrigation assembly 2100 comprises an irrigation cassette 2102 and a water bottle 2200.

Water bottle 2200 is generally rectangular in shape. Other shapes such as round or oval can be utilized. Water bottle 2200 is defined by six exterior panels including opposed parallel and spaced apart generally vertically oriented panels 2202 and 2204; opposed parallel and spaced apart generally vertically oriented panels 2206 and 2208; and a generally horizontally oriented bottom panel 2210. Top panel 2211 is angled inwardly from panels 2202, 2204, 2206 and 2208. Side panels 2202, 2204, 2206 and 2208 are perpendicular to bottom panel 2210. Water bottle 2200 has a top end 2214 and a bottom end 2212.

Panels 2202, 2204, 2206, 2208, 2210 and 2211 define a reservoir 2220 within water bottle 2100. Water bottle 2100 can be formed from any suitable material such as blow molded plastic. In one embodiment, water bottle 2100 is formed from a transparent material such that the contents or level of reservoir 2120 may be viewed by a user.

Water bottle 2100 has a neck 2224 that extends away from top wall 2211. An annular flange 2226 extends radially outward and encircles neck 2224. Threads 2228 are defined in the outer face of neck 2224 toward end 2214. Opening 2230 allows access to reservoir 2220.

A circular cap 2260 has threads 2262 defined on an inner annular surface of the cap and recessed knurled portions 2264 defined on an outer annular surface of the cap. Cap 2260 has a top wall 2266. A barbed fitting 2268 extends perpendicularly away from the outer surface of top wall 2266. Barbed fitting 2268 has a hollow tube therein. A U-shaped projection 2270 also extends perpendicularly away from the outer surface of top wall 2266. A hole 2272 is defined in projection 2270. Apertures 2274 and 2276 extend through top wall 2266.

A duck bill valve 2280 is seated in aperture 2276 and extends away from the inner surface of wall 2266 toward reservoir 2220. Duck bill valve 2280 is formed from a compressible, elastomeric material such as polyisoprene rubber. Duck bill valve 2280 has a pair of lips with a slit 2282 therebetween. Duck bill valve 2280 allows air to be drawn into reservoir 2220 during the operation of peristaltic pump 70. Air can pass from the ambient environment through slit 2282 into reservoir 2220. Liquid pressure from the contents of reservoir 2220 presses on the lips of duck bill valve 2280, keeping slit 2282 closed and preventing any liquid leakage from occurring. Duck bill valve 2280 is therefore a one way valve allowing air flow into water bottle 2200 and preventing liquid from leaving water bottle 2200.

An irrigation cassette 2102 is removably coupled to water bottle 2200. Irrigation cassette 2102 includes a generally Y-shaped housing 2104 and hose or tube 2300. Housing 2104 has ends 2106, 2108 and 2110. Apertures 2112, 2114, and 2116 extend through housing 2104 into an internal cavity 2120 within housing 2104. An inwardly curved wall 2118 extends between ends 2108 and 2110.

Housing 2104 is formed from two separate opposed halves or sections 2122 and 2150 that are snap fit together along a seam 2124. Section 2122 includes a planar wall 2123 and a curved outer peripheral side wall 2124 having an edge 2126. The upper section of wall 2123 terminates along an edge 2128. Side wall 2124 is generally perpendicular to wall 2123. Section 2150 has a planar wall 2152 and a pair of curved partial outer peripheral side walls 2154 and 2155 having edges 2156. Wall 2154 extends from end 2106 to end 2112. Wall 2155 extends from end 2106 to end 2114. The upper section of wall 2152 terminates along an edge 2158. A curved inverted Y-shaped wall 2118 is located within cavity 2120 and spaced from side walls 2154 and 2155. Curved wall 2118 is generally perpendicular to walls 2152. Several U-shaped tube retaining flanges 2119 are mounted to wall 2152 and extend perpendicularly away from wall 2152 into cavity 2120.

Side wall 2154 and wall 2118 define a tube channel 2160. Side wall 2155 and wall 2118 define a tube channel 2162. A tine 2164 extends perpendicularly inward from wall 2152 at edge 2158. A boss and slot 2166 extend perpendicularly inward from wall 2123 at edge 2128. Tine 2164 is dimensioned to be press fit into and received by slot 2166.

Tube 2300 includes ends 2302 and 2304, a curved roller contact section 2306 and bends 2308, 2310 and 2312. Tube 2300 can be formed from any suitable material such as an elastomer or silicone rubber.

Irrigation cassette 2102 is assembled in the following manner: First, tube 2300 is placed into housing section 2150 with bend 2310 positioned in channel 2160 and bend 2308 positioned in channel 2162. Tube 2300 is pressed against housing section 2150 such that tube 2300 slides into and is held by tube retaining flanges 2119. End 2302 is positioned flush with edge 2128. Curved roller contact section 2306 is adjacent to and in contact curved wall 2118. End 2304 extends through aperture 2116 and beyond side wall 2155.

Next, cap 2260 is positioned with housing section 2150 such that tine 2164 is press fit through cap hole 2272 and tube end 2302 is slid over barbed fitting 2268. Housing sections 2122 and 2150 are mated together to form housing 2104. Housing sections 2122 and 2150 are retained to each other by press-fitting, snap fitting or welding the two housing sections together. Other retention means such as adhesives can also be used. When housing sections 2122 and 2150 are mated, tine 2164 is press fit into slot 2166.

Irrigation assembly 2100 is completed by screwing cap 2260 and irrigation cassette 2102 onto water bottle 2200. Water bottle 2200 is filled with an irrigation fluid. Rotation of cap 2260 causes cap threads 2262 to mate with bottle threads 2228. An irrigation fluid communication path is formed for irrigation liquid to flow from reservoir 2220, through aperture 2274, fitting 2268 and tube 2300 to tube end 2304. Tube end 2304 can be connected with an irrigation line such as irrigation line 51 of FIG. 1A.

Figure 51:
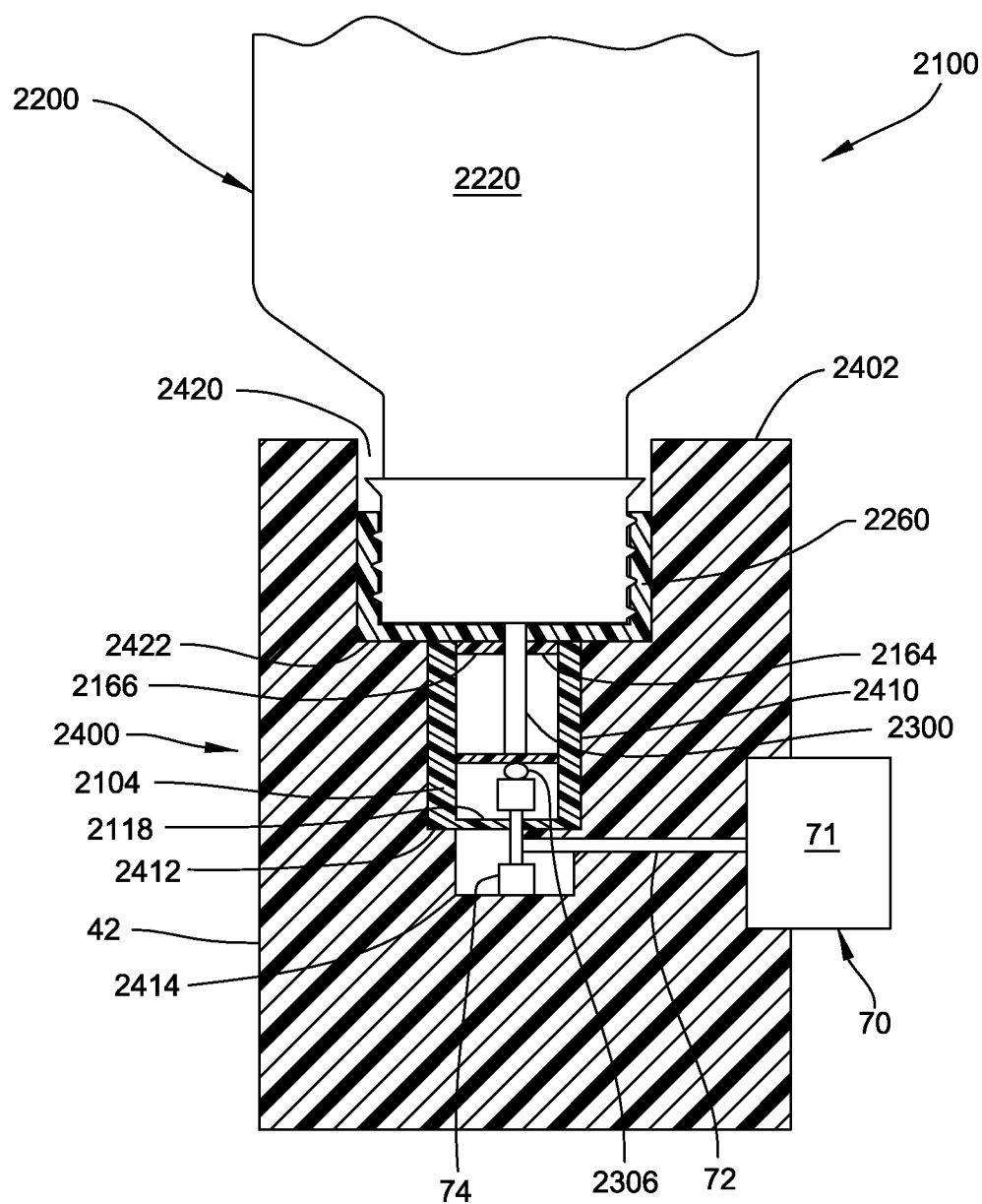
Figure 52:
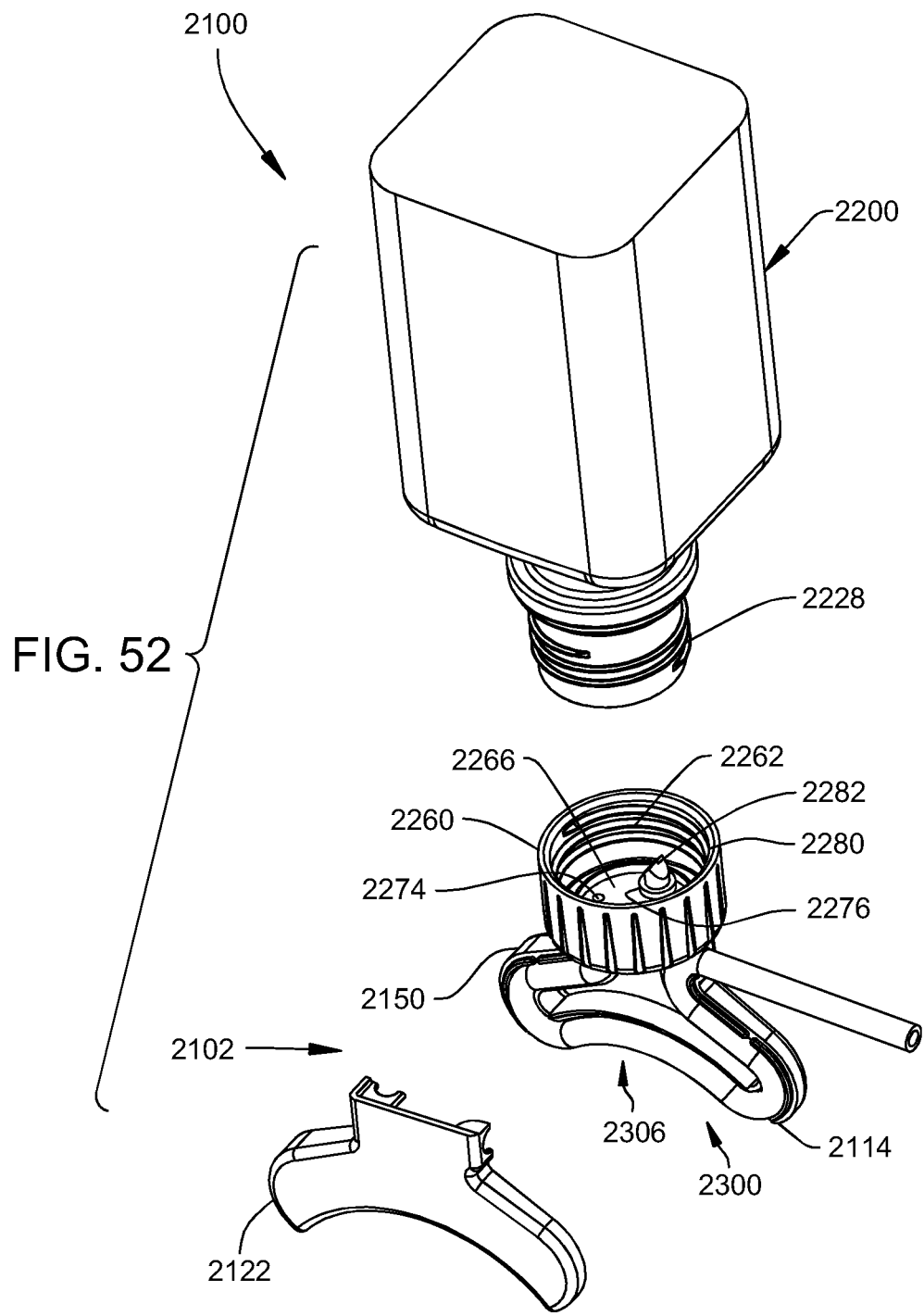
Figure 53:
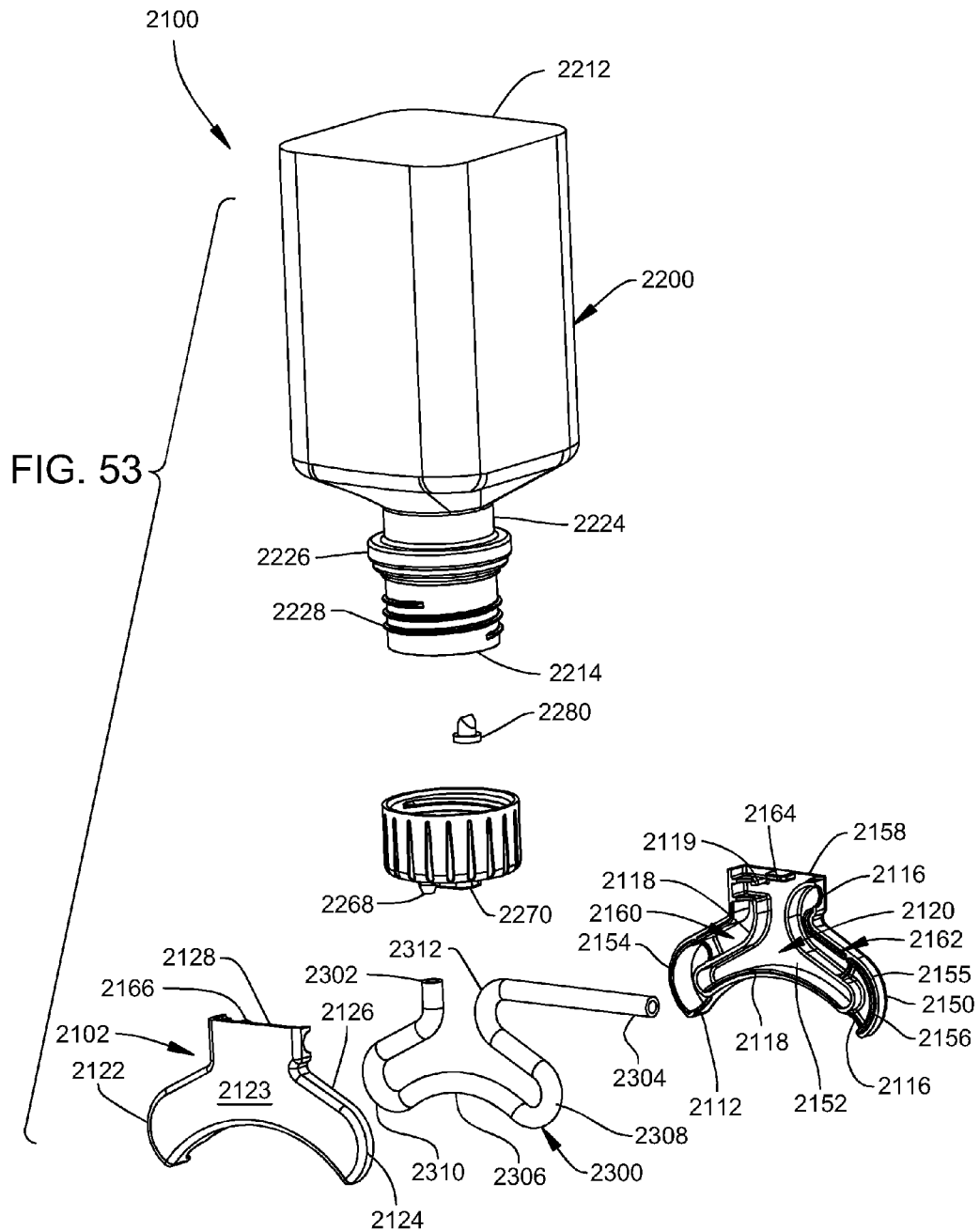
Figure 54:
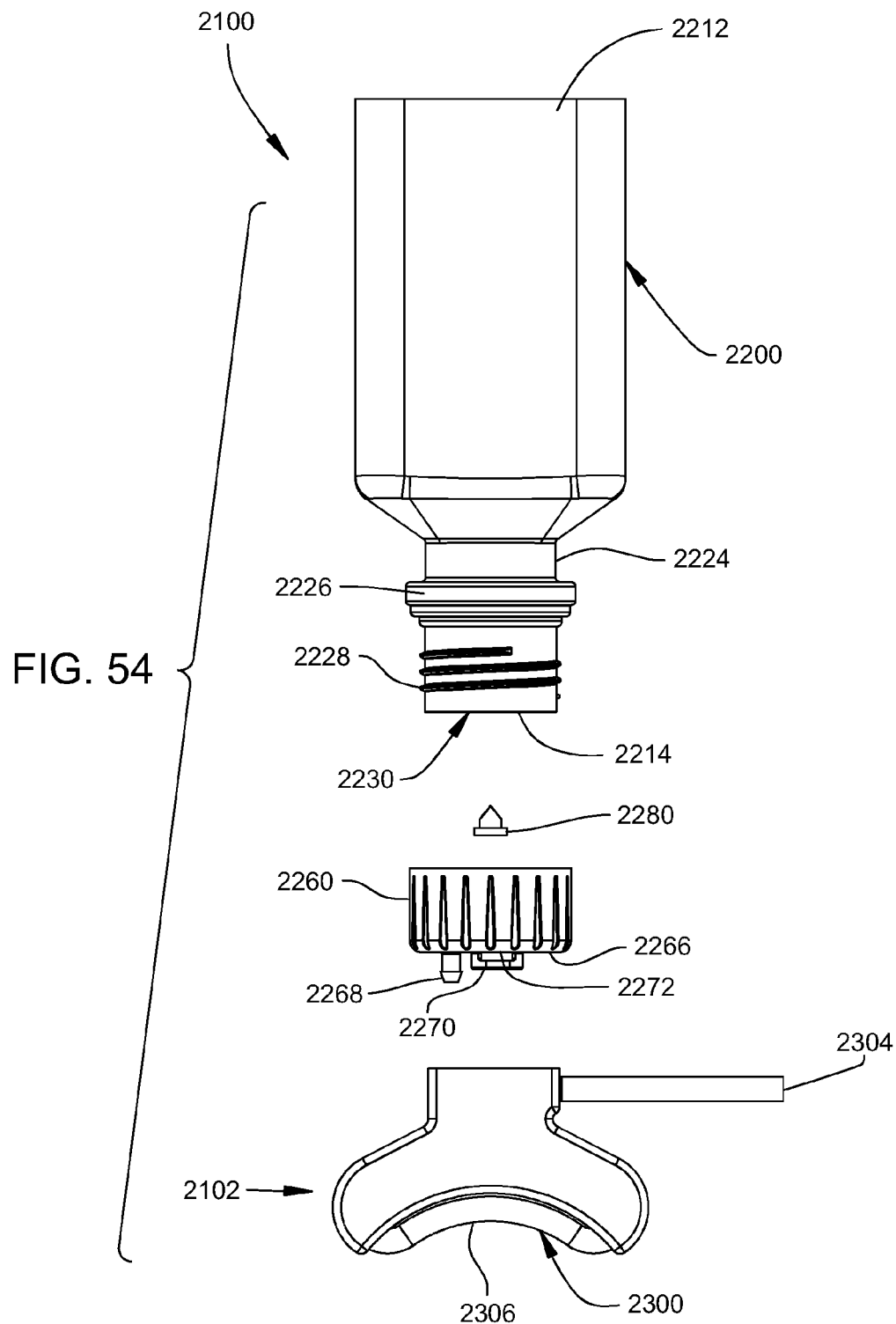

With specific reference to FIGS. 1A and 51, Irrigation assembly 2100 is adapted to be received by an irrigation assembly receiver 2400 that is part of mobile unit 30. Irrigation assembly receiver 2400 is positioned within cap 42 of mobile unit 30. Cap 42 has an upper surface 2402. A rectangular shaped slot 2410 extends into cap 42 from surface 2402 and has a bottom surface 2414. A rectangular shaped peripheral step 2412 extends into slot 2410. A counterbore 2420 is located above slot 2410 and extends from upper surface 2402 to slot 2410 and defines an annular step 2422.

Peristaltic pump 70 comprises a rotary electric motor 71 coupled to cap 42 that is connected by a shaft 72 to eccentric rollers 74. Electric motor 71 causes the rotation of rollers 74. Peristaltic pump rollers 74 press curved tubing section 2306 against wall 2118 such that irrigation fluid is forced through tube 2300.

Irrigation assembly 2100 is prepared for use by a user manually inserting irrigation assembly 2100 into slot 2410 and counterbore 2420 such that housing 2104 rests on step 2412 and cap 2260 rests on step 2422. In this position, peristaltic pump rollers 74 are engaged with and pressing curved tubing section 2306 against wall 2118. Tube end 2304 is connected with irrigation line 51 which is connected with applicator 52.

The activation of electric motor 71 and peristaltic pump 70 results in irrigation fluid being pumped along an irrigation fluid communication path 182 from water bottle 2200 reservoir 2220, through aperture 2274, fitting 2268 and tube 2300 to tube end 2304, irrigation line 51 and applicator 52 where it is supplied to a surgical site.

Figure 55:
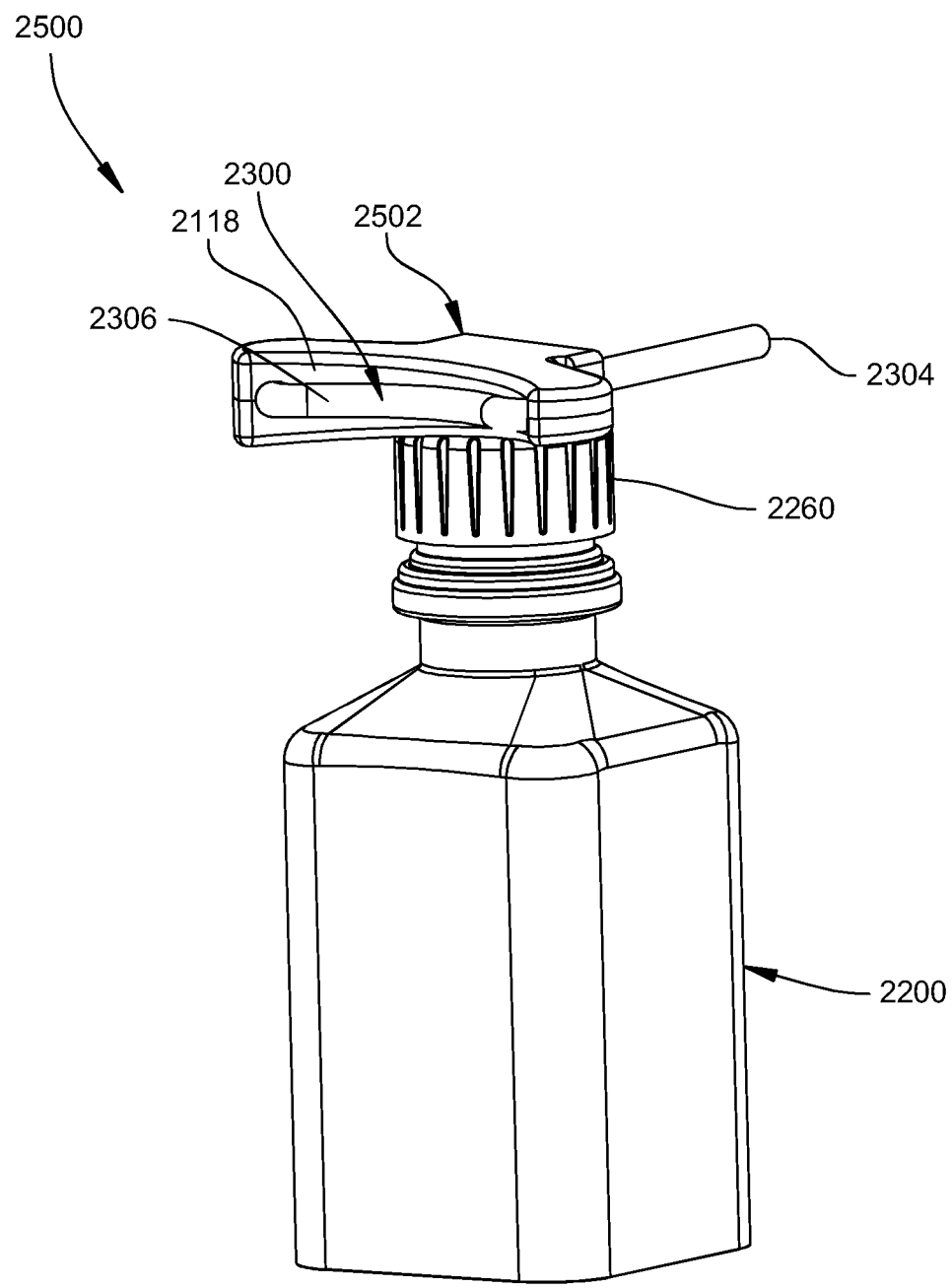
Figure 56:
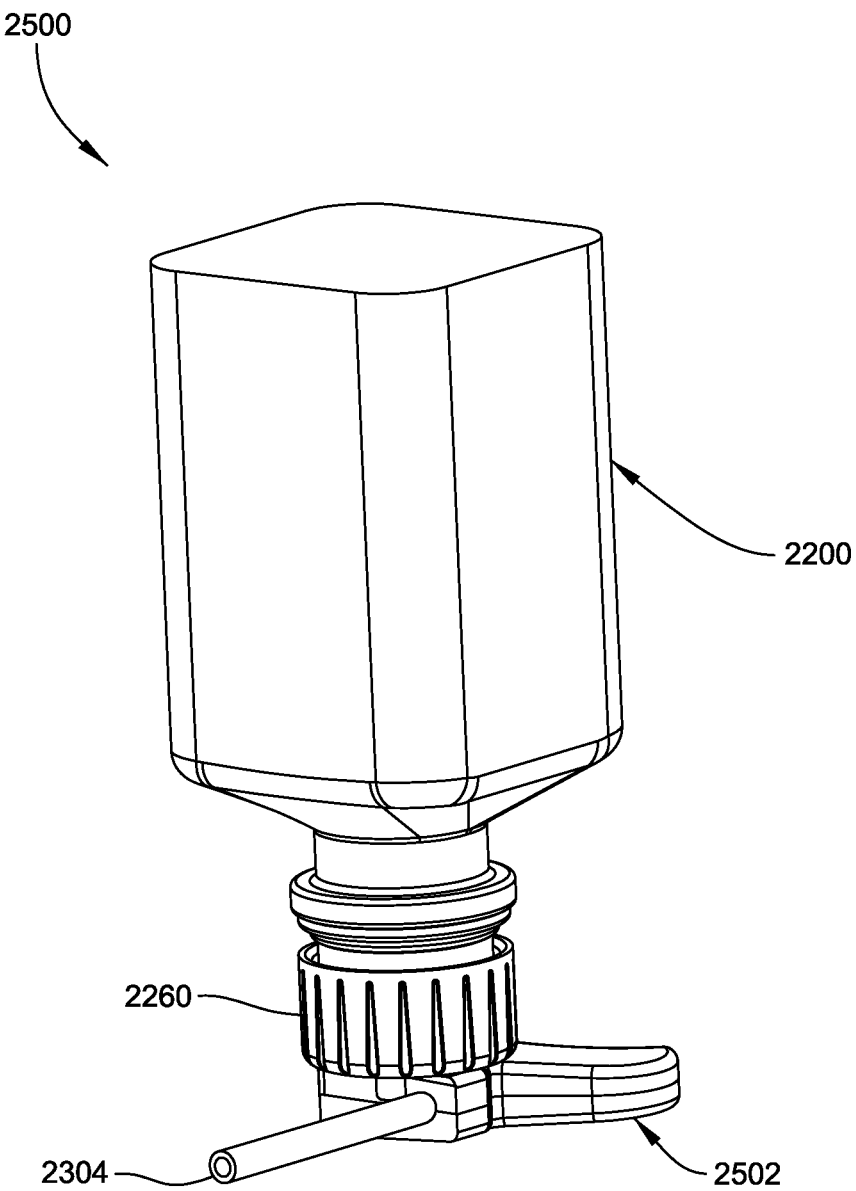

With reference to FIGS. 55 and 56, an alternative embodiment of an irrigation assembly 2500 for use with mobile unit 30 is illustrated in FIGS. 50-54. Irrigation assembly 2500 comprises an irrigation cassette 2502 and a water bottle 2200. Irrigation cassette 2502 has the same features as irrigation cassette 2102 except that irrigation cassette 2502 is oriented perpendicular or at a right angle to water bottle 2200 instead of parallel to water bottle 2200.

VIII. Sixth Embodiment

Figure 58:
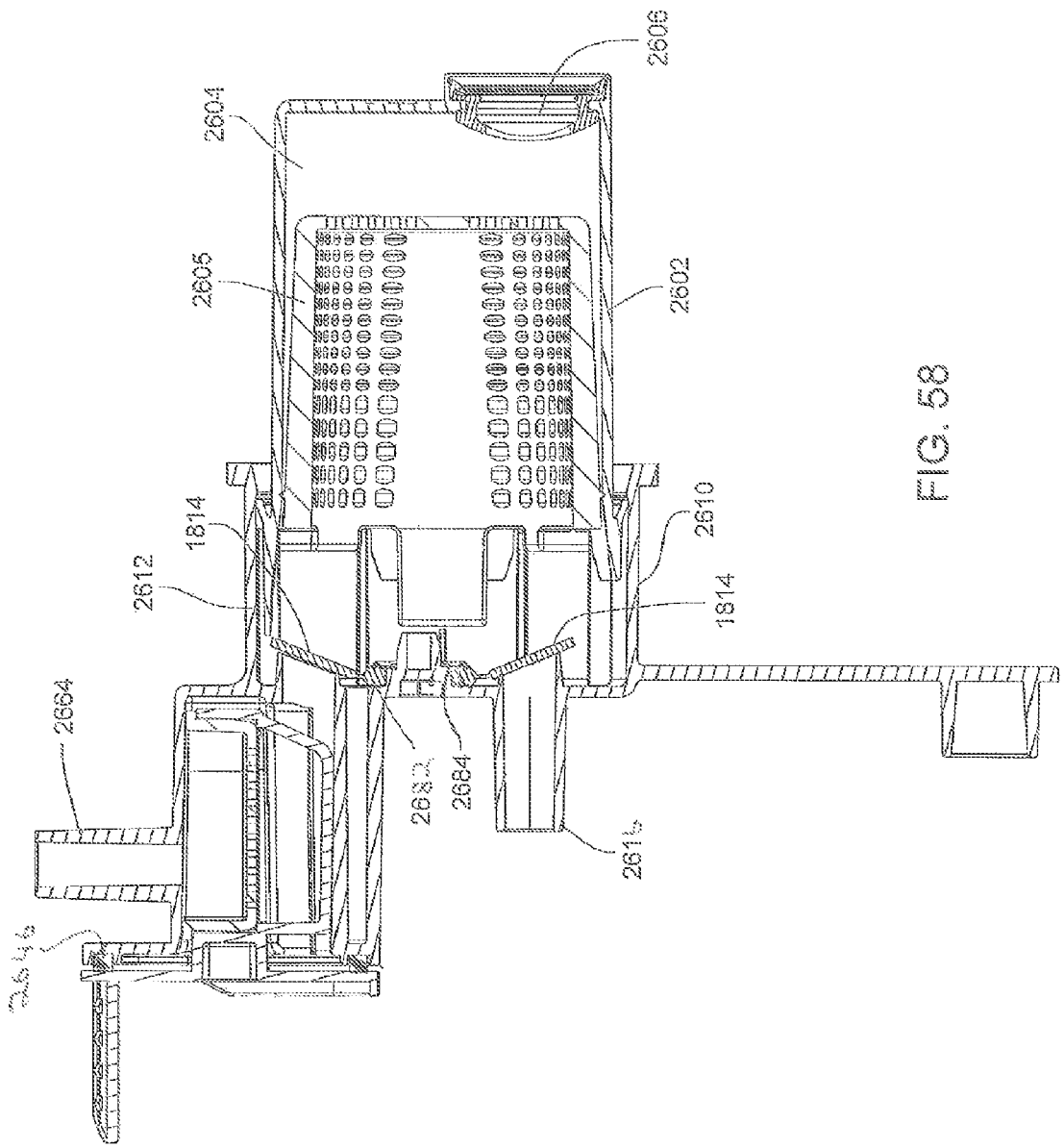

FIGS. 57 and 58 depict an alternative cassette 2600 of this invention. Cassette 2600 is a variation of cassette 1700. Cassette 2600 includes proximal shell 2602. Shell 2602 is similar in shape and structure to shell 1750. A cap 2610 is disposed over the distal end of shell 2602. A sleeve 2640 extends forward from cap 2610. Sleeve 2640 is formed with a void space 2652 that extends inwardly from an open proximal end of the sleeve. A screen holder 2702 is shaped to be slidably received in void space 2652. The screen holder is shaped to removably support a catch tray 2740 that includes a filter or screen 2741.

It can be seen that shell 2602 is formed to have parallel grooves (not identified) that extend along the outer wall of the shell. These grooves are not relevant to this invention. Shell 2602 defines a void 2604 through which fluid flows prior to discharge from an outlet 2606. A filter 2605 is shown removably fitted in shell void space 2604. The means by which the filter 2605 is disposed in shell 2602 is not part of the present invention.

The cassette cap 2610, now described by reference to FIGS. 57, 59 and 60, is formed as a single-piece unit and is shaped to have a cylindrical skirt 2612. Skirt 2612 is dimensioned to extend around the open distal end of shell 2602. An end plate 2614 that is generally circular in shape extends inwardly from the distal end of skirt 2612. The end plate 2614 forms the distal end of cap 2610. A fitting 2616 extends outwardly from the cap end plate 2614. Fitting 2616 is designed to receive a suction line 50. The bore through the fitting 2616 (bore not identified) leads into the void space 2604 within the cassette 2600 defined by shell 2602 and cap 2610. In the depicted version of the invention, fitting 2616 extends forward from a location that is radially spaced away from the center longitudinal axis of the cassette 2600, the axis through plate 2614 around which the cassette 2600 is rotated when in the receptacle 1699.

Sleeve 2640, as seen best in FIGS. 57, 59 and 60, is formed integrally with cap 2610. The sleeve 2640 extends forward from the cap end plate 2614. In the depicted version of the invention the outer body of sleeve 2640 is rectangular in cross section. It should be understood that this design feature is not limiting. An oval face plate 2642 extends around the distal end of sleeve 2640. In the depicted version of the invention, the major axis, the longitudinal axis through face plate and the center axis through fitting 2616 are located on diametrically opposed sides of the longitudinal axis through the cassette 2600.

The face plate 2642 is formed to have two oval webs, webs 2644 and 2648, that project distally forward. One web, web 2644, extends forward from around the outer perimeter of the face plate 2642. The second web, web 2468, is like web 2464 a closed loop web and is located inward from web 2464. A compressible seal 2646 is compressed between webs 2644 and 2648.

Sleeve 2640 is formed so that void space 2652 extends inwardly from the face plate 2642. The sleeve 2642 is formed so as that the void space 2652 includes an upper chamber 2654 and a lower chamber 2656. The upper chamber 2654 is essentially rectangular in cross shape. The upper chamber 2654 terminates at an interior surface of sleeve 2640. The sleeve lower chamber 2656 is located immediately below the upper chamber 2654. The lower chamber 2656 is generally rectangular in cross sectional shape. Lower chamber 2656 while generally of the same length as the upper chamber 2654, has a smaller cross section height and width than the upper chamber 2654. Void space also includes a groove 2658 that is located below the lower chamber 2656. Groove 2658 extends the length of the lower chamber 2656. The groove 2658 is semi-circular in cross sectional shape. The widest portion of the groove 2658, the portion immediately contiguous with the lower chamber 2656, has a width less than the width of the lower chamber.

In many versions of the invention the longitudinally extending interior surface of the sleeve 2640 that defines the top of the upper chamber 2654 and the longitudinally interior surface that defines the base of groove 2658 are parallel to each other. For manufacturing reasons these surfaces and these surfaces are slightly offset from the perpendicular relative to the plane of the sleeve face plate 2642. By extension the sleeve void space 2652 thus does not extend perpendicularly relative to the sleeve face plate 2642.

Cassette cap 2610 is further formed so that a fitting 2664 extends away from an upper surface of sleeve 2640. The fitting 2664 is shaped to receive a suction line 50. The bore through fitting opens into the top of the upper chamber 2654 of the void space 2642. The cassette cap 2610 is also shaped so that adjacent the distal end of the void space there is an opening 2666 that provides a fluid path through the cap end plate 2614. Opening 2666 is circular in shape. The cap 2610 is formed so that groove 2658 and the adjacent proximal end of the distal chamber extend to opening 2666. Fitting 2616 and opening 2666 are located on opposed sides of the cassette longitudinal axis that extends through end plate 2614.

In the depicted version of the invention, the sleeve 2640 is shown having a closed end bore 2670. Bore extends forward from the cap end plate 2614. Bore 2670 is present for manufacturing purposes and is not otherwise relevant to this invention.

A cylindrical boss 2678 extends inwardly from the inner, proximally directed surface of the cap end plate 2614. Boss 2678 is generally cylindrical in shape. A base 2676 extends around the portion of the boss 2678 that projects outward from the end plate 2614. The base has an outer diameter greater than that of boss 2676.

When cassette 2600 of this invention is assembled a valve assembly 2682, seen only in FIG. 28, is seated over base 2676 and boss 2678. Valve assembly 2682 is essentially identical to valve assembly 1800. Valve assembly 2682 valve is positioned so that one of the flapper valves 1814 seats over proximal open end of fitting 2616. The second flapper valve us seated over the structural features of cap 2610 that define opening 2666. Valve assembly 2682 has a hub (not identified) that is seated over base 2676. A ring 2684 press fit over boss 2678 holds the hub and, by extension the whole of valve assembly to the cap end plate 2614.

In the depicted versions of the invention, the cap 2610 has a tubes 2688 that is coaxial with fitting 2616 that extends beyond the inner face of end plate 2614. A tube 2690 extends proximally from and around opening 2666. Tubes 2688 and 2690 both have proximal ends that are angled, not perpendicular, relative to the longitudinal axis through the cassette 2600. Flapper valves 1814 seat against these proximal end openings of tubes 2688 and 2690. Owing to the resilient nature of the material forming valve assembly 2682, the valves 1814 are thus biased so as to be pressed against the proximal ends of tubes 2688 and 2690.

A fitting cap 2687 is molded with cassette cap 2610. A flexible tether 2686 also part of the molded assembly extends from a distal end of skirt 2612 to hold the fitting cap 2687 to the cassette cap 2610.

The screen holder 2702, sometimes called the tissue trap, is now described by reference to FIGS. 61A and 61B. The screen holder 2702 is formed as a single-piece unit. Screen holder 2702 is shaped to a face plate 2704. The face plate 2704 is shaped so that the outer perimeter of the proximally directed surface of the plate will seat against seal 2646. A pull tab 2706 extends perpendicularly away from the distally directed surface, the normally exposed surface, of plate 2704. The screen holder 2702 is shaped so that tab 2706 extends away from an upper portion of plate 2704. Screen holder is further shaped so that an indentation 2708 extends inwardly from the exposed surface of the face plate 2704. Indentation 2708 is present for molding purposes.

A tray holder 2712 extends from the proximal directed surface, the normally concealed surface of the face plate 2704. Tray holder 2712 is generally in the form of a U-shaped beam wherein the opposed ends of the beam are the portions of the beam adjacent the face plate 2704. The tray holder 2712 is formed so that the curved semi-circular portion of the tray holder has a number of spaced apart fingers 2714. Tabs 2716 extend inwardly from two of the fingers 2714. Tray holder 2712 is further formed so that a small triangular shaped rib 2718 (only one illustrated) extends outwardly from the opposed side surfaces of the hold. The tray holder is formed so that the side-to-side width between the outermost surfaces of the opposed ribs 2718 is approximately 0.5 mm greater than the cross sectional width across the upper chamber 2654 internal to sleeve 2640. Rims 2720 (two shown) extend inwardly from the inwardly directed surfaces of tray holder 2712. Rims 2720 are located adjacent the bottom edges of the tray holder 2712.

Two legs, legs 2724 and 2728, extend downwardly from tray holder 2720. Leg 2724, the distal of the two legs, extends directly downwardly from the tray holder 2720. While not apparent in FIG. 61B, leg 2724 is located proximally away from face plate 2704. Leg 2728, the proximal of the two legs extends downwardly and distal forward from the curved proximal end of the tray holder. A skid 2726 extends between the free ends of legs 2724 and 2728. Legs 2724 and 2728 and skid 2726 are dimensioned to seat in groove 2658 internal to sleeve 2640.

Catch tray 2740 is similar in design to catch tray 1880. The screen 2741, shown diagrammatically in FIG. 57, for trapping tissue forms the base of the catch tray. Screen 2741 is essentially identical to screen 1890. A set of walls 2742 extend upwardly from the outer perimeter of the screen. A rim 2744 extends outwardly from the top edges of walls 2742. The catch tray 2740 is dimensioned to seat within the void defined by the opposed sides and proximal end of tray holder 2720. The catch tray 2740 is further dimensioned so that when the tray is so seated, the proximal curved side wall 2742 at the proximal end of the tray abuts tray holder tabs 2716 so as to cause the outward flexure of fingers 2714. The force imposed by the tray holder fingers 2714 and tabs 2716 against the catch tray 2740 as they attempt to return to their unbiased positions serves to removably hold the tray in the tray holder 2712.

In some versions of the invention the components forming cassette 2600 are constructed so that the when the catch tray 2740 is fitted to the tray holder 2712 the distance from the bottom surface of skid 2726 to the top surface of the catch tray rim 2744 is approximately 0.5 mm greater than the top to bottom height of the surfaces internal to sleeve 2640 that define the top of the upper chamber 2654 and the base of groove 2658.

Cassette 2600, like cassette 1700, is readied for use by the insertion and rotation of the cassette 2600 in the receptacle 1699 as seen in FIG. 62. A suction line 50 through which a fluid stream that contains tissue samples worth collecting is attached to fitting 2664. A suction line 50 through which a fluid stream that does not contain tissue samples worth collecting is attached to fitting 2616. In this version of the invention it should be appreciated that the sleeve 2640 and therefore void space 2652, is spaced forward from the rest of the cassette 2600.

The screen holder 2702 is seated in sleeve void space 2652. Owing to the width between the outer surfaces of the screen holder ribs 2718 being slightly greater than the width across the upper chamber 2654 of void space 2652, the ribs press against the inner surfaces of sleeve 2640 that define the chamber 2652. This serves to slightly compression hold the screen holder 2704 to sleeve 2640. During time periods in which there is no need to collect specimens from the stream flowing through fitting 2664 a catch tray is not seated in the tray holder 2740. When the cassette 2600 is operated in this state the fluid stream flow from fitting 2664 through void space 2652 and opening 2666. From opening 2664 the fluid flows into the void space 2604 across filter 2605 and out through outlet opening 2606. Since a catch tray 2740 is not fitted to the screen holder 2704, this fluid stream is not filtered as it transits the sleeve void space 2652.

It should be realized that during operation of the cassette 2600, the inner surface of the screen holder face plate 2704 is disposed against seal 2646. The abutment of plate 2704 against seal 2646 prevents the loss of suction between the interface of sleeve 2640 and the screen holder 2702.

When it is useful to collect a specimen, screen holder 2702 is removed from sleeve 2640 so a catch tray 2740 can be fitted to the holder. This step can be performed while maintaining the suction draw on the cassette 2600. The screen holder 2702 is removed by pulling on tab 2706. More specifically, owing to the positioning of the tab 2706, the pulling on the tab results in the outward and downward pivoting of the screen holder face plate 2704 relative to seal 2646 fitted to sleeve 2640. In other words, the individual performing this action is able to, by using face plate 2704 as a lever, break the suction force that holds the plate to the sleeve 2640.

Once the screen holder 2702 is withdrawn from sleeve 2640, the catch tray 2740 is seated in the tray holder 2712. As discussed above, owing the flexure of fingers 2714, the tray holder fingers 2714 and tabs 2716 releasable hold the catch tray in the void within the tray holder 2712. The screen holder is then reinserted in the sleeve void space 2652.

In versions of the invention wherein the top to bottom height between the catch tray rim 2744 and skid 2726 is greater than the top to bottom height between the top of the upper chamber 2654 and the base of the groove 2658, the tray holder legs 2724 and 2728 flex. Owing to the resilient nature of the material from which the screen holder 2702 is formed, the legs 2724 and 2728 place a force on the catch tray 2740 through the tray holder 2712. This force urges the catch tray rim 2744 against the inner surface of the sleeve 2640 that defines the upper chamber 2654. When fluid again flows through the screen void space 2652 this serves to ensure that essentially the whole of the fluid stream from fitting 2666 flows across the screen integral with catch tray 2640. Any large item in this fluid stream, ideally the tissue the practitioner wants to capture for study, is thus trapped in the catch tray 2740.

It should be appreciated that owing to the design of the cassette 2600, the sleeve 2640 is located forward of the manifold receptacle 1690. Typically the cassette 2600 or at least the sleeve 2640 is formed from material that is transparent. Collectively these features of the invention make it possible for the medical personnel to observe the flow through the sleeve void space 2652 before the fluid stream flows into the waste collection unit. This makes it possible for the personnel to determine when the tissue required for study becomes trapped in the catch tray 2740.

The ability to quickly view the catch tray 2740 is further enhanced by the fact that sleeve 2640 is located forward of the rest of the cassette 2600, the cassette housing. This prominent position of the sleeve causes an individual to naturally direct his/her eyes to the sleeve and the catch tray seated in the sleeve.

In an alternative version of this embodiment of the invention, the catch tray is integral with the screen holder. In these versions of the invention an additional component, essentially just face plate 2704, is also provided. This face plate functions as a second cap that is fitted to sleeve 2640 when there is no need to collect a specimen from the stream that is discharged into the cassette through fitting 2666.

IX. Alternative Embodiments

While the invention has been described with reference to exemplary embodiments, it will be understood by those skilled in the art that various changes may be made and equivalents may be substituted for elements and features thereof without departing from the scope of the invention. For example, it is contemplated that elements and/or features of one embodiment may be combined or substituted with elements and/or features of another embodiment. In addition, many modifications may be made to adapt a particular system, device or component thereof to the teachings of the invention without departing from the essential scope thereof. It is intended that the invention not be limited to the particular embodiments disclosed for carrying out this invention.

For example, not all versions of the inventions may have all the features described. The features of the different embodiments of the invention may be combined. Likewise, there is no requirement that all versions of the invention include the described highly mobile waste collection unit, rover 30. For example, in some versions of the invention the waste collection unit may simply consist of a mobile or static unit that is connected to an external suction source. The manifold receptacle and complementary manifold are mounted to the waste collection unit.

For example, there is no requirement that all versions of this invention include a mechanism that, in addition to serving as a suction conduit, supplies irrigation fluid. Likewise, while the system is generally designed for use as part of system that collects medical waste, other versions of the inventions may not have this functionality. Thus some versions of this invention may only have relatively small canisters, canisters capable of holding 10 liters or less of waste. In these versions of the invention, the waste is collected solely as a byproduct of the primary objective of performing the procedure; the retrieval of the tissue. In these versions of the invention, it should be appreciated that the cassette is therefore not provided with components that facilitate the pumping of fluid to the site to which the suction applied.

Likewise, use of this invention is not limited to a system for collecting tissue from the gastrointestinal tract. In other versions of the invention, the suction applicator may be designed for insertion into the esophagus. The suction applicator would therefore be used to draw material, including tissue from the esophagus or the stomach. Still another version of this invention may be used with devices inserted into the pulmonary passageways. These versions of the invention can be used to selectively retrieve tissue from either these passageways or the lungs.

Further in some versions of the invention, the cassette may have its own filter. When the system is not being tissue collection mode, the fluid stream withdrawn from the site to which the suction applicator is applied is flowed through this filter. This filter therefore serves to trap solids that, could potentially adversely affect the operation of the other components of the waste collection unit. These solids include sutures and bits of tissue that practitioner does not want to preserve for additional study.

In this version of the invention, the tissue trap is selectively placed in line with this cassette filter so as to be upstream of the cassette filter. When the practitioner is aware that a section of tissue the suction applicator is about to entrained in the fluid stream, by either the positioning of the tissue trap of the actuation of the valves, the tissue trap is placed in line with the cassette filter.

In the version of the invention described with respect to FIGS. 35-44, the screen 1890 need not always be rectangular. In some versions of the invention if the screen is curved a single wall may extend around the perimeter of the screen to define the cavity in which the tissue is trapped. Likewise there is no requirement that in all versions of this embodiment of the invention that the second fitting, fitting 1732 be provided. Further, alternative means may be provided for releasably holding the catch tray 1880 to holder 1852. These alternative engagement mechanisms include magnets and snap fittings. In versions of the invention wherein the catch tray is suspended to the holder the tray may be suspended from a single beam that extends from the holder.

The backflow prevention valves that prevent backflow through fittings 1732 and 1734 may be different what have been described. For example, a one way valve such as an umbrella valve may be mounted in each of the fittings 1732 and 1734.

Similarly, in some versions of the invention the outlet opening 1770 in the cassette may be located in center of the proximal end base of the cassette. Likewise, there is no requirement that in all cassettes of this invention designed to rotate in the complementary receive that that the shell have a cylindrical side wall. In alternative versions of the invention, the shell may have a polygonal in shape.

A benefit of this version of the invention, is that the suction stream is always filtered to prevent the introduction of potentially damage causing material into the downstream components of the collection system. When it is desirable to retain a section of tissue for study, the tissue can be retrieved without having to extract it from the filled with waste cassette filter. The tethers that hold caps 1740 to the fittings 1732 and 1734 may be deleted. Further there is no requirement that in all versions of the invention the cassette be provided with the bypass fitting, fitting 1732. In still other versions of the invention, plural bypass fitting may be provided to any one of the cassettes of this invention.

Structures other than an O-ring 1866, for example a gasket, may provide the seal between the flange 1862 of the tissue trap 1850 and the adjacent end 1706 of cap 1702.

Various means may be used to control the components of this invention. For example a footswitch assembly, not illustrated may be provided. The one or more footswitches integral with this assembly may be used to control the suction pump or the irrigation pump. Therefore, it is an object of the appended claims to cover all such variations and modifications that come within the true spirit and scope of this invention.

What is claimed is:

1. A specimen collection cassette for use with a medical fluid collection system, said cassette including:
    a housing configured for removable attachment to the fluid collection system wherein, said housing is shaped to have: a sleeve, the sleeve having first and second opposed and spaced apart interior surfaces that at least partially define a first void space of said housing; an aperture in the second interior surface; and an outlet opening located proximal to the aperture through which fluid is able to flow from the first void space and through the aperture into the medical waste collection system;
    a first fitting attached to said housing to which a first suction line that extends from a medical/surgical site can be attached, said first fitting opening into a bore formed in the first interior surface of said sleeve;
    a supplemental opening formed in said housing that is separate from the bore in the first interior surface of said sleeve, the aperture in the second interior surface of said sleeve and the outlet opening of said housing, the supplemental opening into the first void space of said housing; and
    a cap that is removably attached to said housing so as to seat over the supplemental opening, said cap having an inner surface that is directed toward said housing first void space; and
    a catch tray that is removably attached to the inner surface of said cap and shaped to occupy said housing first void space, said catch tray having a porous screen and at least one wall that extends upwardly from an outer perimeter of said screen so that said screen and said at least one wall collectively define an open ended cavity so that, when said catch tray is attached to said cap and said cap is disposed over the supplemental opening, the cavity is open to the bore in the first interior surface of said sleeve into which said first fitting opens and said screen is disposed against the second interior surface of said sleeve so that fluid flows from the first fitting through said housing first void space, across the porous screen and through the aperture in the second interior surface of said sleeve to the outlet opening.

2. The specimen collection cassette of claim 1 wherein:
    the second interior surface of said sleeve is a surface of a wall in said housing that separates the housing first void space from a second void space of said housing wherein said housing outlet opening opens from the second void space and the aperture in the second interior surface of said sleeve is an aperture formed in said wall which fluid can flow from the first void space into the second void space; and
    a second fitting for receiving a second suction line separate from the first suction line that extends from said housing and said second fitting opens directly into the second void space of said housing.

3. The specimen collection cassette of claim 2, wherein:
    a first backflow prevention valve is mounted to said housing to prevent backflow from the second void space of said housing into the first void space of said housing; and
    a second backflow prevention valve is mounted to said housing to prevent backflow from the second void space of said housing into said housing second fitting.

4. The specimen collection cassette of claim 3, wherein said first and second backflow prevention valves are formed as a single unit.

5. The specimen collection cassette of claim 1, wherein:
    at least one beam extends from said cap so as to extend into the first void space of said housing; and
    a lip extends outwardly from said at least one wall of said catch tray and is positioned to extend over said at least one beam so as to releasably suspend said catch tray from said beam.

6. The specimen collection cassette of claim 5, wherein:
    said at least one beam is arranged to form a slot; and said screen and said lip of said catch tray are collectively shaped so that said screen seats in the slot and said lip extends over the at least one slot-forming beam.

7. The specimen collection cassette of claim 6, wherein said at least one beam of said catch tray is shaped so the slot is fully enclosed by said beam.

8. The specimen collection cassette of claim 1, wherein: said housing has a base that forms a proximal end of said housing wherein the base has a center; and said outlet opening of said housing is formed in the base of said housing and the outlet opening has a center that is spaced from the center of said housing base.

9. The specimen collection cassette of claim 1, wherein: said housing has a shell that forms a proximal portion of said housing, the shell having a cylindrical outer wall; and the outlet opening of said housing is formed in said shell.

10. The specimen collection cassette of claim 1, wherein said housing is formed so that the first void space of said housing is a closed end bore.

11. The specimen collection cassette of claim 1, wherein a seal is located between said housing and said cap to prevent the loss of suction between said housing and said cap.

12. The specimen collection cassette of claim 11, wherein said seal is attached to said cap.

13. The specimen collection cassette of claim 1, wherein said housing includes:
a main body in which the outlet opening is formed, the main body having a surface with an inlet port that is separate from the outlet opening; and
a box that is removably attached to the main body so as to seat over the surface in which the inlet port is formed, the box defining said sleeve of said housing so as to define the first void space, the aperture and the supplemental opening, and wherein said first fitting extends from said box so as to open into the first void space and said box is further formed so that when said box is attached to said main body of said housing, a fluid communication path is established between the aperture in the second interior surface of said sleeve and the inlet port of said main body.

14. A specimen collection cassette for use with a medical fluid collection system, said cassette including:
a housing configured for removable attachment to the fluid collection system, said housing having: an interior wall that separates an interior of the housing into a first void space and a second void space, the interior wall having an aperture through which fluid can flow from the first void space into the second void space; an outlet opening that extends from the second void space through which fluid is able to flow from the first void space, the aperture in the interior wall and the second void space and into a fluid collection system; and a supplemental opening in said housing that is separate from the outlet opening, the supplemental opening into the first void space;
a first fitting attached to said housing to which a first suction line that extends from a medical/surgical site can be attached, said first fitting opening into the first void space;
a first backflow prevention valve is mounted to said housing to prevent backflow from said housing second void space, through the aperture in the interior wall of said housing and into the first void space of said housing; and a cap that is removably attached to said housing so as to seat over the supplemental opening of said housing, said cap having an inner surface that is directed to said housing first void space;
a porous screen that is removably attached to the inner surface of said cap and shaped to occupy said housing first void space so that, when said screen is attached to said cap and said cap is disposed over the supplemental opening of said housing, fluid that flows from the first fitting through the first void space of the housing into the second void space of the housing for discharge out of the outlet opening of said housing, the fluid flows across said screen;
a second fitting attached to said housing for receiving a second suction line that is separate from the first suction line, said second fitting opening directly into the second void space of said housing; and
a second backflow prevention valve mounted to said housing to prevent backflow from said housing second void space into said second fitting.

15. The specimen collection cassette of claim 14, wherein said first and second backflow prevention valves are formed as a single unit.

16. The specimen collection cassette of claim 14, wherein:
at least one beam extends from said cap so as to extend into said housing first void space; and
a lip extends outwardly from said screen and positioned to extend over said at least one beam to releasably suspend said screen from said beam.

17. The specimen collection cassette of claim 16, wherein:
said at least one beam is arranged to form a slot; and
said screen and said lip are collectively shaped so that said screen seats in the slot and said lip extends over the at least one slot-forming beam.

18. The specimen collection cassette of claim 17, wherein said at least one beam is shaped so the slot is fully enclosed by said beam.

19. The specimen collection cassette of claim 14, wherein: said housing has a base that forms a proximal end of said housing wherein the base has a center; and said outlet opening is formed in the base of said housing and the outlet opening has a center that is spaced from the center of said housing base.

20. The specimen collection cassette of claim 14, wherein: said housing has a shell that forms a proximal portion of said housing, the shell having a cylindrical outer wall; and the outlet opening of said housing is formed in the shell.

21. The specimen collection cassette of claim 14, wherein said housing is formed so that the first void space of said housing is a closed end bore.

22. The specimen collection cassette of claim 14, wherein a seal is located between said housing and said cap to prevent the loss of suction between said housing and said cap.

23. The specimen collection cassette of claim 22, wherein said seal is attached to said cap.

24. The specimen collection cassette of claim 14, wherein said housing includes:
a main body in which the outlet opening is formed, the main body having a surface with an inlet port that is separate from the outlet opening, the main body defining the second void space of said housing; and
a box that is removably attached to the main body so as to seat over the surface in which the inlet port is formed, the box including the interior wall with the aperture of said housing and further defining the first void space and the supplemental opening of said housing wherein, said box is further formed so that, when said box is seated over the surface of said main body in which the inlet port is formed, a fluid communication path is established between the aperture of the interior wall and the inlet port of the main body; and wherein said first fitting extends from said box so as to open into the first void space and said second fitting extends from said main body of said housing so as to open into the second void space.

25. A specimen collection cassette for use with a medical fluid collection system, said cassette including:
a housing configured for removable attachment to the fluid collection system, said housing defining a first void space and further shaped to have an outlet opening formed in said housing through which fluid drawn through said fitting is able to flow from the first void space and into the fluid collection system;
a first fitting attached to said housing to which a first suction line that extends from a medical/surgical site can be attached, said first fitting opening into the first void space;
a supplemental opening formed in said housing that is separate from said first fitting and the outlet opening of said housing, the supplemental opening into the first void space;
a cap that is removably attached to said housing so as to seat over the supplemental opening, said cap having an inner surface that is directed toward said housing first void space and a beam that extends inwardly from first surface so that, when said cap is seated over the supplemental opening, the beam is disposed in the first void space of said housing; and
a catch tray, said catch tray including a porous screen and a lip that extends outwardly from said screen, wherein said beam of said cap and said lip of said catch tray are collectively arranged so that said lip releasably suspends said catch tray from said beam and said beam and said catch tray positioned so that, when said catch tray is suspended from said beam and said cap is disposed over the supplemental opening, fluid that flows from the first fitting through said housing first void space, across said screen of said catch tray to the outlet opening of said housing.

26. The specimen collection cassette of claim 25, wherein:
said housing is formed with an interior wall that separates an interior of said housing into the first void space and a second void space, the interior wall is formed to have an aperture that provides a fluid communication path from the first void space to the second void space and so that that the outlet opening of said housing opens from the second void space; and
said housing, said cap and said catch tray are collectively shaped so that, when said catch tray is suspended from said beam and said cap is disposed over the supplemental opening of said housing, said screen is disposed over the aperture in the interior wall of said housing.

27. The specimen collection cassette of claim 25, wherein:
said at least one beam is arranged to defining a slot; and
said beam and said catch tray are collectively shaped so that said screen seats in the slot and said lip extends over the at least one slot-defining beam.

28. The specimen collection cassette of claim 27, wherein said at least slot-defining beam is shaped so the slot (1864) is fully enclosed by said beam.

29. The specimen collection cassette of claim 25 wherein said housing is formed with a wall that separates the housing first void space from a second void space wherein said housing outlet opening opens from the second void space and said wall is formed with an aperture through which fluid can flow from the first void space into the second void space;
said housing, said cap and said catch tray are collectively shaped so that, when said catch tray is suspended from said beam and said cap is disposed over the supplemental opening of said housing, said screen is disposed over the aperture in the interior wall of said housing and
a second fitting for receiving a second suction line separate from the first suction line extends from said housing and said second fitting opens directly into said housing second void space.

30. The specimen collection cassette of claim 25, wherein: said housing has a base that forms a proximal end of said housing wherein the base has a center; and said outlet opening is formed in said base and the outlet opening to has a center that is spaced from the center of said housing base.

31. The specimen collection cassette of claim 25, wherein: said housing has a shell that forms a proximal portion of said housing, said shell having a cylindrical outer wall; and the outlet opening is formed in the shell.

32. The specimen collection cassette of claim 25, wherein said housing is formed so that the first void space is a closed end bore.

33. The specimen collection cassette of claim 25, wherein a seal is located between said housing and said cap to prevent the loss of suction between said housing and said cap.

34. The specimen collection cassette of claim 33, wherein said seal is attached to said cap.

35. The specimen collection cassette of claim 25, wherein said housing includes:
a main body in which the outlet opening is formed, the main body having a surface with an inlet port that is separate from the outlet opening; and
a box that is removably attached to the main body so as to seat over the surface in which the inlet port is formed, said box defining the first void space and the supplemental opening of said housing, said box also having and an outlet port that extends from the first void space and that is positioned so that when said box is attached to the main body, a fluid communication path is established between the outlet port of said box and the inlet port of said main body; and
wherein said first fitting extends from said box so as to open into the first void space of said housing.

36. A specimen collection cassette for use with a medical fluid collection system, said cassette including:
a housing configured for removable attachment to the fluid collection system, said housing including:
a main body, said main body having a surface with an inlet port and an outlet opening that is separate from the inlet port through which fluid is drawn so to flow from the inlet port, through the main body of said housing and out through the outlet opening; and
a box that is removably attached to said main body so as to seat over the surface in which the inlet port is formed, the box defining a first void space of the housing and an opening into the first void space and an outlet port separate from the opening, the outlet port extending from the first void space and positioned so that, when said box is attached to said main body a fluid communication path is formed from the first void space through the outlet port of said box and the inlet port of said main body into the main body of said housing;

a first fitting attached to said box to which a first suction line that extends from a medical/surgical site can be attached, said first fitting opening into the first void space of said housing;

a cap that is removably attached to said box so as to seat over the opening into the first void space of said housing, said cap having an inner surface that is directed toward said housing first void space; and a porous screen that is removably attached to the inner surface of said cap and shaped to occupy said housing first void space so that, when said screen is attached to said cap and said cap is disposed over the supplemental opening, fluid that flows from the first fitting through said housing first void space to the outlet opening flows across said screen.

37. The specimen collection cassette of claim 36, wherein: said body of said housing has a base that forms a proximal end of said housing wherein said base has a center; and said outlet opening is formed in said base and the outlet opening has a center that is spaced from the center of said base.

38. The specimen collection cassette of claim 36, wherein a seal is located between said housing and said cap to prevent the loss of suction between said housing and said cap.

39. The specimen collection cassette of claim 36, wherein said main body of said housing and said box of said housing are shaped so that, when so that, when said box is attached to said main body, the outlet port of said box is in alignment with inlet port of said main body.

* * * * *